United States Patent
Haydon et al.

(10) Patent No.: US 8,389,516 B2
(45) Date of Patent: *Mar. 5, 2013

(54) ANTIBACTERIAL COMPOSITIONS

(75) Inventors: David John Haydon, Yarnton (GB); Lloyd George Czaplewski, Yarnton (GB); Nicholas John Palmer, Essex (GB); Dale Robert Mitchell, Essex (GB); John Frederick Atherall, Essex (GB); Christopher Richard Steele, Essex (GB); Tamara Ladduwahetty, Essex (GB)

(73) Assignee: Biota Europe Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/154,592

(22) Filed: Jun. 7, 2011

(65) Prior Publication Data

US 2011/0263590 A1 Oct. 27, 2011

Related U.S. Application Data

(62) Division of application No. 12/304,303, filed as application No. PCT/GB2007/002314 on Jun. 21, 2007, now Pat. No. 7,977,340.

(30) Foreign Application Priority Data

Jun. 22, 2006 (GB) .................................. 0612428.3

(51) Int. Cl.
- A61K 31/5377 (2006.01)
- A61K 31/501 (2006.01)
- A61K 31/497 (2006.01)
- A61K 31/496 (2006.01)
- A61K 31/506 (2006.01)
- A61K 31/4436 (2006.01)
- A61K 31/428 (2006.01)
- A61K 31/429 (2006.01)
- C07D 239/42 (2006.01)

(52) U.S. Cl. ............... 514/230.5; 514/232.5; 514/233.8; 514/252.03; 514/252.11; 514/253.1; 514/255.05; 514/256; 514/265.1; 514/269; 514/274; 514/275; 514/300; 514/333; 514/338; 514/367

(58) Field of Classification Search .................. None
See application file for complete search history.

(56) References Cited

U.S. PATENT DOCUMENTS 3,725,428 A 4/1973 Janiak
4,028,374 A 6/1977 Pelosi, Jr. et al.

FOREIGN PATENT DOCUMENTS

| EP | 1790640 | | 5/2007 |
|---|---|---|---|
| NL | 6916457 | A | 5/1970 |
| WO | 01/57008 | A | 8/2001 |
| WO | 01/97786 | A | 12/2001 |
| WO | 02/060879 | A | 8/2002 |
| WO | 2005/012292 | A | 2/2005 |
| WO | 2005/037845 | A1 | 4/2005 |
| WO | 2006/028226 | A | 3/2006 |
| WO | 2007/148093 | | 12/2007 |

OTHER PUBLICATIONS

Snyder et al., J. Med. Liban 48(4): 208-214, 2000 (PubMed Abstract provided).*
Shastry et al. Indian Journal of Heterocyclic Chemistry, vol. 13, Jul.-Sep. 2003, pp. 57-60.*
Morissette et al. "High-throughput crystallization: polymorphs, salts, co-crystals and solvates of pharmaceutical solids." Advanced Drug Delivery Reviews 2004, 56, 275-300.
Souillac, et al., Characterization of Delivery Systems, Differential Scanning Calorimetry, pp. 217-218 (in Encyclopedia of Controlled Drug Delivery, 1999, John Wiley & Sons, pp. 212-227).
Vippagunta, Sudha R. "Crystalline Solids." Advanced Drug Delivery Reviews 48(2001): 3-26.

\* cited by examiner

Primary Examiner — Joseph K. McKane
Assistant Examiner — Alicia L Otton
(74) Attorney, Agent, or Firm — Banner & Witcoff, Ltd.

(57) ABSTRACT

Compounds of formula (I) have antibacterial activity:

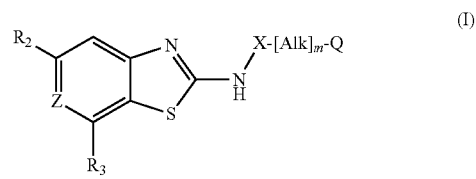

wherein: m is 0 or 1; Q is hydrogen or cyclopropyl; Alk is an optionally substituted, divalent $C_1$-$C_6$ alkylene, alkenylene or alkynylene radical which may contain an ether (—O—), thioether (—S—) or amino (—NR)— link, wherein R is hydrogen, —CN or $C_1$-$C_3$ alkyl; X is —C(=O)$NR_6$—, —S(O)$NR_6$—, —C(=O)O— or —S(=O)O— wherein $R_6$ is hydrogen, optionally substituted $C_1$-$C_6$ alkyl, $C_2$-$C_6$ alkenyl, $C_2$-$C_6$ alkynyl, -Cyc, or —($C_1$-$C_3$ alkyl)-Cyc wherein Cyc is optionally substituted monocyclic carbocyclic or heterocyclic having 3-7 ring atoms; Z is N or CH, or CF; $R_2$ and $R_3$ are as defined in the description.

31 Claims, No Drawings

ANTIBACTERIAL COMPOSITIONS

RELATED CASES

This application is a divisional of U.S. Ser. No. 12/304,303 filed Jan. 23, 2009, now U.S. Pat. No. 7,977,340, entitled "Antibacterial Compositions", whereby 12/304,303 is a National Stage application of PCT application PCT/GB2007/002314 filed Jun. 21, 2007, which claims the benefit of Great Britain application number 0612428.3 filed Jun. 22, 2006. These applications are incorporated hereby by reference in their entireties.

BACKGROUND TO THE INVENTION

Type II topoisomerases catalyse the interconversion of DNA topoisomers by transporting one DNA segment through another. Bacteria encode two type II topoisomerase enzymes, DNA gyrase and DNA topoisomerase IV. Gyrase controls DNA supercoiling and relieves topological stress. Topoisomerase IV decatenates daughter chromosomes following replication and can also relax supercoiled DNA. Bacterial type II topoisomerases form a heterotetrameric complex composed of two subunits. Gyrase forms an $A_2B_2$ complex comprised of GyrA and GyrB whereas topoisomerase forms a $C_2E_2$ complex comprised of ParC and ParE. In contrast eukaryotic type II topoisomerases are homodimers. Ideally, an antibiotic based on the inhibition of bacterial type II topoisomerases would be selective for the bacterial enzymes and be relatively inactive against the eukaryotic type II isomerases. The type II topoisomerases are highly conserved enzymes allowing the design of broad-spectrum inhibitors. Furthermore, the GyrB and ParE subunits are functionally similar, having an ATPase domain in the N-terminal domain and a C-terminal domain that interacts with the other subunit (GyrA and ParC respectively) and the DNA. The conservation between the gyrase and topoisomerase IV active sites suggests that inhibitors of the sites might simultaneously target both type II topoisomerases. Such dual-targeting inhibitors are attractive because they have the potential to reduce the development of target-based resistance.

Type II topoisomerases are the target of a number of antibacterial agents. The most prominent of these agents are the quinolones. The original quinolone antibiotics included nalidixic acid, cinoxacin and oxolinic acid. The addition of fluorine yielded a new class of drugs, the fluoroquinolones, which have a broader antimicrobial spectrum and improved pharmacokinetic properties. The fluoroquinolones include norfloxacin, ciprofloxacin, and fourth generation quinolones gatifloxacin and moxifloxacin. The coumarins and the cyclothialidines are further classes of antibiotics that inhibit type II topoisomerases, however they are not widely used because of poor permeability in bacteria, eukaryotic toxicity, and low water solubility. Examples of such antibiotics include novobiocin and coumermycin A1, cyclothialidine, cinodine, and clerocidin.

The continuous emergence of antibiotic resistance demands that novel classes of antibiotics continue to be developed. In pursuit of that goal, WO 02/060879, WO 03/105846 and WO 2005/012292 relate to benzimidazole, and pyridoimidazole compounds which inhibit bacterial gyrase activity. However, alternative compounds that inhibit bacterial topoisomerases are required.

BRIEF SUMMARY OF THE CONTEXT OF THE INVENTION

This invention is based on the finding that a class of substituted benzothiazoles and thiazolopyridines has antibacterial activity, as evidenced by inhibition of bacterial growth by members of that class. The compounds exhibit activity against strains of Gram-positive, Gram-negative and atypical bacteria, such as staphylococci, enterococci, streptococci, haemophili, moraxellas, chlamydophilas, legionellas and mycoplasmas for example *Staphylococcus aureus, Staphylococcus epidermidis, Enterococcus faecalis, Enterococcus faecium, Streptococcus pneumoniae, Streptococcus pyogenes, Haemophilus influenzae, Moraxella catarrhalis, Chlamydophila pneumonia, Legionella pneumophila* and *Mycoplasma pneumoniae*. The compounds with which the invention is concerned are therefore useful for the treatment of bacterial infection or contamination, for example in the treatment of, inter alia, Gram-positive infections and community acquired pneumonias.

Whilst the invention is not limited by any particular hypothesis as to the mechanism of action of the compounds, it is presently believed that such activity is due, at least in part, to the compounds inhibiting the type II bacterial topoisomerases.

The invention therefore encompasses the antibacterial use of the class of substituted benzothiazole and thiazolopyridine compounds defined herein, and to novel members of that class of compounds.

International Patent Application No. WO 2001057008 relates to benzothiazoles said to be useful for treatment of cancer and conditions in which angiogenesis is a contributory mechanism. That document does not state or imply that the compounds with which it is concerned have antibacterial activity, nor does it disclose the substituted benzothiazole and thiazolopyridine compounds claimed herein.

DESCRIPTION OF THE INVENTION

According to the invention, there is provided the use of a compound of formula (I), or a salt, hydrate, solvate or N-oxide thereof, in the preparation of an antibacterial composition:

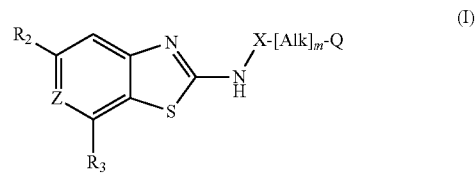

(I)

wherein:
m is 0 or 1;
Q is hydrogen or cyclopropyl;
Alk is an optionally substituted, divalent $C_1$-$C_6$ alkylene, alkenylene or alkynylene radical which may contain an ether (—O—), thioether (—S—) or amino (—NR)— link, wherein R is hydrogen, —CN or $C_1$-$C_3$ alkyl;
X is —C(=O)NR$_6$—, —S(O)NR$_6$—, —C(=O)O— or —S(=O)O— wherein R$_6$ is hydrogen, optionally substituted $C_1$-$C_6$ alkyl, $C_2$-$C_6$ alkenyl, $C_2$-$C_6$ alkynyl, -Cyc, or —($C_1$-$C_3$ alkyl)-Cyc wherein Cyc is optionally substituted monocyclic carbocyclic or heterocyclic having 3-7 ring atoms;
Z is N or CH, or CF;
$R_2$ is a group $Q^1$-[$Alk^1$]$_q$-$Q^2$-, wherein
q is 0 or 1;
$Alk^1$ is an optionally substituted, divalent, straight chain or branched $C_1$-$C_6$ alkylene, or $C_2$-$C_6$ alkenylene or $C_2$-$C_6$ alkynylene radical which may contain or terminate in an ether (—O—), thioether (—S—) or amino (—NR)— link;

$Q^2$ is an optionally substituted divalent monocyclic carbocyclic or heterocyclic radical having 5 or 6 ring atoms or an optionally substituted divalent bicyclic carbocyclic or heterocyclic radical having 9 or 10 ring atoms;

$Q^1$ is hydrogen, an optional substituent, or an optionally substituted carbocyclic or heterocyclic radical having 3-7 ring atoms;

$R_3$ is a group $Q^4$-$[Alk^2]_p$-$[Q^3]_q$- other than hydrogen wherein p and q are independently 0 or 1;

$Alk^2$ is optionally substituted divalent $C_1$-$C_6$ alkylene or $C_2$-$C_6$ alkenylene or $C_2$-$C_6$ alkynylene radical;

$Q^3$ is an optionally substituted divalent monocyclic carbocyclic or heterocyclic radical having 5 or 6 ring atoms or an optionally substituted divalent bicyclic carbocyclic or heterocyclic radical having 9 or 10 ring atoms;

$Q^4$ is hydrogen, an optional substituent, or optionally substituted carbocyclic or heterocyclic having 3-7 ring atoms.

In other broad aspects, the invention includes:

(i) a method of treatment of a subject suffering a bacterial infection, or preventing bacterial infection in a subject, comprising administering to the subject an amount of a compound (I) as defined above, sufficient to inhibit bacterial growth;

(ii) a method treating or preventing bacterial contamination of a substrate comprising applying to the site of such contamination or potential contamination an amount of a compound (I) as defined above, sufficient to inhibit bacterial growth;

(iii) a compound (I) as defined above for use in a method of treatment of the human body;

(iv) a compound (I) as defined above for use in treating or preventing bacterial infection.

Compounds of formula (I) as defined above but wherein q is 1 in substituent $R_3$, and salts, hydrates, solvates and N-oxides thereof, are believed to be novel per se, and thus form another aspect of the invention. Specifically, such compounds wherein $Q^2$ is an optionally substituted pyridine, pyrimidine, or pyrazine ring or an optionally substituted pyridine-2-one ring form an aspect of the invention.

Terminology

As used herein, the term "$(C_a$-$C_b)$alkyl" wherein a and b are integers refers to a straight or branched chain alkyl radical having from a to b carbon atoms. Thus when a is 1 and b is 6, for example, the term includes methyl, ethyl, n-propyl, iso-propyl, n-butyl, isobutyl, sec-butyl, t-butyl, n-pentyl and n-hexyl.

As used herein the term "divalent $(C_a$-$C_b)$alkylene radical" wherein a and b are integers refers to a saturated hydrocarbon chain having from a to b carbon atoms and two unsatisfied valences. The term includes, for example, methylene, ethylene, n-propylene and n-butylene.

As used herein the term "$(C_a$-$C_b)$alkenyl" wherein a and b are integers refers to a straight or branched chain alkenyl moiety having from a to b carbon atoms having at least one double bond of either E or Z stereochemistry where applicable. The term includes, for example, vinyl, allyl, 1- and 2-butenyl and 2-methyl-2-propenyl.

As used herein the term "divalent $(C_a$-$C_b)$alkenylene radical" means a hydrocarbon chain having from a to b carbon atoms, at least one double bond, and two unsatisfied valences. The term includes, for example, —CH=CH— (vinylene), —CH=CH—CH$_2$—, —CH$_2$—CH=CH—, —CH=CH—CH$_2$—CH$_2$—, —CH=CH—CH$_2$—CH$_2$—CH$_2$—, —CH=CH—CH=CH—, —CH=CH—CH=CH—CH$_2$—, —CH=CH—CH=CH—CH$_2$—CH$_2$—, —CH=CH—CH$_2$—CH=CH—, and —CH=CH—CH$_2$—CH$_2$—CH=CH—.

As used herein the term "$C_a$-$C_b$ alkynyl" wherein a and b are integers refers to straight chain or branched chain hydrocarbon groups having from a to b carbon atoms and having in addition at least one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent $(C_a$-$C_b)$alkynylene radical" wherein a and b are integers refers to a divalent hydrocarbon chain having from a to b carbon atoms, and at least one triple bond. The term includes, for example, —C≡C—, —C≡C—CH$_2$—, and —CH$_2$—C≡CH—.

As used herein the term "carbocyclic" refers to a mono-, bi- or tricyclic radical having up to 16 ring atoms, all of which are carbon, and includes aryl and cycloalkyl.

As used herein the term "cycloalkyl" refers to a monocyclic saturated carbocyclic radical having from 3-8 carbon atoms and includes, for example, cyclopropyl, cyclobutyl, cyclopentyl, cyclohexyl, cycloheptyl. cyclooctyl and bicyclo [2.2.1]hept-1-yl.

As used herein the unqualified term "aryl" refers to a mono-, bi- or tri-cyclic carbocyclic aromatic radical, and includes radicals having two monocyclic carbocyclic aromatic rings which are directly linked by a covalent bond. Illustrative of such radicals are phenyl, biphenyl and naphthyl.

As used herein the unqualified term "heteroaryl" refers to a mono-, bi- or tri-cyclic aromatic radical containing one or more heteroatoms selected from S, N and O, and includes radicals having two such monocyclic rings, or one such monocyclic ring and one monocyclic aryl ring, which are directly linked by a covalent bond. Illustrative of such radicals are thienyl, benzothienyl, furyl, benzfuryl, pyrrolyl, imidazolyl, benzimidazolyl, thiazolyl, benzothiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in its non-aromatic meaning relates to a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are azetidinyl, pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with up to four compatible substituents, each of which independently may be, for example, $(C_1$-$C_6)$ alkyl, $(C_2$-$C_6)$alkenyl, $(C_2$-$C_6)$alkynyl, $(C_1$-$C_6)$alkoxy, hydroxy, hydroxy$(C_1$-$C_6)$alkyl, $(C_1$-$C_3)$alkoxy$(C_1$-$C_3)$alkyl, mercapto, mercapto$(C_1$-$C_6)$alkyl, $(C_1$-$C_6)$alkylthio, halo (including fluoro, bromo and chloro), fully or partially fluorinated $(C_1$-$C_3)$alkyl, $(C_1$-$C_3)$alkoxy or $(C_1$-$C_3)$alkylthio such as trifluoromethyl, trifluoromethoxy, and trifluoromethylthio, nitro, nitrile (—CN), oxo (=O), phenyl, phenyl$(C_1$-$C_3)$ alkyl-, phenoxy, monocyclic heteroaryl, heteroaryl($C_1$-$C_3$) alkyl-, or heteroaryloxy with 5 or 6 ring atoms, cycloalkyl having 3 to 6 ring carbon atoms, —$COOR^A$, —$COR^A$, —$OCOR^A$, —$SO_2R^A$, —$CONR^AR^B$, —$CONHNH_2$, —$SO_2NR^AR^B$, —$NR^AR^B$, —$NHNH_2$, —$OCONR^AR^B$, —$NR^BCOR^A$, —$NR^BCOOR^A$, —$NR^BSO_2OR^A$ or —$NR^A$-$CONR^AR^B$ wherein $R^A$ and $R^B$ are independently hydrogen or a ($C_1$-$C_6$)alkyl, hydroxy($C_1$-$C_6$)alkyl, or ($C_1$-$C_3$)alkoxy($C_1$-$C_3$)alkyl group or, in the case where $R^A$ and $R^B$ are linked to the same N atom, $R^A$ and $R^B$ taken together with that nitrogen may form a cyclic amino ring such as morpholinyl, piperidinyl. piperazinyl, or 4-($C_1$-$C_6$)alkyl-piperizinyl such as 4-methyl-piperazinyl. Where the substituent is phenyl, phenyl($C_1$-$C_3$)alkyl-, phenoxy or monocyclic heteroaryl, heteroaryl($C_1$-$C_3$)alkyl-, or heteroaryloxy with 5 or 6 ring atoms, the phenyl or heteroaryl ring thereof may itself be substituted by any of the above substituents except phenyl, phenyl($C_1$-$C_3$)alkyl-, phenoxy, heteroaryl, heteroaryl($C_1$-$C_3$)alkyl-, or heteroaryloxy. An "optional substituent" or "substituent" may be one of the foregoing specified groups.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris (hydroxymethyl)amino-methane, L-arginine, L-lysine, N-ethyl piperidine, dibenzylamine and the like. Those compounds (I) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesunfonic, glutamic, lactic, and mandelic acids and the like. For a review on suitable salts, see *Handbook of Pharmaceutical Salts: Properties, Selection, and Use* by Stahl and Wermuth (Wiley-VCH, Weinheim, Germany, 2002).

The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Compounds of the invention that contain one or more actual or potential chiral centres, because of the presence of asymmetric carbon atoms, can exist as a number of diastereoisomers with R or S stereochemistry at each chiral centre. The invention includes all such diastereoisomers and mixtures thereof.

Structural Features

The compounds with which the invention is concerned may have, for example, the following features, in any compatible combination:

Z is N or CH, or CF. Presently it is preferred that Z be CH, so that the compounds (I) are substituted benzothiazoles.

X may be, for example, —C(O)O— or —C(O)NH—. Within this subclass, m may be 0 and Q may be, for example, hydrogen, cyclopropyl, cyclobutyl, cyclopentyl or cyclohexyl. Also within this subclass, m may be 1 and Q hydrogen, with Alk being, for example —$CH_2$—, —$(CH_2)_2$— or —$(CH_2)_3$—. Presently, when m is 1 it is preferred that X be —C(O)NH—, Alk be —$(CH_2)_2$— and Q be hydrogen.

$R_3$ is a group $Q^4$-[$Alk^2$]$_p$-[$Q^3$]$_q$— other than hydrogen. In some embodiments q is 1 and p is 0 or 1. In other embodiments, q is 0 and p is 0 or 1.

$Alk^2$ when present (ie p is 1) is an optionally substituted divalent $C_1$-$C_6$ alkylene or $C_2$-$C_6$ alkenylene or $C_2$-$C_6$ alkynylene radical, for example optionally substituted —$CH_2$—, —CH(OH)—, —$CH_2CH_2$—, —$CH_2CH_2CH_2$—, —CH═CH—, —C≡C—, —$CH_2$CH═CH—, —$CH_2$C≡C—. Presently preferred are optionally substituted divalent $C_1$-$C_3$ alkylene radicals $Q^3$ when present is an optionally substituted divalent monocyclic carbocyclic radical, or an optionally substituted heterocyclic radical having 5 or 6 ring atoms, or an optionally substituted divalent bicyclic carbocyclic or heterocyclic radical having 9 or 10 ring atoms. Examples of such radicals include those having optionally substituted thienyl, benzothienyl, furyl, benzfuryl, pyrrolyl, imidazolyl, benzimidazolyl, thiazolyl, benzothiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl, indazolyl. azetidinyl, pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, piperidinyl, piperazinyl, indolyl, morpholinyl, benzfuranyl, pyranyl, isoxazolyl, benzimidazolyl, cyclopropyl, cyclobutyl, cyclopentyl, cyclohexyl, phenyl, and naphthyl rings.

$Q^4$ is hydrogen, an optional substituent, or optionally substituted carbocyclic or heterocyclic ring having 3-7 ring atoms. Optional substituents include those particularised above in the discussion of the term "optional substituent". Carbocyclic or heterocyclic rings having 3-7 ring atoms include those monocyclic rings listed in the preceding paragraph, as well as cyclopentyl and homopiperazinyl rings.

Presently it is preferred that $Q^3$ be present (ie q is 1), and in such cases $Q^3$ may be, for example, an optionally substituted pyridine ring, an optionally substituted pyrimidine ring or an optionally substituted pyrazine ring, such as an optionally substituted pyridine-2-yl ring, an optionally substituted pyrimidine-2-yl ring or an optionally substituted pyrazine-2-yl ring. Optional substituents in $Q^3$ include $CH_3O$—, —$NH_2$, —CN, Cl, $CH_3$—, and —$CF_3$.

In embodiments wherein p and q are each 0, $Q^4$ may be one of the optional substituents particularised above, for example, halo such as chloro or bromo, —$CONHR^A$, —$NHCONHR^B$, wherein $R^A$ and $R^B$ are hydrogen or a ($C_1$-$C_6$)alkyl, hydroxy ($C_1$-$C_6$)alkyl, or ($C_1$-$C_3$)alkoxy($C_1$-$C_3$)alkyl group.

Currently preferred $R_3$ groups include the following:

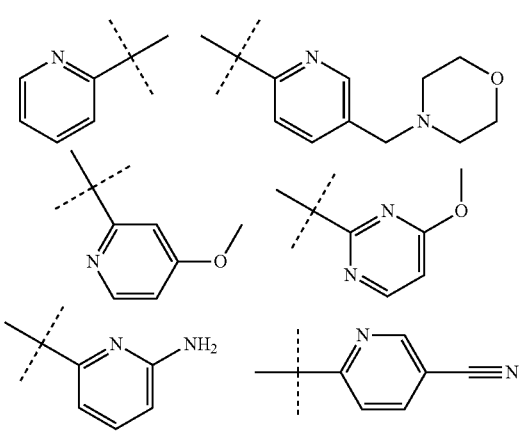

-continued

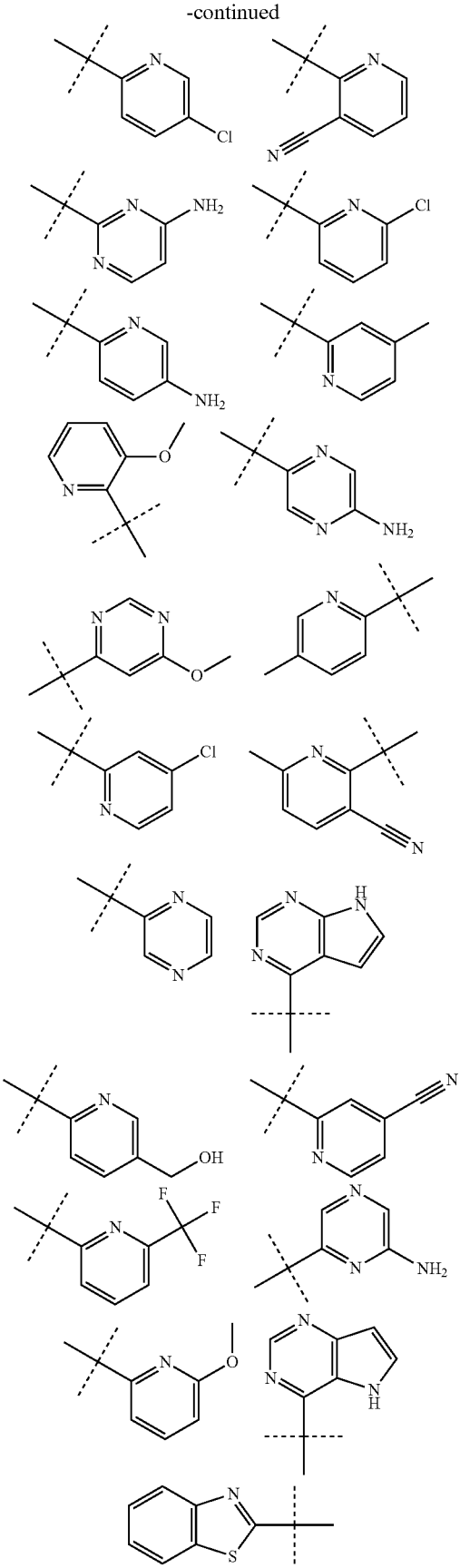

$R_2$ is a group $Q^1$-[$Alk^1$]$_q$-$Q^2$-.

$Alk^1$ when present is an optionally substituted, divalent, straight chain or branched $C_1$-$C_6$ alkylene, or $C_2$-$C_6$ alkenylene or $C_2$-$C_6$ alkynylene radical which may contain or terminate in an ether (—O—), thioether (—S—) or amino (—NR)— link. Examples of such radicals include —$CH_2$—, —CH(OH)—, —$CH_2CH_2$—, —$CH_2CH_2CH_2$—, —CH=CH—, —C≡C—, —$CH_2$CH=CH—, —$CH_2$C≡C—, —$CH_2$NH—, —C(=O)NH—, —$CH_2OCH_2$—, —$CH_2CH_2$C(=O)NH—.

$Q^2$ is an optionally substituted divalent monocyclic carbocyclic or heterocyclic radical having 5 or 6 ring atoms or an optionally substituted divalent bicyclic carbocyclic or heterocyclic radical having 9 or 10 ring atoms. Examples of such radicals include those specified above in the discussion of radical $Q^3$.

$Q^1$ is hydrogen, an optional substituent, or an optionally substituted carbocyclic or heterocyclic radical having 3-7 ring atoms. Examples of such radicals include those specified above in the discussion of radical $Q^4$.

In the group $R_2$, $Q^2$ may be an optionally substituted divalent nitrogen-containing heterocyclic radical having 5 or 6 ring atoms, such as an optionally substituted divalent pyridonyl, pyridyl, pyrazolyl, pyrimidinyl, thiazolyl, or pyrrolyl radical, or $Q_2$ when present may be a divalent nitrogen-containing bicyclic carbocyclic or heterocyclic radical having 9 or 10 ring atoms, such as quinolinyl, isoquinolinyl, benzimidazolyl or 5-azaindolyl. Presently preferred $Q^2$ rings include optionally substituted pyridine, pyrimidine, pyrazine or pyridine-2-one rings, such as an optionally substituted pyridine-3-yl ring, an optionally substituted pyrimidine-5-yl ring, an optionally substituted pyrazine-2-yl ring or an optionally substituted pyridine-2-one-4-yl ring. Presently preferred optional substituents in $Q^2$ include $CH_3$—, $CH_3O$—, —CN, and —$NH_2$.

In the group $R_2$, q is 0 or 1. When q is 1, $Alk^1$ is present and may be, for example, an optionally substituted divalent $C_1$-$C_3$ alkylene radical which may optionally include an —NH— link, or optionally terminate in an —NH— link to $Q^2$. In a particular case, $Alk^1$ is a divalent $C_2$-$C_3$ alkylene radical which terminates in an —NH— link to $Q^2$, and which is oxo-substituted on the C atom adjacent that —NH— link, whereby $Alk^1$ has the formula —($CH_2$)$_{0-2}$C(=O)NH—. In other cases $Alk^1$ has the formula —($CH_2$)$_{1-2}$NHC(=O)—, with the (C=O) being linked to $Q^2$.

In the group $R_2$, $Q^1$ may be, for example, hydrogen, or an optional substituent as particularised above. In some embodiments $Q^1$ is a group of formula —$NR^AR^B$, wherein $R^A$ and $R^B$ are independently hydrogen or a ($C_1$-$C_6$)alkyl, hydroxy($C_1$-$C_6$)alkyl, or ($C_1$-$C_3$)alkoxy($C_1$-$C_3$)alkyl group, or $R^A$ and $R^B$ taken together with that nitrogen form a cyclic amino ring, for example, a piperidine, morpholine, thiomorpholine, azetidine, pyrrolidine or piperazine ring, the latter being optionally N-substituted by $C_1$-$C_3$ alkyl.

Currently preferred $R_2$ groups include the following:

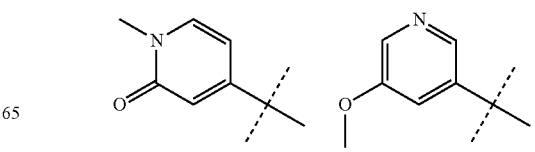

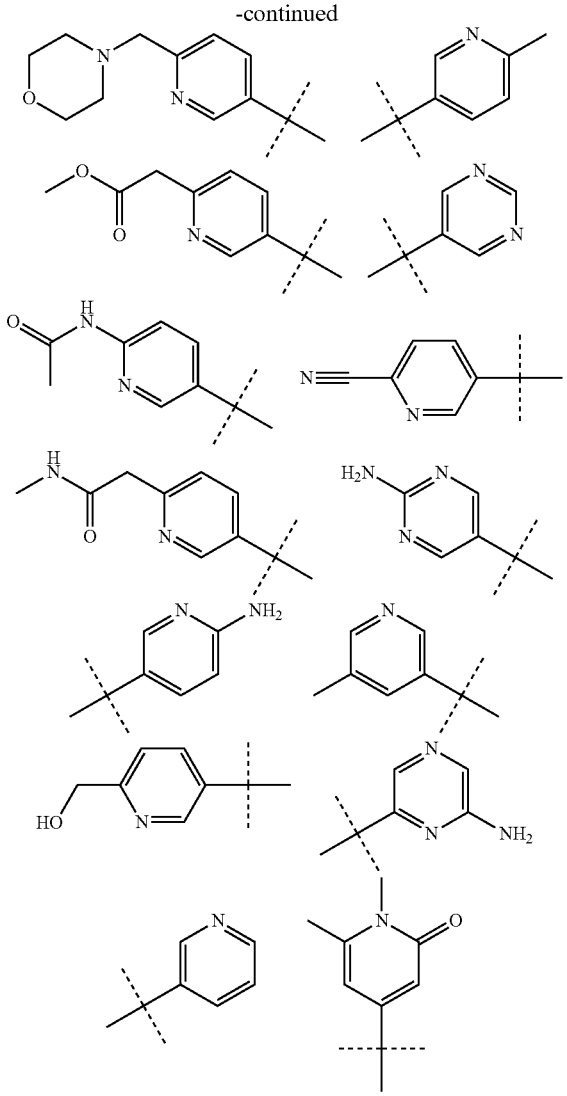

Utilities and Compositions

As mentioned above, the compounds with which the invention are concerned are antimicrobially active, and may therefore be of use as topical antibacterial disinfectants, or in the treatment of microbial infection in humans and non-human animals e.g. other mammals, birds and fish. Since the type II topoisomerase target of the compounds of the invention is a universal bacterial enzyme, the compounds of the invention inhibit growth of a variety of bacterial species, of the Gram-positive and/or Gram negative classes and atypical bacteria, such as staphylococci, enterococci, streptococci, haemophili, moraxellas, chlamydophilas, legionellas and mycoplasmas for example *Staphylococcus aureus, Staphylococcus epidermidis, Enterococcus faecalis, Enterococcus faecium, Streptococcus pneumoniae, Streptococcus pyogenes, Haemophilus influenzae, Moraxella catarrhalis, Chlamydophila pneumonia, Legionella pneumophila* and *Mycoplasma pneumoniae*. The compounds with which the invention is concerned are therefore useful for the treatment of bacterial infection or contamination, for example in the treatment of, inter alia, Gram-positive infections and community acquired pneumonias.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy. Optimum dose levels and frequency of dosing will be determined by clinical trial as is required in the art.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

Synthesis and Example Compounds

There are multiple synthetic strategies for the synthesis of the compounds (I) with which the present invention is concerned, but all rely on known chemistry, known to the synthetic organic chemist. Thus, compounds according to formula (I) can be synthesised according to procedures described in the standard literature and are well-known to the one skilled in the art. Typical literature sources are "*Advanced organic chemistry*", 4th Edition (Wiley), J March, "*Comprehensive Organic Transformation*", 2nd Edition (Wiley), R. C. Larock, "*Handbook of Heterocyclic Chemistry*", 2nd Edition (Pergamon), A. R. Katritzky), review articles such as found in "*Synthesis*", "*Acc. Chem. Res.*", "*Chem. Rev*", or primary literature sources identified by standard literature searches online or from secondary sources such as "*Chemical Abstracts*" or "*Beilstein*".

Examples of synthetic approaches and schemes for the preparation of compounds (I) are given in the Examples herein.

The invention will now be illustrated by reference to the following Examples:

Abbreviations
DMF—N,N-dimethylformamide
DMSO—dimethylsulfoxide
HPLC-MS—high performance liquid chromatography-mass spectrometry
NMR—nuclear magnetic resonance
Rt—retention time
THF—tetrahydrofuran Step 1. 4-Bromo-2-iodo-6-nitroaniline 4-Bromo-2-nitroaniline (14.3 g, 0.0659 mol) was added in one portion to iodine (17.6 g, 0.0692 mol) dissolved in ethanol (300 ml), followed by silver (I) sulphate (20.4 g 0.0659 mol). After stirring at ambient temperature for 18 hours the reaction was filtered and the solid obtained was washed with dichloromethane until all the orange product had dissolved. The combined filtrates were evaporated in vacuo and the resulting solid was washed with diethyl ether/40-60 Petroleum ether (1:1) and filtered to give 4-bromo-2-iodo-6-nitroaniline as an orange solid (19.8 g, 88%), which was used without further purification.

$^1$H NMR (400 MHz, δ, CDCl$_3$): 6.15 (2H, br s), 8.00 (1H, s), 8.42 (1H, s).

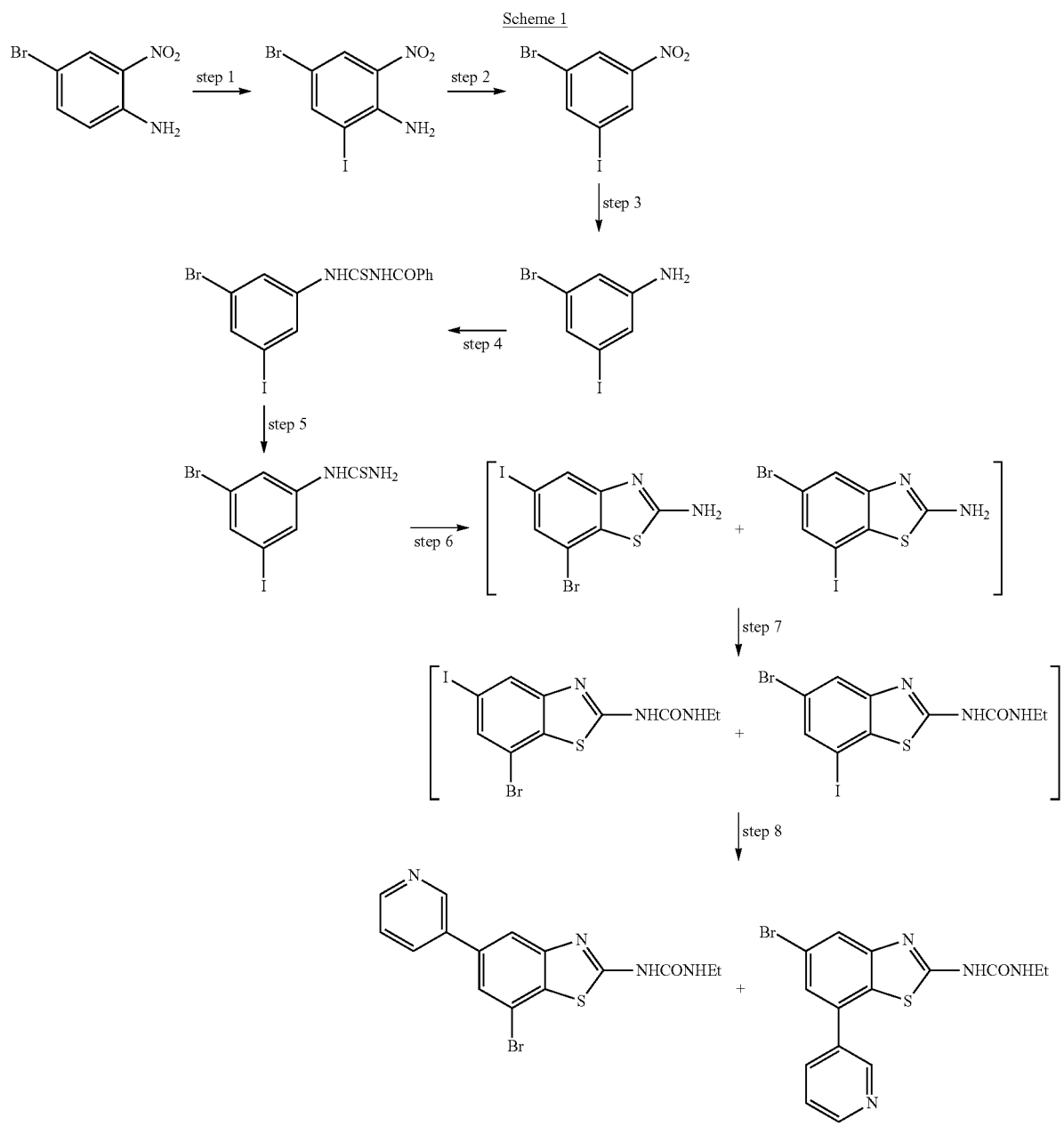

Step 2. 3-Bromo-5-iodonitrobenzene 4-bromo-2-iodo-6-nitroaniline (5 g, 0.0145 mol) was added in portions to stirred concentrated sulfuric acid (60 ml) keeping the temperature at 0-5° C. After stirring in the cold for 1 h, sodium nitrite (2.3 g, 0.0326 mol) was added and the reaction mixture stirred in the cold for a further 2 h. The reaction mixture was then poured into ice (250 ml). The resultant mixture was added, in portions, to a boiling solution of copper (II) sulfate (0.36 g, 0.00145 mol) in ethanol (150 ml) and boiled for a further 2 h. The reaction mixture was cooled to ambient temperature and extracted with ethyl acetate (300 ml) which was washed with saturated sodium hydrogen carbonate solution (250 ml) and dried (MgSO$_4$). The solvent was removed in vacuo to give 3-Bromo-5-iodonitrobenzene as a yellow solid (4.21 g, 88%) which was used without further purification.

$^1$H NMR (400 MHz, δ, CDCl$_3$): 8.18 (1H, s), 8.34 (1H, s), 8.50 (1H, s)

Step 3. 3-Bromo-5-iodoaniline

A mixture of 3-Bromo-5-iodonitrobenzene (4.21 g, 0.0128 mol) and iron powder (3.6 g, 0.0642 mol) in glacial acetic acid (50 ml) was stirred at ambient temperature for 16 h. The reaction mixture was then filtered through a pad of celite and washed through with ethyl acetate. The filtrate was evaporated in vacuo to give a brown oil. This was re-dissolved in ethyl acetate, loaded onto a large pad of silica and eluted with ethyl acetate. The filtrate was evaporated in vacuo to afford 3-Bromo-5-iodoaniline as a brown solid (3.67 g, 96%) which was used without further purification.

$^1$H NMR (400 MHz, δ, CDCl$_3$): 3.72 (2H, br s), 6.77 (1H, s), 6.95 (1H, s), 7.21 (1H, s).

Step 4. 1-Benzoyl-3-(3-bromo-5-iodophenyl)-thiourea

A solution of ammonium thiocyanate (4.45 g, 0.0585 mol) in anhydrous acetone (48 ml) was treated dropwise with benzoyl chloride (6.47 ml, 0.05583 mol) and stirred at ambient temperature for 1 h. A solution of 3-Bromo-5-iodoaniline (15.85 g, 0.05319 mol) in anhydrous acetone (48 ml) was then added in one portion and the mixture stirred at ambient temperature for 16 h. The resultant suspension was poured into water (300 ml) and stirred for 0.5 h. The precipitated solid was collected by filtration washed with water followed by 40-60° petroleum ether and dried in vacuo to afford 1-Benzoyl-3-(3-bromo-5-iodo-phenyl)-thiourea (20.70 g, 84%).

$^1$H NMR (400 MHz, δ, CDCl$_3$): 7.56 (2H, m), 7.67 (1H, m), 7.76 (1H, s), 7.90 (2H, d), 7.99 (1H, s), 8.05 (1H, s), 9.17 (1H, br s), 12.70 (1H, br s).

Step 5. (3-Bromo-5-iodo-phenyl)-thiourea

A stirred suspension of 1-Benzoyl-3-(3-bromo-5-iodophenyl)-thiourea (20.70 g, 0.0449 mol) in methanol (303 ml) was treated with sodium methoxide (2.42 g, 0.0449 mol) and stirred at ambient temperature for 4 h. The resultant suspension was evaporated to dryness at reduced pressure. The residue was mixed with water (500 ml) and extracted with ethyl acetate (3×200 ml) which was dried (MgSO$_4$) and the solvent removed in vacuo to give a residue which was triturated with 40-60° petroleum ether/diethyl ether (1:1) to afford (3-Bromo-5-iodophenyl)-thiourea as an off-white solid (14.35 g, 89%).

$^1$H NMR (400 MHz, δ, D$_6$DMSO): 7.67 (1H, s), 7.83 (1H, s), 7.89 (1H, s), 9.87 (1H, br s).

Step 6. 7-Bromo-5-iodo-benzothiazol-2-ylamine and 5-Bromo-7-iodo-benzothiazol-2-ylamine A stirred suspension of (3-Bromo-5-iodo-phenyl)-thiourea (2.83 g, 0.00723 mol) in chloroform (65 ml) was treated with bromine (1.16 g, 0.4 ml, 0.00723 mol) and boiled under reflux for 5 h. After cooling to ambient temperature, the mixture was diluted with ether (200 ml). The solid material was collected by filtration, washed with aqueous sodium hydrogen carbonate solution (200 ml) followed by water (200 ml) and dried in vacuo to give a 1:1 mixture of 7-Bromo-5-iodo-benzothiazol-2-ylamine and 5-Bromo-7-iodo-benzothiazol-2-ylamine (2.87 g, 100%) which was used without further purification.

$^1$H NMR (400 MHz, δ, D$_6$DMSO): 3.40 (2H, br s), 7.50-7.95 (2H, m).

Step 7. 1-(7-Bromo-5-iodo-benzothiazol-2-yl)-3-ethyl-urea and 1-(5-Bromo-7-iodo-benzothiazol-2-yl)-3-ethyl-urea A stirred mixture of the product from Step 6 (2.87 g, 0.00808 mol), anhydrous 1,4-dioxane (95 ml), ethyl isocyanate (2.87 g, 3.2 ml, 0.0404 mol) and dibutyltindiacetate (0.2 ml) was heated at 100° C. for 16 h. After cooling to ambient temperature, the reaction mixture was evaporated to dryness and the residue triturated with diethyl ether (250 ml). The solid material was collected by filtration and dried in vacuo to give a 1:1 mixture of 1-(7-Bromo-5-iodo-benzothiazol-2-yl)-3-ethyl-urea and 1-(5-Bromo-7-iodo-benzothiazol-2-yl)-3-ethyl-urea as a white solid (2.17 g, 63%) which was used without further purification.

$^1$H NMR (400 MHz, δ, D$_6$DMSO): 1.12 (3H, m), 3.23 (2H, m), 6.77 (1H, br t), 7.72-8.00 (2H, m).

Step 8. 1-(5-Bromo-7-pyridin-3-yl-benzothiazol-2-yl)-3-ethyl-urea [Example 2] and 1-(7-Bromo-5-pyridin-3-yl-benzothiazol-2-yl)-3-ethyl-urea. [Example 3]

A stirred mixture of the product from Step 7 (3.66 g, 0.00859 mol), 3-pyridineboronic acid (1.06 g, 0.00859 mol), powdered potassium phosphate tribasic (2.18 g, 0.0103 mol), anhydrous 1,4-dioxane (58 ml) and anhydrous methanol (117 ml) was purged with nitrogen for 15 min. 1,1'-bis(diphenylphosphino)ferrocene palladium (II) chloride complex (0.70 g, 0.000859 mol) was added and the mixture heated at 80° C. for 16 h under an atmosphere of nitrogen. After cooling to ambient temperature, the mixture was filtered through celite and washed through with methanol. The filtrate was evaporated in vacuo and the resultant residue was purified by "flash" silica chromatography using ethyl acetate to elute 1-(5-Bromo-7-pyridin-3-yl-benzothiazol-2-yl)-3-ethyl-urea (1.0 g, 30%) and 5% methanol in ethyl acetate to elute 1-(7-Bromo-5-pyridin-3-yl-benzothiazol-2-yl)-3-ethyl-urea (0.857 g, 26%).

1-(5-Bromo-7-pyridin-3-yl-benzothiazol-2-yl)-3-ethyl-urea: $^1$H NMR (400 MHz, δ, D$_6$DMSO): 1.10 (3H, t), 3.20 (2H, m), 6.76 (1H, br t), 7.56 (1H, s), 7.62 (1H, m), 7.90 (1H, s), 8.17 (1H, d), 8.71 (1H, d), 8.92 (1H, s).

1-(7-Bromo-5-pyridin-3-yl-benzothiazol-2-yl)-3-ethyl-urea: $^1$H NMR (400 MHz, δ, D$_6$DMSO): 1.15 (3H, t), 3.23 (2H, m), 6.78 (1H, br t), 7.53 (1H, m), 7.81 (1H, s), 8.00 (1H, s), 8.20 (1H, d), 8.62 (1H, d), 9.00 (1H, s).

LC-MS m/z 377 [M+H]$^+$ Rt=2.63 min.

The following were prepared similarly:

| ID | NAME | LC-MS DATA |
|---|---|---|
| Example 1 | 1-[7-(6-Amino-pyridin-3-yl)-5-bromo-benzothiazol-2-yl]-3-ethyl-urea | m/z 392[M + H]$^+$<br>Rt = 2.22 min. |
| | 1-[5-(2-Amino-pyrimidin-5-yl)-7-bromo-benzothiazol-2-yl]-3-ethyl-urea | m/z 395[M + H]$^+$<br>Rt = 2.91 min. |
| | 1-[7-(2-Amino-pyrimidin-5-yl)-5-bromo-benzothiazol-2-yl]-3-ethyl-urea | m/z 395[M + H]$^+$<br>Rt = 2.90 min. |

Scheme 1A

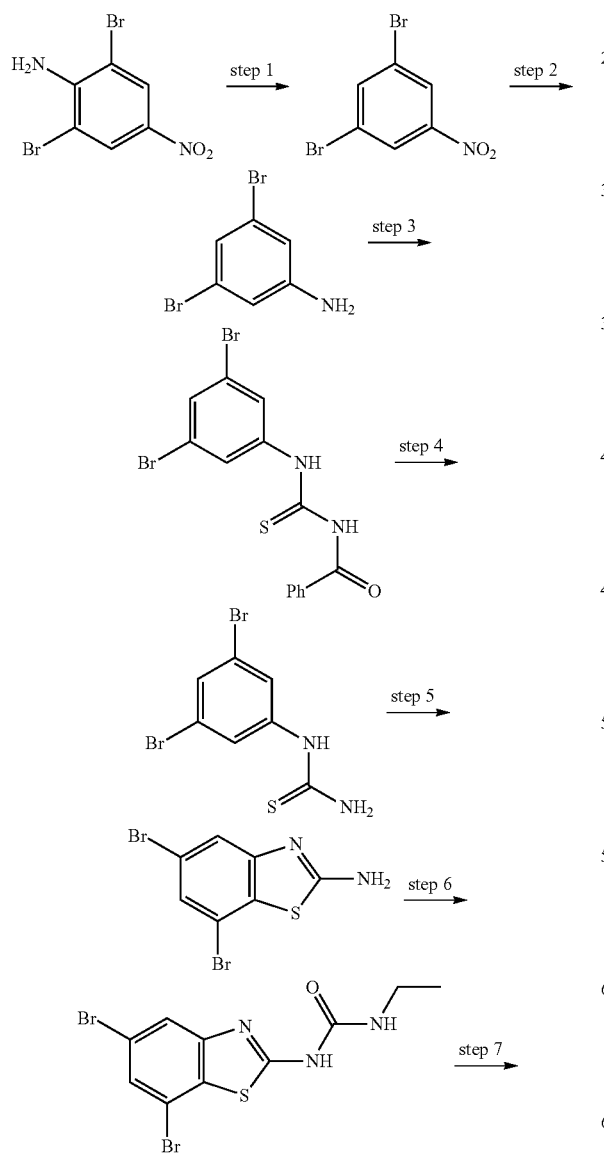

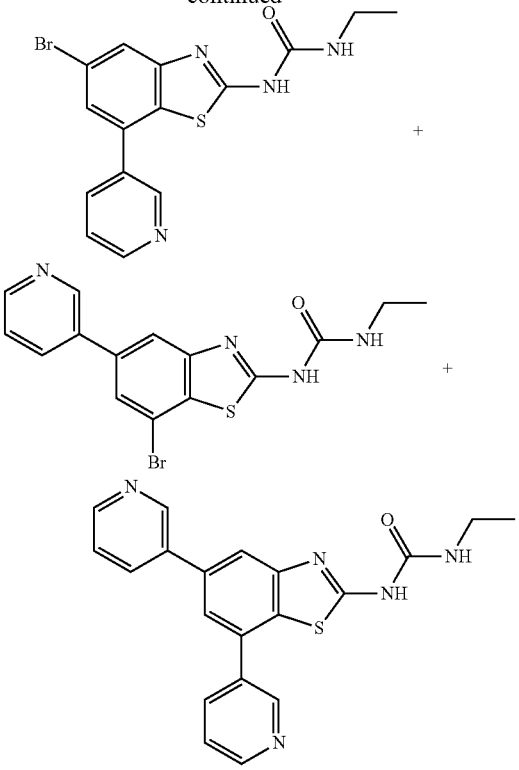

Step 1. 1,3-Dibromo-5-nitro-benzene

To an ice-cold solution of 2,6-dibromo-4-nitro-aniline (100 g, 0.34 mol) in 1.50 L of ethanol was added dropwise conc. $H_2SO_4$ (116 ml, 2.15 mol) over 30-45 min with constant stirring. The reaction mixture was heated to 60° C. and sodium nitrite (72 g, 1.09 mol) was added to the reaction mixture portion wise. The resulting yellow colored reaction mixture was heated slowly to 90° C. and refluxed for 2 to 2.5 h. After cooling to room temperature, the mixture was poured into ice water. The reddish brown solid thus obtained was filtered, washed with water and dried to give the desired compound as a brown solid (85.0 g, 90%).
$^1$H-NMR (400 MHz, DMSO-d$_6$): δ 8.38 (d, J=1.20 Hz, 1H) and 8.40 Hz, br s, 2H)

Step 2. 3,5-Dibromoaniline

To a solution of 1,3-dibromo-5-nitro-benzene (85.0 g, 0.30 mol) in 1 L of ethanol was added $SnCl_2.2H_2O$ (341.0 g, 1.50 mol) portion wise at room temperature. The reaction mixture was heated under reflux at 80° C. for 1.5 h. After cooling to room temperature, the solvent was evaporated under reduced pressure and the crude white solid thus obtained was basified with 4N NaOH solution to pH 12. The mixture was extracted with ethyl acetate (×3) and the combined organic layer was washed with brine solution and dried over $Na_2SO_4$. The solvent was removed under reduced pressure, to give the desired compound as a brown solid (65.0 g, 86%).
$^1$H-NMR (400 MHz, DMSO-d$_6$): δ 5.71 (br s, 2H), 6.71 (s, 2H) and 6.77 (s, 1H).

Step 3. 1-Benzoyl-3-(3,5-dibromo-phenyl)-thiourea

To the solution of 3,5-dibromoaniline (65.0 g, 0.26 mol) in anhydrous acetone (1.6 L) was added benzoylisothiocyanate (46.4 g, 0.28 mol) and the reaction mixture was stirred at room temperature for 30 min. Acetone was distilled off and the crude residue was washed with hexane to obtain desired compound as yellow solid (96.5 g, 90%).

$^1$H-NMR (400 MHz, DMSO-d$_6$): δ 7.56 (t, J=7.60 Hz, 2H), 7.67 (t, J=7.20 Hz, 1H), 7.75 (s, 1H), 7.96-7.98 (m, 4H), 11.76 (br s, 1H) and 12.54 (br s, 1H).

Step 4. (3,5-Dibromo-phenyl)-thiourea

A solution of NaOH (46.30 g, 1.16 mol) dissolved in 480 mL of H$_2$O was added to a solution of 1-benzoyl-3-(3,5-dibromo-phenyl)-thiourea (96.0 g, 0.23 mol) in 1.20 L of THF. The resulting reaction mixture was stirred at 70° C. for 12 hours. THF was distilled off and extracted with ethyl acetate (×3). The combined organic layer was dried over Na$_2$SO$_4$, filtered and distilled off to get the crude residue that was washed with hexane to obtain the desired compound as a grey solid (68 g, 95%).

$^1$H-NMR (400 MHz, DMSO-d$_6$): δ 7.49 (s, 1H), 7.84 (s, 2H), 7.98 (br s, 2H) and 10.48 (br s, 1H). MS: 310.88 (M+H)$^+$.

Step 5. 5,7-Dibromo-benzothiazol-2-ylamine

To a solution of (3,5-dibromo-phenyl)-thiourea (35 g, 0.11 mol) in CHCl$_3$ (600 mL) at −55-60° C. was added dropwise a solution of Br$_2$ (40.40 g, 0.25 mol, in 100 ml of CHCl$_3$) over a period of 1 h. The reaction mixture was stirred at −55-60° C. for 15 min followed by refluxing at 70-75° C. for 3 h. The reaction mixture was cooled to room temperature and filtered to get the crude residue that was washed with hexane and diethyl ether. The solid thus obtained was dissolved in H$_2$O, basified with aqueous ammonia solution to pH 10-12 and stirred for 30 min. The solid thus obtained was filtered and washed with water to get the desired product (34.0 g, 98%).

$^1$H-NMR (400 MHz, DMSO-d$_6$): δ 7.39 (s, 1H), 7.48 (s, 1H) and 7.95 (br s, 2H). MS: 308.96 (M+H)$^+$.

Step 6. 1-(5,7-Dibromo-benzothiazol-2-yl)-3-ethyl-urea

To a solution of 5,7-dibromo-benzothiazol-2-ylamine (20.0 g, 0.65 mol) in dioxane (400 mL) was added ethylisocyante (27.83 g, 0.39 mol) and the reaction mixture was stirred at 75-80° C. for 15 h. After the completion of the reaction (TLC monitoring) the solvent was evaporated and the residue was taken in H$_2$O and stirred at 70-75° C. for 15 h. The solid was filtered and washed with hot water and dried under high vacuum to get the desired product (19.65 g, 80%).

$^1$H-NMR (400 MHz, DMSO-d$_6$): δ 1.08 (t, J=6.80 Hz, 3H), 3.18 (m, 2H), 6.76 (br s, 1H), 7.62 (s, 1H), 7.82 (s, 1H) and 11.10 (br s, 1H). MS: 379.90 (M+H)$^+$.

Step 7. 1-(5-Bromo-7-pyridin-3-yl-benzothiazol-2-yl)-3-ethyl-urea. [Example 2] 1-(7-Bromo-5-pyridin-3-yl-benzothiazol-2-yl)-3-ethyl-urea. [Example 3] 1-(5,7-Di-pyridin-3-yl-benzothiazol-2-yl)-3-ethyl-urea. [Example 4]

To a solution of 1-(5,7-dibromo-benzothiazol-2-yl)-3-ethyl-urea (1.60 g, 0.40 mmol) in DMF-H$_2$O (2:1, 48 mL) was added pyridine-3-boronic acid (0.51 g, 0.42 mmol) and K$_3$PO$_4$ (0.90 g, 0.42 mmol) under nitrogen atmosphere at room temperature. The reaction mixture was then degassed for 30 min followed by addition of [1,1′-bis(diphenylphosphino)ferrocene] dichloropalladium(II) complex with CH$_2$Cl$_2$ (0.35 g, 0.042 mmol). The reaction mixture was then again degassed for 30 min and heated at 120° C. for 1 h under nitrogen atmosphere. DMF was distilled off, water was added into reaction mixture and extracted with ethyl acetate (×3). The combined organic layer was dried over anhydrous Na$_2$SO$_4$, and evaporated to dryness under reduced pressure. The compound was purified over silica (230-400 M) using ethyl acetate/hexane (gradient) to provide the desired compounds.

1-(5-Bromo-7-pyridin-3-yl-benzothiazol-2-yl)-3-ethyl-urea. 60% EtOAc-Hexane (14% yield). $^1$H-NMR (400 MHz, DMSO-d$_6$): δ 1.07 (t, J=7.20 Hz, 3H), 3.14 (m, 2H), 6.73 (br s, 1H), 7.52-7.60 (m, 2H), 7.87 (s, 1H), 8.11-8.13 (m, 1H), 8.67-8.69 (m, 1H), 8.89 (m, 1H), and 10.99 (br s, 1H). MS: 378.99 (M+H)$^+$.

1-(7-Bromo-5-pyridin-3-yl-benzothiazol-2-yl)-3-ethyl-urea. 80% EtOAc-Hexane (17% yield), m.p. 345° C. $^1$H NMR (DMSO-d$_6$, 400 MHz): δ 1.11 (t, J=7.20 Hz, 3H), 3.20 (m, 2H), 6.75 (br s, 1H), 7.48-7.51 (m, 1H), 7.63 (s, 1H), 7.79 (s, 1H), 8.18 (m, 1H), 8.60 (m, 1H), 8.97 (s, 1H) and 11.01 (br s, 1H). MS: 377.17 (M+H$^+$).

1-(5,7-Di-pyridin-3-yl-benzothiazol-2-yl)-3-ethyl-urea. 95% EtOAc-MeOH (25% yield). $^1$H NMR (DMSO-d$_6$, 400 MHz): δ 1.08 (t, J=7.20 Hz, 3H), 3.15-3.22 (m, 2H), 6.57 (s, 3H), 6.75 (br s, 1H), 7.49-7.53 (m, 1H), 7.59-7.62 (m, 1H), 7.70 (s, 1H), 8.02 (s, 1H), 8.21-8.26 (m, 2H), 8.34 (s, 1H), 8.59 (d, J=4.8 Hz, 1H), 8.68 (d, J=4.8 Hz, 1H), 9.00 (s, 1H), and 11.0 (br s, 1H). MS: 376.07 (M+H$^+$).

The following were prepared similarly:

| ID | NAME | LC/MS or 1HNMR DATA |
|---|---|---|
| | N-{5-[7-Bromo-2-(3-ethyl-ureido)-benzothiazol-5-yl]-pyridin-2-yl}-acetamide | $^1$H NMR (400 MHz, δ, D$_6$DMSO): 1.14(3H, t), 2.16(3H, s), 3.25(2H, m), 6.78(1H, br s), 7.81(1H, d), 7.98(1H, s), 8.20(2H, m), 8.76(1H, s), 10.66(1H, s), 11.00(1H, br s). |
| | 1-[5-(6-Amino-pyridin-3-yl)-7-bromo-benzothiazol-2-yl]-3-ethyl-urea | m/z 394[M + H]$^+$ Rt = 2.25 min. |
| Example 5 | 1-[5-Bromo-7-(1-methyl-1H-pyrazol-4-yl)-benzothiazol-2-yl]-3-ethyl-urea | (400 MHz, δ, D$_6$DMSO): 1.09 (t, J = 7.2 Hz, 3H), 3.18 (q, J = 7.2 Hz, 2H), 3.94 (s, 3H), 6.74 (br s, 1H), 7.56 (s, 1H), 7.68 (s, 1H), 7.97 (s, 1H), 8.26 (s, 1H), 10.95 (br s, 1H). m/z 380.06 [M + H]$^+$. |
| Example 6 | 1-[7-Bromo-5-(1-methyl-1H-pyrazol-4-yl)-benzothiazol-2-yl]-3-ethyl-urea | (DMSO-d$_6$, 400 MHz): δ 1.09 (t, J = 7.2 Hz, 3H), 3.19 (q, J = 7.6 Hz, 2H), 3.85 (s, 3H), 7.41 (m, 1H), 7.65 (s, 1H), 7.81 (s, 1H), 7.98 (s, 1H), 8.27 (s, 1H) and 10.91 (br s, 1H). m/z 380.07 [M + H]$^+$. |
| Example 7 | 1-[5,7-Bis-(1-methyl-1H-pyrazol-4-yl)-benzothiazol-2-yl]-3-ethyl-urea | (DMSO-d$_6$, 400 MHz): δ 1.09 (t, J = 7.20 Hz, 3H), 3.19 (q, J = 7.2 Hz, 2H), 3.87 (s, 3H), 3.95 (s, 3H), 6.73 (br s, 1H), 7.65 (s, 1H), 7.69 (s, 1H), 7.99 (s, 2H), 8.22 (s, 1H), 8.26 (s, 1H), 10.73 (br s, 1H). m/z 382.20 [M + H]$^+$, |

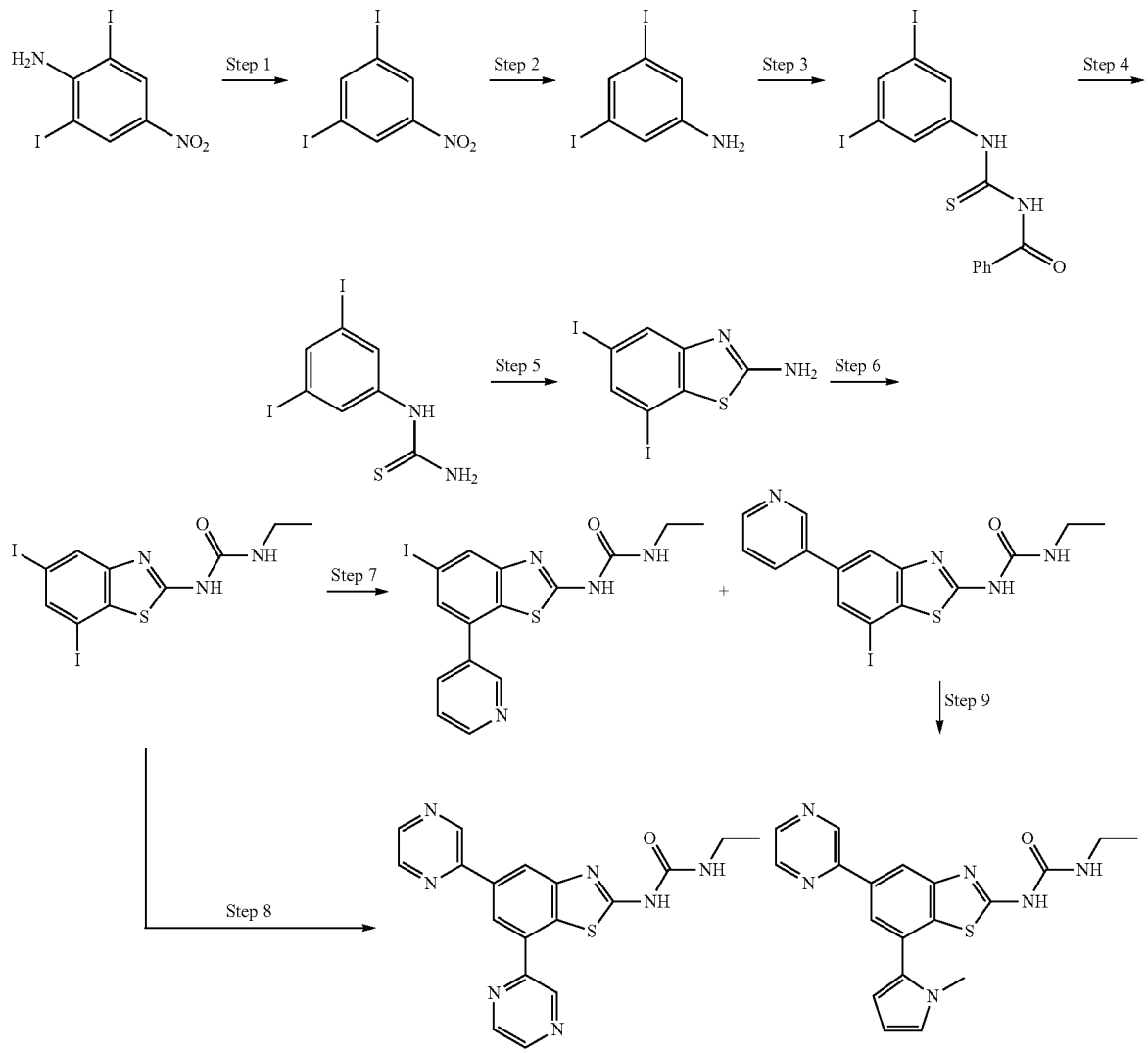

Scheme 1B.

Step 1. 1,3-Diiodo-5-nitro-benzene

To an ice-cold solution of 2,6-diiodo-4-nitro-aniline (25.0 g, 0.06 mol) in ethanol (625 mL) was added dropwise conc. $H_2SO_4$ (50.0 ml, 0.90 mol) over 30-45 min with constant stirring. The reaction mixture was heated to 60° C. and sodium nitrite (9.70 g, 0.14 mol) was added to the reaction mixture portion wise. The resulting yellow colored reaction mixture was heated slowly to 90° C. and refluxed for 2 to 2.5 h. After cooling to room temperature, the mixture was poured into ice water. The reddish brown solid thus obtained was filtered, washed with water and dried to give the desired compound as a yellow solid (17.0 g, 72%).

$^1$H NMR (DMSO-d$_6$, 400 MHz): δ 8.48 (s, 2H) and 8.56 (s, 1H).

Step 2. 3,5-Diiodoaniline

To a solution of 1,3-diiodo-5-nitro-benzene (15.80 g, 0.042 mol) in ethanol (200 mL) was added $SnCl_2.2H_2O$ (28.50 g, 0.13 mol) portion wise at room temperature. The reaction mixture was heated under reflux at 80° C. for 1.5 h. After cooling to room temperature, the solvent was evaporated under reduced pressure and the crude solid thus obtained was basified with 4N NaOH solution to pH 12. The mixture was extracted with ethyl acetate (×3) and the combined organic layer was washed with brine solution and dried over $Na_2SO_4$. The solvent was removed under reduced pressure, to give the desired compound as a yellow solid (11.0 g, 75%).

Step 3. 1-Benzoyl-3-(3,5-diiodo-phenyl)-thiourea

To the solution of 3,5-diiodoaniline (5.0 g, 0.01 mol) in anhydrous acetone (150 mL) was added benzoylisothiocyanate (2.81 g, 0.012 mol) and the reaction mixture was stirred at room temperature for 30 min. Acetone was distilled off and the crude residue was washed with hexane to obtain desired compound as a yellow solid (6.35 g, 91%).

Step 4. (3,5-Diiodo-phenyl)-thiourea

A solution of NaOH (1.30 g, 0.033 mol) dissolved in 35 mL of $H_2O$ was added to a solution of 1-benzoyl-3-(3,5-diiodo-phenyl)-thiourea (6.30 g, 0.013 mol) in 75 mL of THF. The resulting reaction mixture was stirred at 70° C. for 12 hours. THF was distilled off and extracted with ethyl acetate (×3). The combined organic layer was dried over $Na_2SO_4$, filtered and distilled off to get the crude residue that was washed with hexane to obtain the desired compound (4.0 g, 75%).

MS: 405.06 (M+H$^+$).

Step 5. 5,7-Diiodo-benzothiazol-2-ylamine

To a solution of (3,5-diiodo-phenyl)-thiourea (4.0 g, 0.01 mol) in $CHCl_3$ (160 mL) at −55-60° C. was added dropwise a solution of $Br_2$ (4.72 g, 0.02 mol, in 25 ml of $CHCl_3$) over a period of 15 min. The reaction mixture was stirred at −55-60° C. for 15 min followed by refluxing at 70-75° C. for 3 h. The reaction mixture was cooled to room temperature and filtered to get the crude residue that was washed with hexane and diethyl ether. The solid thus obtained was dissolved in $H_2O$, basified with aqueous ammonia solution to pH 10-12 and stirred for 30 min. The solid thus obtained was filtered and washed with water to get the desired product (3.50 g, 88%).

$^1$H NMR (DMSO-$d_6$, 400 MHz): δ 7.59 (d, J=1.0 Hz, 1H), 7.62 (d, J=1.0 Hz, 1H) and 7.85 (br s, 2H). MS: 403.06 (M+H$^+$).

Step 6.
1-(5,7-Diiodo-benzothiazol-2-yl)-3-ethyl-urea

To a solution of 5,7-diiodo-benzothiazol-2-ylamine (8.0 g, 0.02 mol) in dioxane (160 mL) was added ethylisocyante (10.70 g, 0.15 mol) and the reaction mixture was stirred at 75-80° C. for 15 h. After the completion of the reaction (TLC monitoring) the solvent was evaporated and the residue was taken in $H_2O$ and stirred at 70-75° C. for 15 h. The solid was filtered and washed with hot water and dried under high vacuum to get the desired product (5.0 g, 53%).

$^1$H NMR (DMSO-$d_6$, 400 MHz): δ 1.08 (t, J=7.20 Hz, 3H), 3.16-3.19 (m, 2H), 6.73 (br s, 1H), 7.82 (s, 1H), 7.94 (s, 1H) and 10.97 (br s, 1H). MS: 474.12 (M+H$^+$).

Step 7. 1-Ethyl-3-(5-iodo-7-pyridin-3-yl-benzothiazol-2-yl)-urea [Example 8] and 1-Ethyl-3-(7-iodo-5-pyridin-3-yl-benzothiazol-2-yl)-urea [Example 9]

To a solution of 1-(5,7-diiodo-benzothiazol-2-yl)-3-ethyl-urea (0.20 g, 0.42 mmol) in DMF (5 mL) was added pyridine 3-boronic acid (0.076 g, 0.63 mmol) and $K_3PO_4$ (0.133 g, 0.63 mmol) under nitrogen atmosphere at room temperature. The reaction mixture was degassed for half an hour followed by the addition of bis(triphenylphosphine)palladium(II) dichloride (0.0044 g, 0.063 mmol). The reaction mixture was again degassed for half an hour and then heated at 120° C. for 1 h under nitrogen atmosphere. DMF was distilled off, added water and extracted with ethyl acetate (×3). The combined organic layer was dried over anhydrous $Na_2SO_4$, and evaporated to dryness under reduced pressure. The residue was purified by chromatography on silica (230-400 M) using DCM/Methanol (99:1) to provide 1-Ethyl-3-(5-iodo-7-pyridin-3-yl-benzothiazol-2-yl)-urea as an off white solid (0.025 g, 14%) and DCM/Methanol (98:2) to provide 1-Ethyl-3-(7-iodo-5-pyridin-3-yl-benzothiazol-2-yl)-urea as an off white solid (0.025 g, 14%).

1-Ethyl-3-(5-iodo-7-pyridin-3-yl-benzothiazol-2-yl)-urea: $^1$H NMR (DMSO-$d_6$, 400 MHz): δ 1.07 (t, J=7.20 Hz, 3H), 3.16 (m, 2H), 6.76 (br s, 1H), 7.56-7.59 (m, 1H), 7.64 (d, J=8.0 Hz, 1H), 8.03 (s, 1H), 8.11 (dd, J=1.6 and 8.0 Hz, 1H), 8.69 (d, J=4.40 Hz, 1H), 8.88 (s, 1H), 11.01 (br s, 1H). MS: 425.00 (M+H$^+$).

1-Ethyl-3-(7-iodo-5-pyridin-3-yl-benzothiazol-2-yl)-urea: $^1$H NMR (DMSO-$d_6$, 400 MHz): δ 1.09 (t, J=7.20 Hz, 3H), 3.19 (m, 2H), 6.77 (br s, 1H), 7.47-7.50 (m, 1H), 7.88 (s, 1H), 7.94 (s, 1H), 8.12-8.15 (m, 1H), 8.58 (br s, 1H), 8.93 (s, 1H) and 10.96 (br s, 1H). MS: 425.0 (M+H$^+$).

Step 8. 1-(5,7-Di-pyrazin-2-yl-benzothiazol-2-yl)-3-ethyl-urea [Example 10]

To a solution of 1-(5,7-diiodo-benzothiazol-2-yl)-3-ethyl-urea (0.50 g, 1.0 mmol) in DMF (5.0 mL) was added 2-tributylstannyl-pyrazine (0.78 g, 2.0 mmol) under nitrogen atmosphere at room temperature. The reaction mixture was degassed for half an hour followed by the addition of tetrakis(triphenylphosphine)palladium(0) (0.18 g, 0.10 mmol). The reaction mixture was again degassed for half an hour and then heated at 120° C. for 2 h under nitrogen atmosphere. After the completion of the reaction (TLC monitoring), DMF was distilled off, added water and extracted with ethyl acetate (×3). The combined organic layer was dried over anhydrous $Na_2SO_4$, and evaporated to dryness under reduced pressure. The compound was purified by chromatography on silica (230-400 M) using ethyl acetate/Methanol (95:5) to provide the title compound as off white solid (0.025 g, 6.5%).

$^1$H NMR (DMSO-$d_6$, 400 MHz): δ 1.11 (t, J=7.2 Hz, 3H), 3.22 (q, J=8.4 Hz, 2H), 6.79 (br s, 1H), 8.52 (s, 1H), 8.68 (s, 1H), 8.72 (s, 1H), 8.79 (s, 1H), 8.86 (s, 1H), 8.90 (s, 1H), 9.60 (s, 1H), 9.78 (s, 1H) and 10.83 (br s, 1H). MS: 378.18 (M+H$^+$).

Step 9. 1-Ethyl-3-[7-(1-methyl-1H-pyrrol-2-yl)-5-pyridin-3-yl-benzothiazol-2-yl]-urea [Example 11]

To a solution of 1-ethyl-3-(7-iodo-5-pyridin-3-yl-benzothiazol-2-yl)-urea (0.10 g, 0.24 mmol) in DMF (2.0 mL) was added N-methyl-2-tributylstannyl-1H-pyrrole (0.18 g, 0.47 mmol) under nitrogen atmosphere at room temperature. The reaction mixture was degassed for half an hour followed by the addition of tetrakis(triphenylphosphine)palladium(0) (0.027 g, 0.024 mmol). The reaction mixture was again degassed for half an hour and then heated at 120° C. for 20 h under nitrogen atmosphere. After the completion of the reaction (TLC monitoring), DMF was distilled off, added water and extracted with ethyl acetate (×3). The combined organic layer was dried over anhydrous $Na_2SO_4$, and evaporated to dryness under reduced pressure. The crude residue was purified by prep-HPLC to provide the title compound as off white solid (0.005 g, 6.0%).

$^1$H NMR (DMSO-d6, 400 MHz): δ 1.08 (t, J=6.80 Hz, 3H), 3.17 (q, J=6.0 Hz, 2H), 3.68 (s, 3H), 6.19 (s, 1H), 6.41 (m, 1H), 6.77 (br s, 1H), 6.96 (s, 1H), 7.48-7.53 (m, 2H), 7.89 (s, 1H), 8.19 (d, J=8.0 Hz, 1H), 8.59 (m, 1H), 9.00 (s, 1H) and 10.80 (br s, 1H).

MS: 378.15 (M−H$^+$).

Qualitative HPLC Purity (Xbridge C18, 250×4.6 mm, 275 nm): 98.22% (Rt=14.25 min).

Scheme 1C

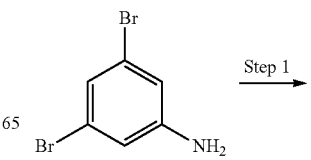

Step 1

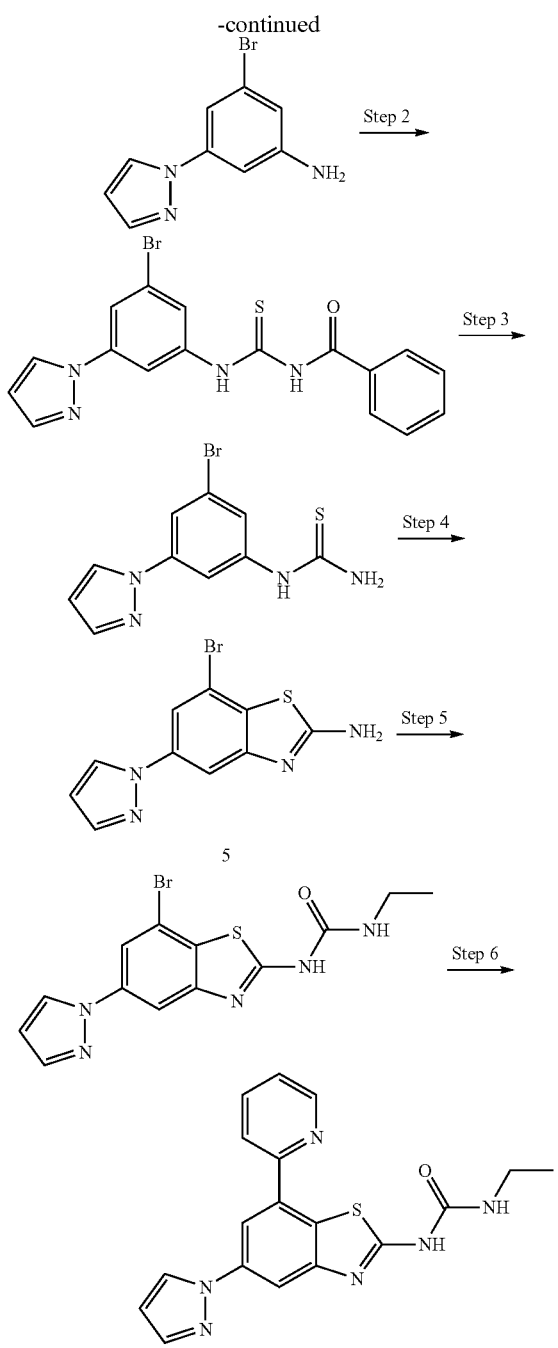

Step 1. 3-Bromo-5-pyrazol-1-yl-phenylamine

To a solution of 3,5-dibromoaniline (0.50 g, 1.99 mmol) in DMSO (2.0 mL) was added sequentially L-Proline (0.041 g, 0.36 mmol), Cs$_2$CO$_3$ (1.16 g, 3.58 mmol), CuI (0.038 g, 0.20 mmol) and pyrazole (0.12 g, 1.80 mmol). The reaction mixture was degassed for 10 min and then heated to 110° C. for 48 h. After the completion of reaction (TLC monitoring), the reaction mixture was cooled to room temperature, added water and extracted with ethyl acetate (×3). The combined organics was washed with water, dried (Na$_2$SO$_4$), filtered and concentrated. The residue was purified over silica gel (230-400 M, 15% EtOAc-Hexane) to get the desired compound (0.18 g, 37%).

Step 2. 1-Benzoyl-3-(3-bromo-5-pyrazol-1-yl-phenyl)-thiourea

To the solution of 3-bromo-5-pyrazol-1-yl-phenylamine (0.18 g, 0.76 mmol) in anhydrous acetone (5.0 mL) was added benzoylisothiocyanate (0.14 g, 0.83 mmol) and the reaction mixture was stirred at room temperature for 30 min. Acetone was distilled off and the crude residue was washed with hexane to obtain desired compound (0.27 g, 89%).

Step 3. (3-Bromo-5-pyrazol-1-yl-phenyl)-thiourea

A solution of NaOH (0.13 g, 3.35 mmol) dissolved in 1.0 mL of H$_2$O was added to a solution of 1-Benzoyl-3-(3-bromo-5-pyrazol-1-yl-phenyl)-thiourea 3 (0.27 g, 0.67 mmol) in 5.0 mL of THF. The resulting reaction mixture was stirred at 70° C. for 12 hours. THF was distilled off and extracted with ethyl acetate (×3). The combined organic layer was dried over Na$_2$SO$_4$, filtered and distilled off to get the crude residue that was washed with 2% Ethyl acetate-hexane to obtain the desired compound (0.17 g, 85%).

Step 4. 7-Bromo-5-pyrazol-1-yl-benzothiazol-2-ylamine

To a solution of (3-bromo-5-pyrazol-1-yl-phenyl)-thiourea (1.0 g, 3.0 mmol) in DCM (17.0 mL) at 0° C. was added dropwise a solution of Br$_2$ (1.07 g, 6.0 mmol, in 3.0 ml of DCM) over a period of 15 min. The reaction mixture was stirred at 0° C. for 15 min followed by refluxing for 2 h. The reaction mixture was cooled to room temperature and filtered to get the crude residue that was washed with hexane and diethyl ether. The solid thus obtained was dissolved in H$_2$O, basified with aqueous ammonia solution to pH 10-12 and extracted with ethyl acetate (×3). The combined organic was washed with water, dried (Na$_2$SO$_4$), filtered and concentrated. The residue was purified over silica gel (230-400 M, 25% EtOAc-Hexane) to get the desired product (0.30 g, 30%).

Step 5. 1-(7-Bromo-5-pyrazol-1-yl-benzothiazol-2-yl)-3-ethyl-urea

To a solution of 7-bromo-5-pyrazol-1-yl-benzothiazol-2-ylamine (0.10 g, 0.34 mmol) in dioxane (5.0 mL) was added ethylisocyante (0.24 g, 3.34 mmol) and the reaction mixture was stirred at 55° C. for 15 h. After the completion of the reaction (TLC monitoring) the solvent was evaporated and the residue was washed with hexane to get the desired product (0.11 g, 88%).

Step 6. 1-Ethyl-3-(5-pyrazol-1-yl-7-pyridin-3-yl-benzothiazol-2-yl)-urea. [Example 12]

To a solution of 1-(7-bromo-5-pyrazol-1-yl-benzothiazol-2-yl)-3-ethyl-urea (0.27 g, 0.74 mmol) in DMF:H$_2$O (2:1, 15 mL) was added 3-pyridyl boronic acid (0.11 g, 0.88 mmol) and K$_3$PO$_4$ (0.17 g, 0.81 mmol) under nitrogen atmosphere at room temperature. The reaction mixture was then degassed for half an hour followed by the addition of bis(triphenylphosphine)palladium(II) dichloride (0.077 g, 0.11 mmol). The reaction mixture was then again degassed for half an hour and heated at 120° C. for 2 h under nitrogen atmosphere. After the completion of the reaction (TLC monitoring), DMF was distilled off; water was added to the reaction mixture and extracted with ethyl acetate. The combined organic layers were dried over anhydrous Na$_2$SO$_4$, and evaporated to dryness under reduced pressure. The crude residue was purified over silica gel (230-400 M) using EtOAc-Hexane (70:30) to provide the title compound (0.066 g, 22%).

$^1$H NMR (DMSO-d$_6$, 400 MHz): δ 1.08 (t, J=7.2 Hz, 3H), 3.17 (m, 2H), 6.57 (s, 1H), 6.75 (br s, 1H), 7.60-7.63 (m, 1H), 7.78 (s, 1H), 7.86 (s, 1H), 8.13-8.20 (m, 2H), 8.70 (s, 1H), 8.97 (s, 1H) and 11.0 (br s, 1H). MS: 365.24 (M+H$^+$).

Scheme 2A

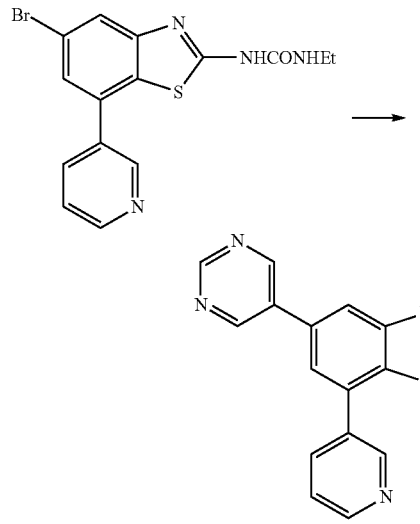

1-Ethyl-3-(7-pyridin-3-yl-5-pyrimidin-5-yl-benzothiazol-2-yl)-urea. [Example 13]

A stirred mixture of 1-(5-Bromo-7-pyridin-3-yl-benzothiazol-2-yl)-3-ethyl-urea (250 mg, 0.663 mmol), pyrimidine-5-boronic acid (86 mg, 0.696 mmol), powdered potassium phosphate tribasic (167 mg, 0,796 mmol) and 1,1'-bis(diphenylphosphino)ferrocene palladium(II)chloride complex (81 mg, 0.0995 mmol) in anhydrous 1,4-dioxane (5 ml) and anhydrous methanol (10 ml) was purged with nitrogen for 5 min and heated in a sealed vessel for 16 h at 80° C. After cooling to ambient temperature, the mixture was filtered through kieselguhr. The kieselguhr was thoroughly washed with methanol and the combined filtrates evaporated to dryness in vacuo to give the crude 1-Ethyl-3-(7-pyridin-3-yl-5-pyrimidin-5-yl-benzothiazol-2-yl)-urea which was purified by "flash" silica chromatography eluting with 0 to 5% methanol in ethyl acetate. 57 mg (22%) of an off-white solid was obtained.

$^1$H NMR (400 MHz, δ, D$_6$DMSO): 1.13 (3H, t), 3.22 (2H, m), 6.79 (1H, br t), 7.66 (1H, m), 7.85 (1H, s), 8.18 (1H, s), 8.28 (1H, d), 8.74 (1H, d), 9.07 (1H, s), 9.25 (1H, s), 9.36 (2H, s), 10.95 (1H, br s).

LC-MS m/z 377 [M+H]$^+$ Rt=2.59 min.

The following were prepared similarly:

| ID | NAME | LC-MS DATA |
|---|---|---|
| Example 14 | 1-[5-(2-Amino-pyrimidin-5-yl)-7-pyridin-3-yl-benzothiazol-2-yl]-3-ethyl-urea | m/z 392[M + H]$^+$ Rt = 2.14 min |
| Example 15 | 1-Ethyl-3-[5-(2-methoxy-pyrimidin-5-yl)-7-pyridin-3-yl-benzothiazol-2-yl]-urea | m/z 407[M + H]$^+$ Rt = 2.51 min |
| Example 16 | 1-Ethyl-3-[5-(6-hydroxy-pyridin-3-yl)-7-pyridin-3-yl-benzothiazol-2-yl]-urea | m/z 392[M + H]$^+$ Rt = 2.13 min |
| Example 17 | 1-[5-(6-Amino-pyridin-3-yl)-7-pyridin-3-yl-benzothiazol-2-yl]-3-ethyl-urea | m/z 391[M + H]$^+$ Rt = 2.61 min |
| Example 18 | 1-Ethyl-3-[5-(4-hydroxymethyl-phenyl)-7-pyridin-3-yl-benzothiazol-2-yl]-urea | m/z 405[M + H]$^+$ Rt = 2.45 min |
| Example 19 | 1-Ethyl-3-[5-(6-hydroxymethyl-pyridin-3-yl)-7-pyridin-3-yl-benzothiazol-2-yl]-urea | m/z 406[M + H]$^+$ Rt = 2.01 min |
| Example 20 | N-{5-[2-(3-Ethyl-ureido)-7-pyridin-3-yl-benzothiazol-5-yl]-pyridin-2-yl}-acetamide | m/z 433[M + H]$^+$ Rt = 2.30 min |
| Example 21 | 1-Ethyl-3-[5-(4-morpholin-4-ylmethyl-phenyl)-7-pyridin-3-yl-benzothiazol-2-yl]-urea | m/z 474[M + H]$^+$ Rt = 2.03 min |
| Example 22 | 1-Ethyl-3-(5-imidazo[1,2-a]pyridin-6-yl-7-pyridin-3-yl-benzothiazol-2-yl)-urea | m/z 415[M + H]$^+$ Rt = 1.93 min |
| Example 23 | 1-Ethyl-3-{5-[6-(4-methyl-piperazin-1-yl)-pyridin-3-yl]-7-pyridin-3-yl-benzothiazol-2-yl}-urea | m/z 474[M + H]$^+$ Rt = 1.98 min |
| Example 24 | 1-[5-(5-Cyano-pyridin-3-yl)-7-pyridin-3-yl-benzothiazol-2-yl]-3-ethyl-urea | m/z 401[M + H]$^+$ Rt = 2.93 min |
| Example 25 | 1-[5-(2-Dimethylamino-pyrimidin-5-yl)-7-pyridin-3-yl-benzothiazol-2-yl]-3-ethyl-urea | m/z 420[M + H]$^+$ Rt = 3.01 min |
| Example 26 | 5-[2-(3-Ethyl-ureido)-7-pyridin-3-yl-benzothiazol-5-yl]-pyridine-2-carboxylic acid methyl ester | m/z 434[M + H]$^+$ Rt = 2.82 min |
| Example 27 | 1-[5-(6-Cyano-pyridin-3-yl)-7-pyridin-3-yl-benzothiazol-2-yl]-3-ethyl-urea | m/z 401[M + H]$^+$ Rt = 2.75 min |
| Example 28 | 1-Ethyl-3-[5-(3-fluoro-phenyl)-7-pyridin-3-yl-benzothiazol-2-yl]-urea | m/z 393[M + H]$^+$ Rt = 3.20 min |
| Example 29 | 1-Ethyl-3-[5-(6-methoxy-pyridin-3-yl)-7-pyridin-3-yl-benzothiazol-2-yl]-urea | m/z 406[M + H]$^+$ Rt = 2.76 min |
| Example 30 | 1-Ethyl-3-(5-pyridin-4-yl-7-pyridin-3-yl-benzothiazol-2-yl)-urea | m/z 376[M + H]$^+$ Rt = 1.93 min |
| Example 31 | 1-Ethyl-3-[5-(5-methoxy-pyridin-3-yl)-7-pyridin-3-yl-benzothiazol-2-yl]-urea | m/z 404[M + H]$^+$ Rt = 2.35 min |
| Example 32 | 1-[5-(2-Cyano-pyrimidin-5-yl)-7-pyridin-3-yl-benzothiazol-2-yl]-3-ethyl-urea | m/z 402[M + H]$^+$ Rt = 2.95 min |

The following were prepared similarly using 1-(5-Bromo-7-pyridin-2-yl-benzothiazol-2-yl)-3-ethyl-urea (Scheme 10):

| | | |
|---|---|---|
| Example 33 | 1-[5-(6-Cyano-pyridin-3-yl)-7-pyridin-2-yl-benzothiazol-2-yl]-3-ethyl-urea | m/z 401[M + H]$^+$ Rt = 3.56 min |

| | | |
|---|---|---|
| Example 34 | 1-Ethyl-3-[5-(6-hydroxymethyl-pyridin-3-yl)-7-pyridin-2-yl-benzothiazol-2-yl]-urea | m/z 406[M + H]+ Rt = 2.38 min |
| Example 35 | 1-Ethyl-3-(7-pyridin-2-yl-5-pyrimidin-5-yl-benzothiazol-2-yl)-urea | m/z 377[M + H]+ Rt = 3.02 min |
| Example 36 | 1-Ethyl-3-[5-(5-methyl-pyridin-3-yl)-7-pyridin-2-yl-benzothiazol-2-yl]-urea | m/z 390[M + H]+ Rt = 2.47 min |
| Example 37 | 1-Ethyl-3-(5-furan-3-yl-7-pyridin-2-yl-benzothiazol-2-yl)-urea | m/z 365[M + H]+ Rt = 3.68 min |
| Example 38 | 1-[5-(6-Dimethylamino-pyridin-3-yl)-7-pyridin-2-yl-benzothiazol-2-yl]-3-ethyl-urea | m/z 419[M + H]+ Rt = 2.34 min |
| Example 39 | 1-Ethyl-3-[5-(4-methyl-pyridin-3-yl)-7-pyridin-2-yl-benzothiazol-2-yl]-urea | m/z 390[M + H]+ Rt = 2.35 min |
| Example 40 | 1-Ethyl-3-[5-(2-methoxy-pyridin-4-yl)-7-pyridin-2-yl-benzothiazol-2-yl]-urea | m/z 406[M + H]+ Rt = 3.65 min |
| Example 41 | 1-Ethyl-3-[5-(6-methyl-pyridin-3-yl)-7-pyridin-2-yl-benzothiazol-2-yl]-urea | m/z 390[M + H]+ Rt = 2.33 min |

The following was prepared similarly using 1-[7-(2-Amino-pyrimidin-5-yl)-5-bromo-benzothiazol-2-yl]-3-ethyl-urea (Scheme 1):

| | | |
|---|---|---|
| Example 42 | 1-[7-(2-Amino-pyrimidin-5-yl)-5-pyridin-3-yl-benzothiazol-2-yl]-3-ethyl-urea | m/z 392[M + H]+ Rt = 1.99 min |

Scheme 2B

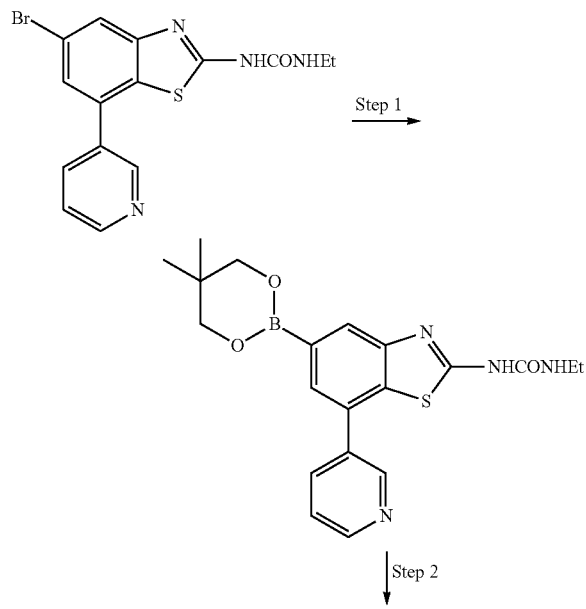

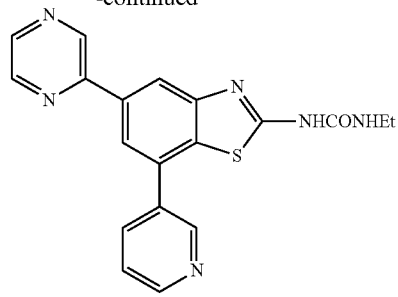

Step 1. 1-[5-(5,5-Dimethyl-[1,3,2]dioxaborinan-2-yl)-7-pyridin-3-yl-benzothiazol-2-yl]-3-ethyl-urea A mixture of 1-(5-bromo-7-(pyridine-3-yl)benzo[d]thiazol-2-yl)-3-ethylurea (100 mg, 0.265 mmol), bis(neopentyl) glycolato diboron (120 mg, 0.530 mmol) and potassium acetate (78 mg, 0.796 mmol) in dimethyl sulfoxide (4 ml) was purged with nitrogen for 5 minutes. Bis(diphenylphosphino) ferrocene palladium(II)chloride complex (22 mg, 0.0265 mmol) was added, the reaction mixture sealed and heated at 80° c. for 16 h.

Step 2. 1-Ethyl-3-(5-pyrazin-2-yl-7-pyridin-3-yl-benzothiazol-2-yl)-urea. [Example 43]

The reaction mixture from step 1 was cooled to ambient temperature. 2-Chloropyrazine (46 mg, 0.405 mmol) was added followed by aqueous cesium carbonate solution (3.7M, 0.1 ml, 0.405 mmol). The reaction mixture was purged with nitrogen for 5 minutes, treated with tetrakistriphenylphosphine palladium (0) (21 mg, 0.0265 mmol), sealed and heated at 80° C. for 8 h. The reaction mixture was cooled to ambient temperature, diluted with dichloromethane (50 ml), washed with water (3×10 ml) followed by brine (25 ml) and dried (MgSO$_4$). The solvent was removed in vacuo and the residue purified by flash silica chromatography eluting with 5% methanol in ethyl acetate to give 1-Ethyl-3-(5-pyrazin-2-yl-7-pyridin-3-yl-benzothiazol-2-yl)-urea as a pale brown solid (15 mg, 15% over 2 steps).

$^1$H NMR (400 MHz, δ, CDCl$_3$=CD$_3$OD): 1.26 (3H, t), 3.37 (2H, m), 7.51 (1H, m), 7.99 (1H, s), 8.14 (1H, d), 8.30 (1H, s), 8.56 (1H, s), 8.66 (1H, d), 8.70 (1H, s), 8.93 (1H, s), 9.14 (1H, s).

LC-MS m/z 377 [M+H]+ Rt=2.36 min.

The following were prepared similarly:

| ID | NAME | LC-MS DATA |
|---|---|---|
| Example 44 | 1-[5-(4-Amino-pyridin-3-yl)-7-pyridin-3-yl-benzothiazol-2-yl]-3-ethyl-urea | m/z 391[M + H]+ Rt = 1.93 min. |
| Example 45 | 1-[5-(6-Amino-pyrazin-2-yl)-7-pyridin-3-yl-benzothiazol-2-yl]-3-ethyl-urea | m/z 392[M + H]+ Rt = 2.26 min. |
| Example 46 | 1-Ethyl-3-[5-(6-methyl-pyridazin-3-yl)-7-pyridin-3-yl-benzothiazol-2-yl]-urea | m/z 391[M + H]+ Rt = 2.26 min. |
| Example 47 | 1-Ethyl-3-[5-(1-methyl-2-oxo-1,2-dihydro-pyridin-4-yl)-7-pyridin-3-yl-benzothiazol-2-yl]-urea | m/z 404[M + H]+ Rt = 2.25 min. |

-continued

| ID | NAME | LC-MS DATA |
|---|---|---|
| Example 48 | 1-[5-(5-Chloro-pyridin-3-yl)-7-pyridin-3-yl-benzothiazol-2-yl]-3-ethyl-urea | m/z 410[M + H]$^+$ Rt = 2.90 min. |
| Example 49 | 1-Ethyl-3-[7-pyridin-3-yl-5-(1H-pyrrolo[2,3-b]pyridin-5-yl)-benzothiazol-2-yl]-urea | m/z 415[M + H]$^+$ Rt = 2.44 min. |
| Example 50 | 1-[5-(1,6-Dimethyl-2-oxo-1,2-dihydro-pyridin-4-yl)-7-pyridin-3-yl-benzothiazol-2-yl]-3-ethyl-urea | m/z 420[M + H]$^+$ Rt = 2.34 min. |

The following were prepared similarly using 1-(5-Bromo-7-pyridin-2-yl-benzothiazol-2-yl)-3-ethyl-urea (Scheme 10):

| | | |
|---|---|---|
| Example 51 | 1-Ethyl-3-[5-(1-methyl-2-oxo-1,2-dihydro-pyridin-4-yl)-7-pyridin-2-yl-benzothiazol-2-yl]-urea | m/z 406[M + H]$^+$ Rt = 2.86 min. |
| Example 52 | 1-Ethyl-3-[5-(2-methyl-pyridin-3-yl)-7-pyridin-2-yl-benzothiazol-2-yl]-urea | m/z 390[M + H]$^+$ Rt = 2.30 min. |
| Example 53 | 1-[5-(6-Amino-pyrazin-2-yl)-7-pyridin-2-yl-benzothiazol-2-yl]-3-ethyl-urea | m/z 392[M + H]$^+$ Rt = 2.93 min. |
| Example 54 | 1-Ethyl-3-[5-(2-oxo-2,3-dihydro-1H-pyrido[2,3-b][1,4]oxazin-7-yl)-7-pyridin-2-yl-benzothiazol-2-yl]-urea | m/z 447[M + H]$^+$ Rt = 2.93 min. |
| Example 55 | 2-tert-Butylamino-N-{5-[2-(3-ethyl-ureido)-7-pyridin-2-yl-benzothiazol-5-yl]-pyridin-2-yl}-acetamide | m/z 504[M + H]$^+$ Rt = 2.33 min. |
| Example 56 | 1-Ethyl-3-[5-(2-hydroxy-pyridin-4-yl)-7-pyridin-2-yl-benzothiazol-2-yl]-urea | m/z 392[M + H]$^+$ Rt = 2.72 min. |
| Example 57 | 1-Ethyl-3-{5-[1-(2-hydroxy-ethyl)-2-oxo-1,2-dihydro-pyridin-4-yl]-7-pyridin-2-yl-benzothiazol-2-yl}-urea | m/z 436[M + H]$^+$ Rt = 2.64 min. |
| Example 58 | 1-Ethyl-3-{5-[6-(2-hydroxy-ethyl)-pyridin-3-yl]-7-pyridin-2-yl-benzothiazol-2-yl}-urea | m/z 420[M + H]$^+$ Rt = 2.30 min. |
| Example 59 | 1-Ethyl-3-[5-(6-morpholin-4-ylmethyl-pyridin-3-yl)-7-pyridin-2-yl-benzothiazol-2-yl]-urea | m/z 475[M + H]$^+$ Rt = 2.30 min. |
| Example 60 | 1-[5-(6-{[Bis-(2-methoxy-ethyl)-amino]-methyl}-pyridin-3-yl)-7-pyridin-2-yl-benzothiazol-2-yl]-3-ethyl-urea | m/z 521[M + H]$^+$ Rt = 2.42 min. |
| Example 61 | 1-{5-[6-(2-Dimethylamino-ethylamino)-pyridin-3-yl]-7-pyridin-2-yl-benzothiazol-2-yl}-3-ethyl-urea | m/z 462[M + H]$^+$ Rt = 2.09 min. |
| Example 62 | 1-Ethyl-3-{5-[5-(4-methyl-piperazin-1-yl)-pyridin-3-yl]-7-pyridin-2-yl-benzothiazol-2-yl}-urea | m/z 474[M + H]$^+$ Rt = 2.04 min. |
| Example 63 | 1-Ethyl-3-{5-[1-(2-morpholin-4-yl-ethyl)-2-oxo-1,2-dihydro-pyridin-4-yl]-7-pyridin-2-yl-benzothiazol-2-yl}-urea | m/z 505 [M + H]$^+$ Rt = 2.26 min. |
| Example 64 | N-(2-Dimethylamino-ethyl)-5-[2-(3-ethyl-ureido)-7-pyridin-2-yl-benzothiazol-5-yl]-nicotinamide | m/z 490 [M + H]$^+$ Rt = 2.21 min. |
| Example 65 | 1-Ethyl-3-[7-pyridin-2-yl-5-(5,6,7,8-tetrahydro-[1,6]naphthyridin-3-yl)-benzothiazol-2-yl]-urea | m/z 431 [M + H]$^+$ Rt = 2.63 min. |
| Example 66 | 2-Dimethylamino-N-{5-[2-(3-ethyl-ureido)-7-pyridin-2-yl-benzothiazol-5-yl]-pyridin-2-yl}-acetamide | m/z 476 [M + H]$^+$ Rt = 2.30 min. |
| Example 67 | 1-Ethyl-3-[5-(6-methylaminomethyl-pyridin-3-yl)-7-pyridin-2-yl-benzothiazol-2-yl]-urea | m/z 419 [M + H]$^+$ Rt = 2.27 min. |
| Example 68 | 5-[2-(3-Ethyl-ureido)-7-pyridin-2-yl-benzothiazol-5-yl]-N-(2-morpholin-4-yl-ethyl)-nicotinamide | m/z 532 [M + H]$^+$ Rt = 2.25 min. |
| Example 69 | {5-[2-(3-Ethyl-ureido)-7-pyridin-2-yl-benzothiazol-5-yl]-pyridin-2-yl}-acetic acid methyl ester | m/z 448 [M + H]$^+$ Rt = 3.10 min. |
| Example 70 | 2-{5-[2-(3-Ethyl-ureido)-7-pyridin-2-yl-benzothiazol-5-yl]-pyridin-2-yl}-N-methyl-acetamide | m/z 447 [M + H]$^+$ Rt = 2.53 min. |
| Example 71 | 1-Ethyl-3-[5-(7-oxo-5,6,7,8-tetrahydro-[1,8]naphthyridin-3-yl)-7-pyridin-2-yl-benzothiazol-2-yl]-urea | m/z 445 [M + H]$^+$ Rt = 3.01 min. |
| Example 72 | 1-{5-[1-(2-Dimethylamino-ethyl)-2-oxo-1,2-dihydro-pyridin-4-yl]-7-pyridin-2-yl-benzothiazol-2-yl}-3-ethyl-urea | m/z 463 [M + H]$^+$ Rt = 2.24 min. |

The following were prepared similarly using 1-[7-(2-Amino-pyrimidin-5-yl)-5-bromo-benzothiazol-2-yl]-3-ethyl-urea (Scheme 1):

| | | |
|---|---|---|
| Example 73 | 1-[7-(2-Amino-pyrimidin-5-yl)-5-pyrazin-2-yl-benzothiazol-2-yl]-3-ethyl-urea | m/z 393[M + H]$^+$ Rt = 2.45 min. |
| Example 74 | 1-[7-(2-Amino-pyrimidin-5-yl)-5-pyridin-2-yl-benzothiazol-2-yl]-3-ethyl-urea | m/z 392[M + H]$^+$ Rt = 2.19 min. |

Scheme 3A

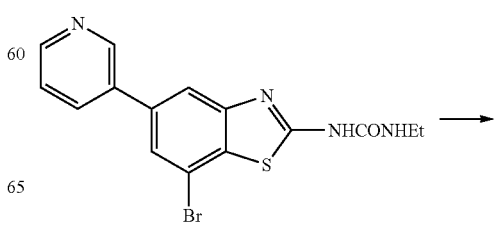

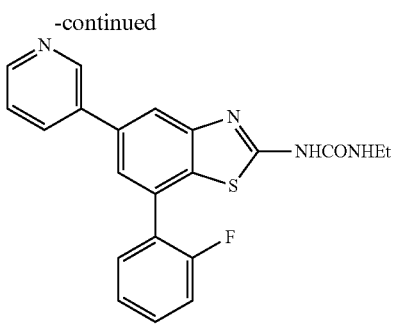

1-Ethyl-3-[7-(2-fluoro-phenyl)-5-pyridin-3-yl-benzothiazol-2-yl]-urea. [Example 75]

A stirred mixture of 1-(7-Bromo-5-pyridin-3-yl-benzothiazol-2-yl)-3-ethyl-urea (50 mg, 0.133 mmol), 2-fluorobenzeneboronic acid (19 mg, 0.139 mmol), powdered potassium phosphate tribasic (34 mg, 0.160 mmol) and 1,1'-bis(diphenylphosphino)ferrocene palladium(II)chloride complex (16 mg, 0.01995 mmol) in anhydrous 1,4-dioxane (1 ml) and anhydrous methanol (2 ml) was purged with nitrogen for 5 min and heated in a sealed vessel for 16 h at 80° C. After cooling to ambient temperature, the mixture was filtered through kieselguhr. The kieselguhr was thoroughly washed with methanol and the combined filtrates evaporated to dryness in vacuo to give the crude 1-Ethyl-3-[7-(2-fluoro-phenyl)-5-pyridin-3-yl-benzothiazol-2-yl]-urea which was purified by "flash" silica chromatography eluting with 0 to 30% methanol in ethyl acetate. 12 mg of a pale-brown solid was obtained.

$^1$H NMR (400 MHz, δ, D$_6$DMSO): 1.12 (3H, t), 3.21 (2H, m), 6.77 (1H, br t), 7.46 (2H, m), 7.55 (2H, m), 7.62 (1H, s), 7.74 (1H, t), 8.05 (1H, s), 8.24 (1H, d), 8.63 (1H, d), 9.05 (1H, s), 10.88 (1H, br s).

LC-MS m/z 393 [M+H]$^+$ Rt=2.79 min.

The following were prepared similarly:

| ID | NAME | LC-MS DATA |
|---|---|---|
| Example 76 | 1-Ethyl-3-[7-(2-fluoro-pyridin-3-yl)-5-pyridin-3-yl-benzothiazol-2-yl]-urea | m/z 394[M + H]$^+$ Rt = 2.41 min. |
| Example 77 | 1-Ethyl-3-(5-pyridin-3-yl-7-thiophen-3-yl-benzothiazol-2-yl)-urea | m/z 381[M + H]$^+$ Rt = 2.66 min. |

The following were prepared similarly but using the alternative conditions shown below:
A. Solvent: DMF: Water (2:1). Base: potassium phosphate. Catalyst: bis(triphenylphosphine)palladium(II) dichloride. Temperature: 120° C.
B. Solvent: Toluene: Water (9:1). Base: potassium phosphate Catalyst: Palladium(II) acetate and tricyclohexylphosphine. Temperature: 110° C.
C. Solvent: DMF: Water (2:1). Base: potassium phosphate. Catalyst: 1,1'-bis(diphenylphosphino)ferrocene palladium(II)chloride complex. Temperature: 120° C.
D. Solvent: DMF: Water (2:1). Base: Sodium carbonate. Catalyst: 1,1'-bis(diphenylphosphino)ferrocene palladium(II)chloride complex. Temperature: 120° C.
E. Solvent: DMF: Water (2:1). Base: potassium phosphate. Catalyst: tetrakis(triphenylphosphine)palladium(0). Temperature: 120° C.
F. Solvent: DMF: Water (2:1). Base: Sodium carbonate. Catalyst: tetrakis(triphenylphosphine)palladium(0). Temperature: 120° C.

| ID | CONDITIONS | NAME | LC-MS/NMR DATA |
|---|---|---|---|
| Example 78 | A | 1-Ethyl-3-(7-phenyl-5-pyridin-3-yl-benzothiazol-2-yl)-urea | $^1$H-NMR (400 MHz, DMSO-d$_6$): δ 1.08 (t, J = 7.20 Hz, 3H), 3.15 (m, 2H), 6.75 (br s, 1H), 7.46-7.50 (m, 2H), 7.52-7.62 (m, 3H), 7.81 (d, J = 7.60 Hz, 2H), 7.96 (s, 1H), 8.23 (d, J = 8.0 Hz, 1H), 8.59 (m, 1H), 9.03 (s, 1H) and 10.84 (br s, 1H). MS: 375.31 (M + H)$^+$. |
| Example 79 | B | 1-(7-Cyclopropyl-5-pyridin-3-yl-benzothiazol-2-yl)-3-ethyl-urea | $^1$H NMR (DMSO-d$_6$, 400 MHz): δ 0.92-0.95 (m, 2H), 1.02-1.05 (m, 2H), 1.10 (t, J = 7.2 Hz, 3H), 2.03-2.08 (m, 1H), 3.19 (q, J = 7.2 Hz, 2H), 6.90 (br s, 1H), 7.15 (s, 1H), 7.45-7.49 (m, 1H), 7.75 (s, 1H), 8.10-8.13 (m, 1H), 8.55 (m, 1H), 8.92 (s, 1H) and 10.91 (br s, 1H). MS: 339.07, (M + H$^+$). |
| Example 80 | A | 1-Ethyl-3-[7-(1H-pyrazol-4-yl)-5-pyridin-3-yl-benzothiazol-2-yl]-urea | $^1$H NMR (DMSO-d$_6$, 400 MHz): δ 1.08 (t, J = 7.20 Hz, 3H), 3.15-3.25 (m, 2H), 6.85 (br s, 1H), 7.49-7.52 (m, 1H), 7.60 (s, 1H), 7.84 (s, 1H), 8.10-8.40 (m, 3H), 8.58-8.59 (m, 1H), 9.03 (s, 1H), 10.92 (br s, 1H) and 13.24 (br s, 1H). MS: 365.11 (M + H)$^+$. |

-continued

| ID | CONDITIONS | NAME | LC-MS/NMR DATA |
|---|---|---|---|
| Example 81 | A | 1-Ethyl-3-{7-[1-(2-morpholin-4-yl-ethyl)-1H-pyrazol-4-yl]-5-pyridin-3-yl-benzothiazol-2-yl}-urea | $^1$H NMR (DMSO-$d_6$, 400 MHz): δ 1.10 (t, J = 7.2 Hz, 3H), 2.45 (m, 4H), 2.76-2.79 (m, 2H), 3.18-3.22 (m, 2H), 3.57 (m, 4H), 4.33-4.36 (m, 2H), 6.78 (br s, 1H), 7.49-7.52 (m, 1H), 7.77 (s, 1H), 7.84 (s, 1H), 8.08 (s, 1H), 8.21 (d, J = 7.2 Hz, 1H), 8.59 (d, J = 3.6 Hz, 1H), 9.03 (s, 2H), 10.89 (br s, 1H). MS: 478.37 (M + H$^+$). |
| Example 82 | C | 1-Ethyl-3-[7-(1H-pyrazol-3-yl)-5-pyridin-3-yl-benzothiazol-2-yl]-urea | $^1$H NMR (DMSO-$d_6$, 400 MHz): δ 1.11 (t, J = 7.2 Hz, 3H), 3.20 (q, J = 7.2 Hz, 2H), 6.83 (br s, 1H), 7.15 (s, 1H), 7.50-7.55 (m, 1H), 7.92 (d, J = 8.40 Hz, 2H), 8.02 (s, 1H), 8.24 (d, J = 8.40 Hz, 1H), 8.60 (m, 1H), 9.06 (s, 1H) and 10.64 (br s, 1H). MS: 363.07 (M − H$^+$). |
| Example 83 | A | 1-Ethyl-3-[7-(1-methyl-1H-pyrazol-4-yl)-5-pyridin-3-yl-benzothiazol-2-yl]-urea | $^1$H NMR (DMSO-$d_6$, 400 MHz): δ 1.09 (t, J = 7.20 Hz, 3H), 3.20 (q, J = 7.20 Hz, 2H), 3.96 (s, 3H), 6.76 (br s, 1H), 7.49-7.52 (m, 1H), 7.76 (s, 1H), 7.85 (s, 1H), 8.06 (s, 1H), 8.21 (m, 1H), 8.30 (s, 1H), 8.60 (br s, 1H), 9.03 (s, 1H) and 10.84 (br s, 1H). MS: 379.20 (M + H)$^+$. |
| Example 84 | D | 1-Ethyl-3-[7-(4-methoxy-phenyl)-5-pyridin-3-yl-benzothiazol-2-yl]-urea | $^1$H NMR (DMSO-$d_6$, 400 MHz): δ 1.08 (t, J = 7.20 Hz, 3H), 3.18 (q, J = 7.20 Hz, 2H), 3.84 (s, 3H), 6.76 (br s, 1H), 7.14 (d, J = 8.80 Hz, 2H), 7.48-7.52 (m, 1H), 7.56 (s, 1H), 7.73 (d, J = 8.40 Hz, 2H), 7.91 (br s, 1H), 8.21 (m, 1H), 8.58 (dd, J = 1.20 and 4.80 Hz respectively, 1H), 9.02 (s, 1H) and 10.81 (br s, 1H). MS: 405.29 (M + H$^+$). |
| Example 85 | C | 1-Ethyl-3-[7-(2-methoxy-pyridin-3-yl)-5-pyridin-3-yl-benzothiazol-2-yl]-urea | $^1$H NMR (DMSO-$d_6$, 400 MHz): δ 1.07 (t, J = 7.20 Hz, 3H), 3.14-3.17 (m, 2H), 3.88 (s, 3H), 6.74 (br s, 1H), 7.16-7.19 (m, 2H), 7.48-7.51 (m, 1H), 7.54 (s, 1H), 7.91-7.94 (m, 1H), 7.97 (s, 1H), 8.18-8.20 (m, 1H), 8.31 (dd, J = 1.20 and 4.80 Hz respectively, 1H), 8.58-8.59 (m, 1H) and 8.99 (br s, 1H). MS: 404.04 (M + H$^+$). |
| Example 86 | D | 1-Ethyl-3-[7-(3-methoxy-phenyl)-5-pyridin-3-yl-benzothiazol-2-yl]-urea | $^1$H NMR (DMSO-$d_6$, 400 MHz): δ 1.08 (t, J = 7.20 Hz, 3H), 3.18 (q, J = 7.20 Hz, 2H), 3.85 (s, 3H), 6.75 (br s, 1H), 7.04-7.07 (m, 1H), 7.32 (s, 1H), 7.38 (d, J = 7.60 Hz, 1H), 7.46-7.52 (m, 2H), 7.63 (s, 1H), 7.96 (s, 1H), 8.24 (d, J = 8.0 Hz, 1H), 8.60 (m, 1H), 9.04 (s, 1H) and 10.83 (br s, 1H). MS: 403.05 (M − H). |
| Example 87 | E | 1-Ethyl-3-[7-(2-methoxy-phenyl)-5-pyridin-3-yl-benzothiazol-2-yl]-urea | $^1$H NMR (DMSO-$d_6$, 400 MHz): δ 1.07 (t, J = 7.20 Hz, 3H), 3.16 (q, J = 7.20 Hz, 2H), 3.76 (s, 3H), 6.72 (br s, 1H), 7.09 (t, J = 7.20 Hz, 1H), 7.21 (d, J = 8.40 Hz, 1H), 7.44-7.50 (m, 4H), 7.92 (s, 1H), 8.18 (d, J = 8.0 Hz, 1H), 8.58 (m, 1H), 8.97 (s, 1H) and 10.74 (br s, 1H). MS: 405.27 (M + H$^+$). |
| Example 88 | A | 1-[7-(6-Chloro-pyridin-2-yl)-5- | $^1$H NMR (DMSO-$d_6$, 400 MHz): δ 1.11 (t, J = 6.80 Hz, |

-continued

| ID | CONDITIONS | NAME | LC-MS/NMR DATA |
|---|---|---|---|
| | | pyridin-3-yl-benzothiazol-2-yl]-3-ethyl-urea | 3H), 3.21 (m, 2H), 7.0 (br s, 1H), 7.54-7.58 (m, 2H), 8.04-8.08 (m, 2H), 8.30-8.33 (m, 2H), 8.54 (d, J = 7.60 Hz, 1H), 8.62 (s, 1H), 9.13-9.15 (m, 1H) and 10.74 (br s, 1H). MS: 410.18 (M + H). Qualitative HPLC Purity (Xbridge C18, 250 × 4.6 mm, 262 nm): 82.94% (Rt = 14.84 min). M.P. 249.90° C. |
| Example 89 | C | 1-Ethyl-3-[5-pyridin-3-yl-7-(6-trifluoromethyl-pyridin-2-yl)-benzothiazol-2-yl]-urea | $^1$H NMR (DMSO-$d_6$, 400 MHz): δ 1.12 (t, J = 6.40 Hz, 3H), 3.21 (m, 2H), 6.82 (br s, 1H), 7.55 (s, 1H), 7.95 (m, 1H), 8.12 (s, 1H), 8.27-8.34 (m, 2H), 8.43 (s, 1H), 8.63 (s, 1H), 8.85 (d, J = 8.0 Hz, 1H), 9.15 (s, 1H) and 10.67 (br s, 1H). MS: 444.21 (M + H$^+$). Qualitative HPLC Purity (Xbridge C18, 250 × 4.6 mm, 263 nm): 96.86% (Rt = 15.07 min). M.P. 256.70° C. |
| Example 90 | F | 1-Ethyl-3-[5-pyridin-3-yl-7-(1H-pyrrol-2-yl)-benzothiazol-2-yl]-urea | $^1$H NMR (DMSO-$d_6$, 400 MHz): δ 1.10 (t, J = 7.20 Hz, 3H), 3.18-3.23 (m, 2H), 6.28 (br s, 1H), 6.63 (s, 1H), 7.02 (m, 2H), 7.51-7.55 (m, 1H), 7.82 (s, 1H), 7.88 (s, 1H), 8.23 (d, J = 8.0 Hz, 1H), 8.35 (br s, 1H), 8.59 (m, 1H), 9.07 (s, 1H) and 11.64 (br s, 1H). MS: 364.18 (M + H)$^+$. Qualitative HPLC Purity (Xbridge C18, 250 × 4.6 mm, 278 nm): 98.28% (Rt = 13.94 min). M.P. 220.0° C. |

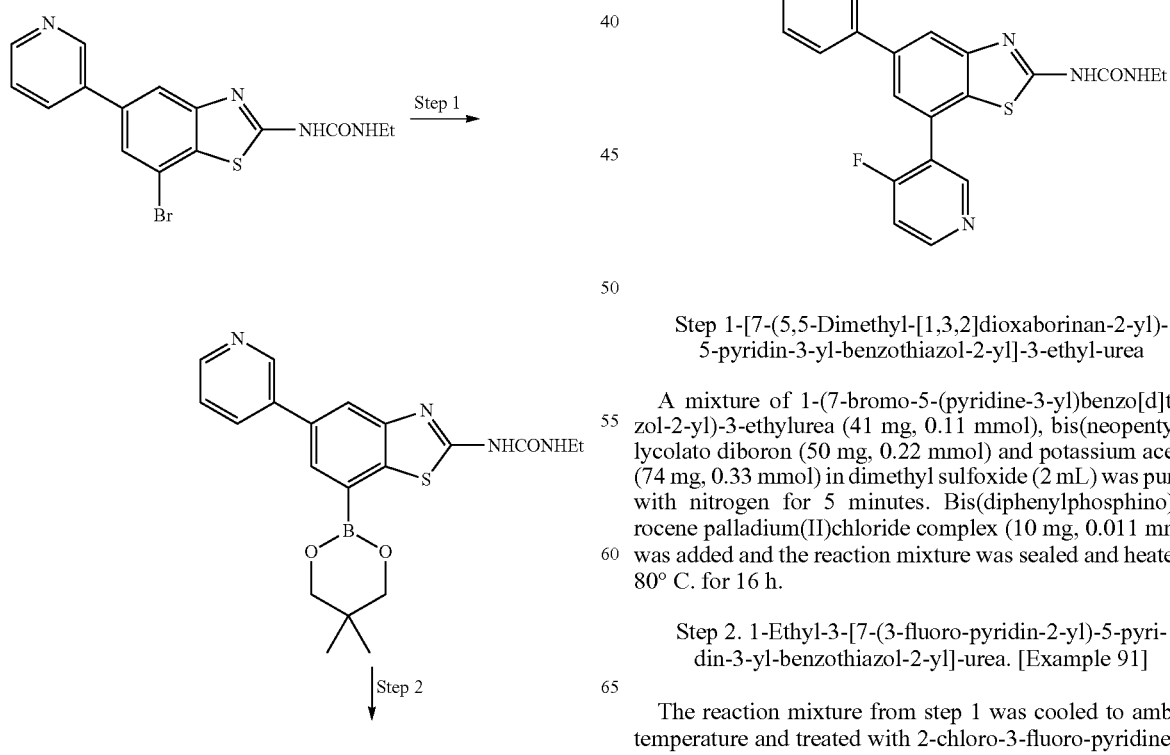

Step 1-[7-(5,5-Dimethyl-[1,3,2]dioxaborinan-2-yl)-5-pyridin-3-yl-benzothiazol-2-yl]-3-ethyl-urea A mixture of 1-(7-bromo-5-(pyridine-3-yl)benzo[d]thiazol-2-yl)-3-ethylurea (41 mg, 0.11 mmol), bis(neopentyl)glycolato diboron (50 mg, 0.22 mmol) and potassium acetate (74 mg, 0.33 mmol) in dimethyl sulfoxide (2 mL) was purged with nitrogen for 5 minutes. Bis(diphenylphosphino)ferrocene palladium(II)chloride complex (10 mg, 0.011 mmol) was added and the reaction mixture was sealed and heated at 80° C. for 16 h.

Step 2. 1-Ethyl-3-[7-(3-fluoro-pyridin-2-yl)-5-pyridin-3-yl-benzothiazol-2-yl]-urea. [Example 91]

The reaction mixture from step 1 was cooled to ambient temperature and treated with 2-chloro-3-fluoro-pyridine (15 mg, 0.11 mmol) and cesium carbonate (53 mg, 0.165 mmol). The reaction mixture was purged with nitrogen for 5 minutes, treated with tetrakis triphenylphosphine palladium (0) (13 mg, 0.011 mmol), sealed and heated at 80° C. for 8 h. The reaction mixture was cooled to ambient temperature, diluted with dichloromethane (50 ml), washed with water (3×10 mL) followed by brine (25 ml) and dried (MgSO$_4$). The solvent was removed in vacuo and the residue purified by flash silica chromatography eluting with 5% methanol in ethyl acetate to give the 1-Ethyl-3-[7-(3-fluoro-pyridin-2-yl)-5-pyridin-3-yl-benzothiazol-2-yl]-urea as a white solid (7.5 mg, 17%).

$^1$H NMR (400 MHz, δ, D$_6$DMSO): 1.15 (3H, t), 3.26 (2H, m), 6.85 (1H, br t), 7.58 (1H, m), 7.65 (1H, m), 8.02 (1H, m), 8.12 (1H, s), 8.23 (2H, m), 8.66 (1H, m), 8.75 (1H, d), 9.05 (1H, s), 10.74 (1H, br s).

LC-MS m/z 394 [M+H]$^+$ Rt=2.47 min.

The following were prepared similarly:

| ID | NAME | LC-MS DATA |
|---|---|---|
| Example 92 | 1-Ethyl-3-(5-pyridin-3-yl-7-thiazol-2-yl-benzothiazol-2-yl)-urea | m/z 382 [M + H]$^+$ Rt = 2.49 min. |
| Example 93 | 1-Ethyl-3-(5-pyridin-3-yl-7-pyrimidin-2-yl-benzothiazol-2-yl)-urea | m/z 377 [M + H]$^+$ Rt = 2.29 min. |
| Example 94 | 1-[7-(3-Amino-pyridin-2-yl)-5-pyridin-3-yl-benzothiazol-2-yl]-3-ethyl-urea | m/z 391 [M + H]$^+$ Rt = 2.63 min. |
| Example 95 | 1-[7-(3-Cyano-pyridin-2-yl)-5-pyridin-3-yl-benzothiazol-2-yl]-3-ethyl-urea | m/z 401 [M + H]$^+$ Rt = 2.42 min. |
| Example 96 | 1-Ethyl-3-[7-(5-hydroxymethyl-pyridin-2-yl)-5-pyridin-3-yl-benzothiazol-2-yl]-urea | m/z 406 [M + H]$^+$ Rt = 2.69 min. |
| Example 97 | 1-[7-(5-Aminomethyl-pyridin-2-yl)-5-pyridin-3-yl-benzothiazol-2-yl]-3-ethyl-urea | m/z 405 [M + H]$^+$ Rt = 1.77 min. |
| Example 98 | 6-[2-(3-Ethyl-ureido)-5-pyridin-3-yl-benzothiazol-7-yl]-nicotinamide | m/z 419 [M + H]$^+$ Rt = 2.06 min. |
| Example 99 | 1-[7-(5-Amino-pyridin-2-yl)-5-pyridin-3-yl-benzothiazol-2-yl]-3-ethyl-urea | m/z 391 [M + H]$^+$ Rt = 2.09 min. |
| Example 100 | 1-[7-(4-Amino-pyridin-2-yl)-5-pyridin-3-yl-benzothiazol-2-yl]-3-ethyl-urea | m/z 391 [M + H]$^+$ Rt = 1.74 min. |
| Example 101 | 1-Ethyl-3-(7-pyrazin-2-yl-5-pyridin-3-yl-benzothiazol-2-yl)-urea | m/z 377 [M + H]$^+$ Rt = 2.24 min. |
| Example 102 | 1-[7-(2,4-Dimethyl-thiazol-5-yl)-5-pyridin-3-yl-benzothiazol-2-yl]-3-ethyl-urea | m/z 410 [M + H]$^+$ Rt = 2.37 min. |
| Example 103 | 1-[7-(3-Cyano-6-methyl-pyridin-2-yl)-5-pyridin-3-yl-benzothiazol-2-yl]-3-ethyl-urea | m/z 415 [M + H]$^+$ Rt = 3.10 min. |
| Example 104 | 1-Ethyl-3-[7-(6-hydroxymethyl-pyridin-2-yl)-5-pyridin-3-yl-benzothiazol-2-yl]-urea | m/z 406 [M + H]$^+$ Rt = 2.19 min. |
| Example 105 | 1-Ethyl-3-[7-(6-methoxy-pyridazin-3-yl)-5-pyridin-3-yl-benzothiazol-2-yl]-urea | m/z 406 [M + H]$^+$ Rt = 2.19 min. |
| Example 106 | 1-Ethyl-3-[7-(4-hydroxymethyl-thiazol-2-yl)-5-pyridin-3-yl-benzothiazol-2-yl]-urea | m/z 412 [M + H]$^+$ Rt = 2.23 min. |
| Example 107 | 1-[7-(5-Cyano-pyridin-2-yl)-5-pyridin-3-yl-benzothiazol-2-yl]-3-ethyl-urea | m/z 401 [M + H]$^+$ Rt = 3.13 min. |
| Example 108 | 2-[2-(3-Ethyl-ureido)-5-pyridin-3-yl-benzothiazol-7-yl]-isonicotinamide | m/z 419 [M + H]$^+$ Rt = 2.60 min. |
| Example 109 | 1-Ethyl-3-[7-(3-hydroxymethyl-pyridin-2-yl)-5-pyridin-3-yl-benzothiazol-2-yl]-urea | m/z 406 [M + H]$^+$ Rt = 2.00 min. |
| Example 110 | 1-[7-(4-Amino-pyrimidin-2-yl)-5-pyridin-3-yl-benzothiazol-2-yl]-3-ethyl-urea | m/z 392 [M + H]$^+$ Rt = 1.90 min. |
| Example 111 | 1-Ethyl-3-[5-pyridin-3-yl-7-(1H-pyrrolo[2,3-b]pyridin-6-yl)-benzothiazol-2-yl]-urea | m/z 415 [M + H]$^+$ Rt = 2.62 min. |
| Example 112 | 1-Ethyl-3-[7-(4-methoxy-pyridin-2-yl)-5-pyridin-3-yl-benzothiazol-2-yl]-urea | m/z 406 [M + H]$^+$ Rt = 2.41 min. |
| Example 113 | 1-[7-(6-Cyano-pyridin-2-yl)-5-pyridin-3-yl-benzothiazol-2-yl]-3-ethyl-urea | m/z 401 [M + H]$^+$ Rt = 3.22 min. |
| Example 114 | 1-[7-(2-Amino-pyrimidin-4-yl)-5-pyridin-3-yl-benzothiazol-2-yl]-3-ethyl-urea | m/z 392 [M + H]$^+$ Rt = 1.96 min. |
| Example 115 | 1-Ethyl-3-[5-pyridin-3-yl-7-(1H-pyrrolo[2,3-c]pyridin-7-yl)-benzothiazol-2-yl]-urea | m/z 415 [M + H]$^+$ Rt = 1.79 min. |
| Example 116 | 1-Ethyl-3-[5-pyridin-3-yl-7-(7H-pyrrolo[2,3-d]pyrimidin-4-yl)-benzothiazol-2-yl]-urea | m/z 416 [M + H]$^+$ Rt = 2.22 min. |
| Example 117 | 1-Ethyl-3-(5'-pyridin-3-yl-[2,7']bibenzothiazolyl-2'-yl)-urea | m/z 432 [M + H]$^+$ Rt = 3.21 min. |
| Example 118 | 1-Ethyl-3-[7-(3-methoxy-pyridin-2-yl)-5-pyridin-3-yl-benzothiazol-2-yl]-urea | m/z 406 [M + H]$^+$ Rt = 2.35 min. |
| Example 119 | 1-[7-(4-Cyano-pyridin-2-yl)-5-pyridin-3-yl-benzothiazol-2-yl]-3-ethyl-urea | m/z 401 [M + H]$^+$ Rt = 3.15 min. |
| Example 120 | 1-Ethyl-3-[7-(5-morpholin-4-ylmethyl-pyridin-2-yl)-5-pyridin-3-yl-benzothiazol-2-yl]-urea | m/z 475 [M + H]$^+$ Rt = 2.75 min. |
| Example 121 | 1-Ethyl-3-[7-(4-hydroxymethyl-pyridin-2-yl)-5-pyridin-3-yl-benzothiazol-2-yl]-urea | m/z 406 [M + H]$^+$ Rt = 2.17 min. |
| Example 122 | 1-Ethyl-3-[7-(6-methoxy-pyrimidin-4-yl)-5-pyridin-3-yl-benzothiazol-2-yl]-urea | m/z 407 [M + H]$^+$ Rt = 2.55 min. |
| Example 123 | 1-[7-(6-Amino-pyrazin-2-yl)-5-pyridin-3-yl-benzothiazol-2-yl]-3-ethyl-urea | m/z 392 [M + H]$^+$ Rt = 2.13 min. |
| Example 124 | 1-Ethyl-3-[7-(4-methoxy-pyrimidin-2-yl)-5-pyridin-3-yl-benzothiazol-2-yl]-urea | m/z 407 [M + H]$^+$ Rt = 2.53 min. |
| Example 125 | 1-[7-(6-Amino-pyridin-2-yl)-5-pyridin-3-yl-benzothiazol-2-yl]-3-ethyl-urea | m/z 391 [M + H]$^+$ Rt = 2.09 min. |
| Example 126 | 1-[7-(3-Chloro-pyridin-2-yl)-5-pyridin-3-yl-benzothiazol-2-yl]-3-ethyl-urea | m/z 410 [M + H]$^+$ Rt = 2.53 min. |
| Example 127 | 1-[7-(4-Chloro-pyridin-2-yl)-5-pyridin-3-yl-benzothiazol-2-yl]-3-ethyl-urea | m/z 410 [M + H]$^+$ Rt = 2.87 min. |
| Example 128 | 1-Ethyl-3-[5-pyridin-3-yl-7-(3-trifluoromethyl-pyridin-2-yl)-benzothiazol-2-yl]-urea | m/z 444 [M + H]$^+$ Rt = 2.58 min. |
| Example 129 | 1-Ethyl-3-[5-pyridin-3-yl-7-(5-trifluoromethyl-pyridin-2-yl)-benzothiazol-2-yl]-urea | m/z 444 [M + H]$^+$ Rt = 3.04 min. |
| Example 130 | 1-[7-(5-Chloro-pyridin-2-yl)-5-pyridin-3-yl-benzothiazol-2-yl]-3-ethyl-urea | m/z 410 [M + H]$^+$ Rt = 2.87 min. |

| ID | NAME | LC-MS DATA |
|---|---|---|
| Example 131 | 1-[7-(5-Amino-pyrazin-2-yl)-5-pyridin-3-yl-benzothiazol-2-yl]-3-ethyl-urea | m/z 392 [M + H]+ Rt = 2.10 min. |
| Example 132 | 1-[7-(5-Dimethylaminomethyl-pyridin-2-yl)-5-pyridin-3-yl-benzothiazol-2-yl]-3-ethyl-urea | m/z 433 [M + H]+ Rt = 1.87 min. |

The following were prepared similarly using N-{5-[7-Bromo-2-(3-ethyl-ureido)-benzothiazol-5-yl]-pyridin-2-yl}-acetamide (Scheme 1A):

| | | |
|---|---|---|
| Example 133 | N-{5-[2-(3-Ethyl-ureido)-7-pyridin-2-yl-benzothiazol-5-yl]-pyridin-2-yl}-acetamide | m/z 433 [M + H]+ Rt = 3.00 min. |
| Example 134 | N-{5-[2-(3-Ethyl-ureido)-7-pyrazin-2-yl-benzothiazol-5-yl]-pyridin-2-yl}-acetamide | m/z 434 [M + H]+ Rt = 2.74 min. |
| Example 135 | N-{5-[7-(5-Amino-pyridin-2-yl)-2-(3-ethyl-ureido)-benzothiazol-5-yl]-pyridin-2-yl}-acetamide | m/z 448 [M + H]+ Rt = 2.48 min. |
| Example 136 | N-{5-[7-(5-Cyano-pyridin-2-yl)-2-(3-ethyl-ureido)-benzothiazol-5-yl]-pyridin-2-yl}-acetamide | m/z 458 [M + H]+ Rt = 3.09 min. |
| Example 137 | N-{5-[2-(3-Ethyl-ureido)-7-(1H-pyrrolo[2,3-c]pyridin-7-yl)-benzothiazol-5-yl]-pyridin-2-yl}-acetamide | m/z 472 [M + H]+ Rt = 2.08 min. |

The following were prepared similarly using 1-[5-(6-Amino-pyridin-3-yl)-7-bromo-benzothiazol-2-yl]-3-ethyl-urea (Scheme 1A):

| | | |
|---|---|---|
| Example 138 | 1-[5-(6-Amino-pyridin-3-yl)-7-pyridin-2-yl-benzothiazol-2-yl]-3-ethyl-urea | m/z 391 [M + H]+ Rt = 2.25 min. |

The following were prepared similarly using 1-[5-(2-Amino-pyrimidin-5-yl)-7-bromo-benzothiazol-2-yl]-3-ethyl-urea (Scheme 1):

| | | |
|---|---|---|
| Example 139 | 1-[5-(2-Amino-pyrimidin-5-yl)-7-pyrazin-2-yl-benzothiazol-2-yl]-3-ethyl-urea | m/z 393 [M + H]+ Rt = 2.53 min. |

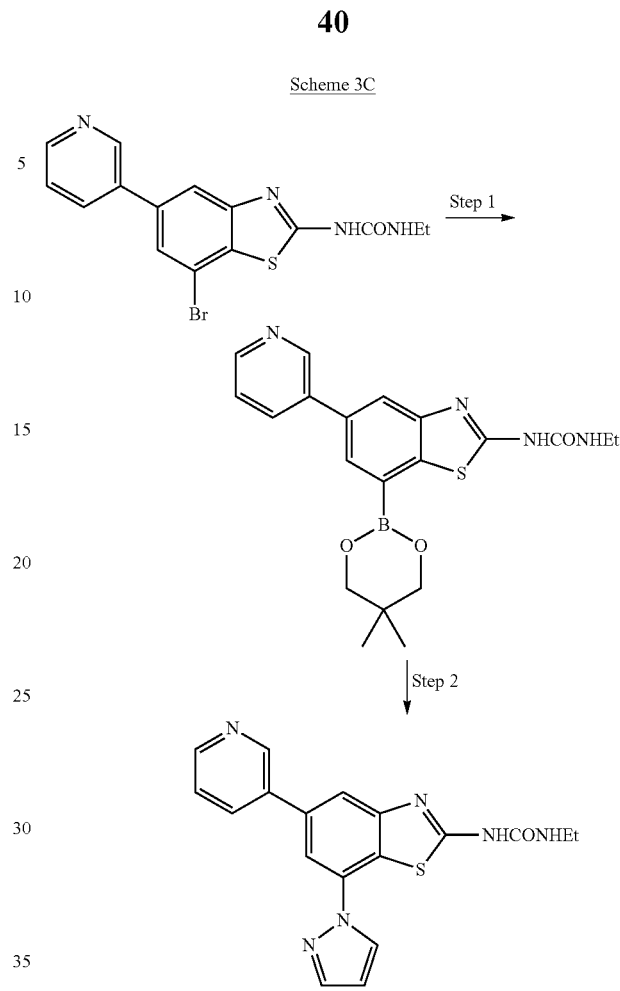

Scheme 3C

Step 1-[7-(5,5-Dimethyl-[1,3,2]dioxaborinan-2-yl)-5-pyridin-3-yl-benzothiazol-2-yl]-3-ethyl-urea A stirred mixture of 1-(7-bromo-5-(pyridine-3-yl)benzo[d]thiazol-2-yl)-3-ethylurea (100 mg, 0.2652 mmol), bis(neopentyl)glycolato diboron (120 mg, 0.5303 mmol) and potassium acetate (78 mg, 0.7957 mmol) in dimethyl sulfoxide (4 ml) was purged with nitrogen for 5 min, treated with 1,1' bis(diphenylphosphiono)ferrocene palladium(II)chloride complex (22 mg, 0.02653 mmol) and heated at 80 C. for 16 h. After cooling to ambient temperature, the mixture was diluted with dichloromethane (50 mL), washed with water (3×10 mL), dried over MgSO$_4$ and the solvent removed in vacuo to give the crude 1-[7-(5,5-Dimethyl-[1,3,2]dioxaborinan-2-yl)-5-pyridin-3-yl-benzothiazol-2-yl]-3-ethyl-urea which was used in the next step without further purification.

Step 2. 1-Ethyl-3-(7-pyrazol-1-yl-5-pyridin-3-yl-benzothiazol-2-yl)-urea. [Example 140]

A mixture of the crude 1-[7-(5,5-Dimethyl-[1,3,2]dioxaborinan-2-yl)-5-pyridin-3-yl-benzothiazol-2-yl]-3-ethyl-urea (116 mg, 0.339 mmol), pyrazole (25 mg, 0.373 mmol), copper(II)acetate (71 mg, 0.39 mmol), anhydrous triethylamine (188 mg, 1.865 mmol) and powdered 4A molecular sieves (8 pellets) in anhydrous dichloromethane was stirred in an open vessel at ambient temperature for 2 days. The resultant mixture was filtered and the solvent removed in vacuo to give the crude 1-Ethyl-3-(7-pyrazol-1-yl-5-pyridin-3-yl-benzothiazol-2-yl)-urea which was purified by preparative HPLC. The product was obtained as an off-white solid (8 mg).

$^1$H NMR (400 MHz, δ, D$_6$DMSO): 1.13 (3H, t), 3.23 (2H, m), 6.71 (1H, s), 7.06 (1H, br s), 7.58 (1H, br t), 7.93 (1H, s), 7.96 (1H, s), 8.08 (1H, s), 8.33 (1H, d), 8.66 (1H, br s), 8.98 (1H, s), 9.15 (1H, br s), 10.80 (1H, br s).

LC-MS m/z 365 [M+H]$^+$ Rt=2.41 min.

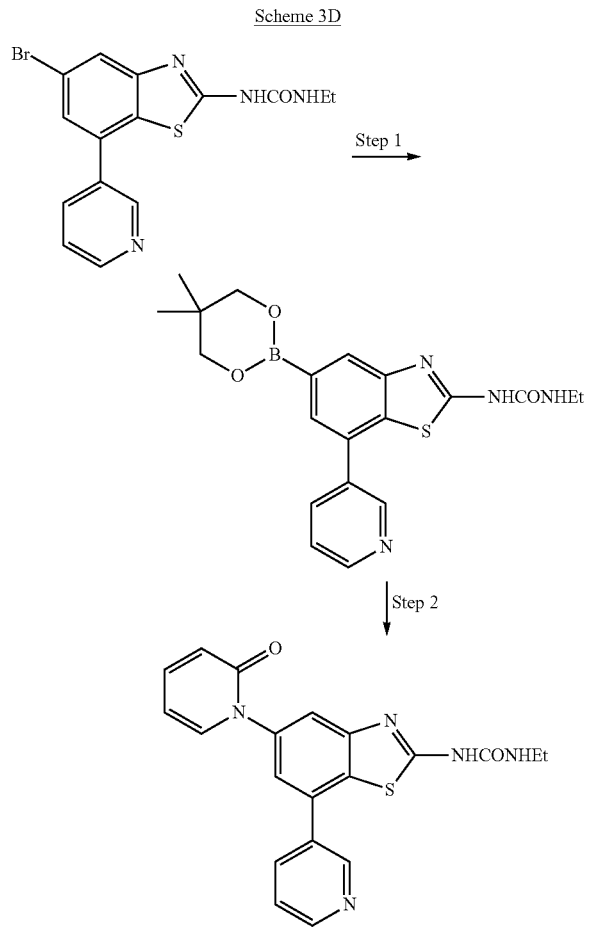

Scheme 3D

Step 1. 1-[5-(5,5-Dimethyl-[1,3,2]dioxaborinan-2-yl)-7-pyridin-3-yl-benzothiazol-2-yl]-3-ethyl-urea A stirred mixture of 1-(5-bromo-7-pyridin-3-yl-benzothiazol-2-yl)-3-ethyl-urea (100 mg, 0.2652 mmol), bis(neopentyl)glycolato diboron (120 mg, 0.5303 mmol) and potassium acetate (78 mg, 0.7957 mmol) in dimethyl sulfoxide (4 ml) was purged with nitrogen for 5 min, treated with 1,1' bis (diphenylphsphino)ferrocene palladium(II)chloride complex (22 mg, 0.02653 mmol) and heated at 80 C. for 16 h. After cooling to ambient temperature, the mixture was diluted with dichloromethane (50 mL), washed with water (3×10 mL), dried over MgSO$_4$ and the solvent removed in vacuo to give the crude 1-[5-(5,5-dimethyl-[1,3,2]dioxaborinan-2-yl)-7-pyridin-3-yl-benzothiazol-2-yl]-3-ethyl-urea which was used in the next step without further purification.

Step 2. 1-Ethyl-3-[5-(2-oxo-2H-pyridin-1-yl)-7-pyridin-3-yl-benzothiazol-2-yl]-urea. [Example 141]

A mixture of the crude 1-[5-(5,5-dimethyl-[1,3,2]dioxaborinan-2-yl)-7-pyridin-3-yl-benzothiazol-2-yl]-3-ethyl-urea, 2-hydroxypyridine (88 mg, 0.292 mmol), copper(II) acetate (56 mg, 0.305 mmol), anhydrous triethylamine (147 mg, 1.458 mmol) and powdered 4A molecular sieves (6 pellets) in anhydrous dichloromethane (21 ml) was stirred in an open vessel at ambient temperature for 5 days. The resultant mixture was filtered and the solvent removed in vacuo to give the crude 1-ethyl-3-[5-(2-oxo-2H-pyridin-1-yl)-7-pyridin-3-yl-benzothiazol-2-yl]-urea which was purified by preparative HPLC. The product was obtained as a brown solid (17 mg).

LC-MS m/z 392 [M+H]$^+$ Rt=2.39 min.

The following were prepared similarly using 1-(5-Bromo-7-pyridin-2-yl-benzothiazol-2-yl)-3-ethyl-urea (Scheme 10):

| ID | NAME | LC-MS DATA |
|---|---|---|
| Example 142 | 1-Ethyl-3-(5-imidazol-1-yl-7-pyridin-2-yl-benzothiazol-2-yl)-urea | m/z 365 [M + H]$^+$ Rt = 2.21 min. |

Scheme 4

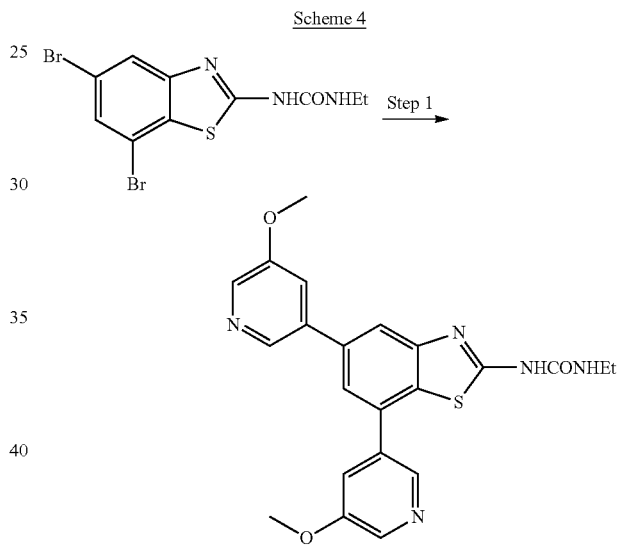

Step 1. 1-[5,7-Bis-(5-methoxy-pyridin-3-yl)-benzothiazol-2-yl]-3-ethyl-urea. [Example 143]

A stirred mixture of 1-(5,7-dibromo-benzothiazol-2-yl-3-ethyl urea (100 mg, 0.264 mmol), powdered potassium phosphate tribasic (67 mg, 0.317 mmol), (1,1'-bis(diphenylphosphino)ferrocene)dichloro-palladium(II) chloride (32 mg, 0.0386 mmol), 3-methoxy-5-pyridineboronic acid pinacol ester (248 mg, 1.056 mmol) in anhydrous 1,4-dioxane (1.8 ml) and anhydrous methanol (3.6 ml) was purged with nitrogen for 5 min and heated at 80° C. for 16 h. The reaction mixture was filtered through celite and washed through with ethyl acetate. The filtrate was evaporated in vacuo to afford the crude 1-[5,7-Bis-(5-methoxy-pyridin-3-yl)-benzothiazol-2-yl]-3-ethyl-urea which was purified by preparative HPLC to give a dark brown solid (20 mg, 17%).

$^1$HNMR (400 MHz, δ, D$_6$DMSO) 1.12 (3H, t), 2.58 (6H, s), 3.22 (2H, m) 7.03 (1H, m), 7.77 (1H, s), 7.80 (1H, s), 7.84 (1H, s), 8.08 (1H, s), 8.25 (1H, s) 8.46 (1H d), 8.46 (1H, d), 8.65 (1H, s), 8.69 (1H, s).

LC-MS m/z 436 [M+H]$^+$ Rt=2.52 min.

The following were prepared similarly:

| ID | NAME | LC-MS DATA |
|---|---|---|
| Example 144 | 1-[5,7-Bis-(4-hydroxymethyl-phenyl)-benzothiazol-2-yl]-3-ethyl-urea | m/z 434 [M + H]$^+$ Rt = 2.90 min |
| Example 145 | 1-[5,7-Bis-(2-amino-pyrimidin-5-yl)-benzothiazol-2-yl]-3-ethyl-urea | m/z 408 [M + H]$^+$ Rt = 2.18 min |
| Example 146 | 1-[5,7-Bis-(4-morpholin-4-ylmethyl-phenyl)-benzothiazol-2-yl]-3-ethyl-urea | m/z 572 [M + H]$^+$ Rt = 1.90 min |
| Example 147 | 1-(5,7-Di-pyrimidin-5-yl-benzothiazol-2-yl)-3-ethyl-urea | m/z 378 [M + H]$^+$ Rt = 2.47 min |
| Example 148 | N-{5-[7-(6-Acetylamino-pyridin-3-yl)-2-(3-ethyl-ureido)-benzothiazol-5-yl]-pyridin-2-yl}-acetamide | m/z 490 [M + H]$^+$ Rt = 2.58 min |

Step 1. 4-Bromo-2,6-dinitroaniline

A stirred suspension of 2,6-dinitroaniline (5 g, 27.3 mmol) in glacial acetic acid (50 ml) was treated, dropwise, with bromine (1.5 ml, 30 mmol) and heated at 120° C. for 2 h. After cooling to ambient temperature, the resultant mixture was poured into water (500 ml). The precipitated solid was collected by filtration, washed with water and dried in vacuo to give 4-Bromo-2,6-dinitroaniline as a yellow solid (6.5 g, 91%).

$^1$H NMR (400 MHz, δ, CDCl$_3$): 8.45 (2H, br s), 8.65 (2H, s).

Step 2. 2,6-Dinitro-4-pyridin-3-yl-aniline

A stirred solution of 4-Bromo-2,6-dinitroaniline (3 g, 11.45 mmol) in 1,2-dimethoxyethane (83 ml) was purged with nitrogen for 15 min and treated with aqueous sodium hydrogen carbonate solution (1M, 22.8 ml) followed by pyridine 3-boronic acid (2.1 g, 17.17 mmol) and 1,1-bis-(diphenylphosphino)ferrocene palladium (II) chloride complex (0.94 g, 1.15 mmol). The resultant mixture was boiled under reflux in a nitrogen atmosphere for 18 h. After cooling to ambient temperature, the dark mixture was diluted with saturated aqueous sodium hydrogen carbonate solution (300 ml) and extracted with ethyl acetate (3×250 ml). This was dried (MgSO$_4$) and the solvent removed in vacuo to give a residue which was purified by flash chromatography (silica) eluting with 30% to 100% ethyl acetate in 40-60 petroleum ether. The 2,6-Dinitro-4-pyridin-3-yl-aniline was obtained as a yellow solid (1.46 g, 49%).

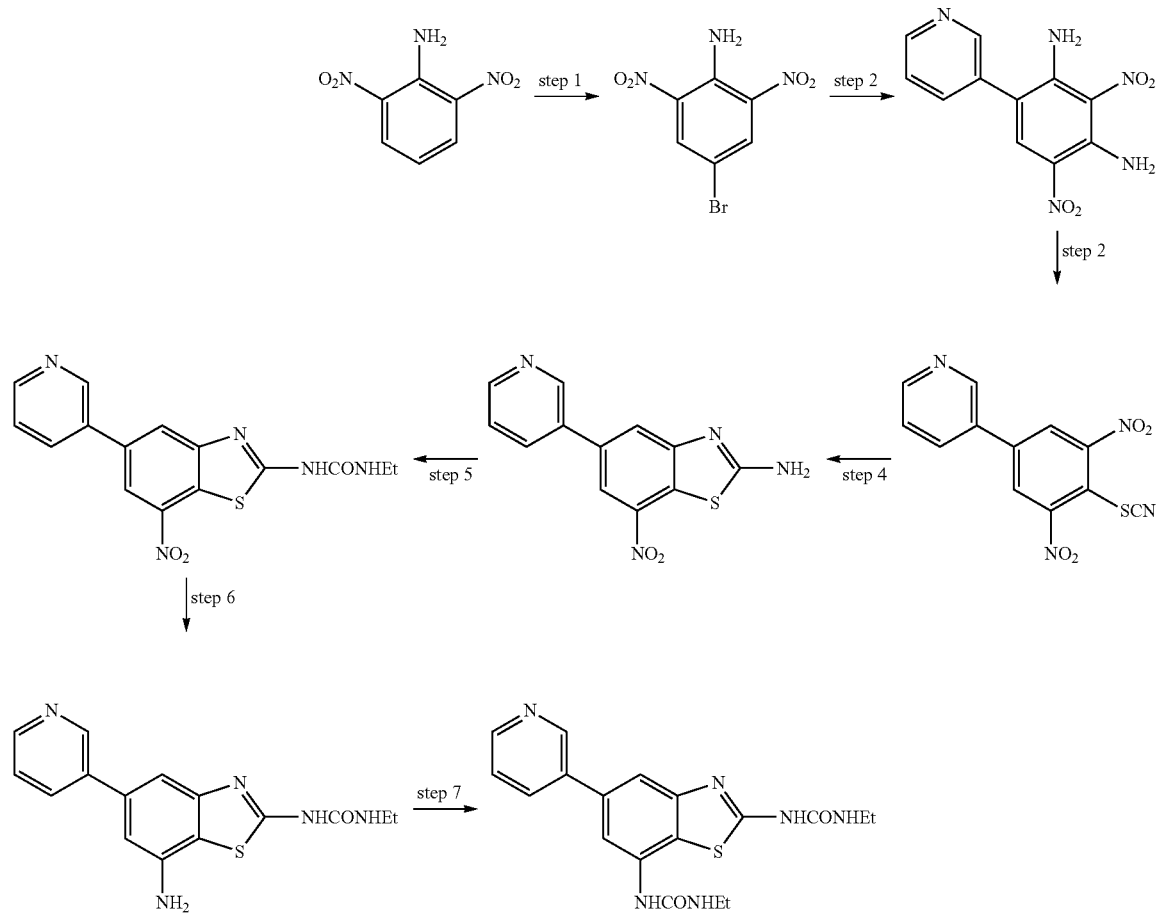

Scheme 5

¹H NMR (400 MHz, δ, CDCl₃): 7.44 (1H, m), 7.90 (1H, m), 8.56 (2H, br s), 8.68 (1H, m), 8.80 (2H, s), 8.87 (1H, d).

Step 3.
3-(3,5-Dinitro-4-thiocyanato-phenyl)-pyridine

A suspension of 2,6-Dinitro-4-pyridin-3-yl-aniline (1.24 g, 4.76 mmol) in aqueous sulfuric acid (50% v/v, 12 ml) was stirred at ambient temperature for 1 h before being cooled in an ice bath and treated over 5 min with an aqueous sodium nitrite solution (20% w/v, 2.0 ml). The mixture was stirred in the cold for 1.5 h before being treated with a solution of potassium thiocyanate (0.6 g) in water (1.4 ml) in one portion. The resultant mixture was stirred in the cold for 15 min and then added to a suspension of copper (I) thiocyanate (1.0 g) in water (4 ml) whilst cooling in an ice-bath. The mixture was stirred in the cold for 2 h and then heated to 70° C. for 20 min. After cooling to ambient temperature, the mixture was poured into a saturated aqueous solution of sodium hydrogen carbonate (200 ml) and extracted with ethyl acetate (3×100 ml) which was washed with brine (200 ml) and dried (MgSO₄). The solvent was removed in vacuo to give a residue which was purified by flash chromatography (silica) eluting with 80% to 100% ethyl acetate in 40-60 petroleum ether. The 3-(3,5-Dinitro-4-thiocyanato-phenyl)-pyridine was obtained as a yellow solid (1.07 g, 74%).

¹H NMR (400 MHz, δ, CDCl₃): 7.54 (1H, m), 7.99 (1H, m), 8.49 (2H, s), 8.82 (1H, m), 8.95 (1H, d).

Step 4.
7-Nitro-5-pyridin-3-yl-benzothiazol-2-ylamine

A solution of 3-(3,5-Dinitro-4-thiocyanato-phenyl)-pyridine (0.66 g, 2.19 mmol) in glacial acetic acid (15 ml) was treated with iron powder (0.61 g, 11.0 mmol) and stirred at ambient temperature for 16 h. The resultant mixture was diluted with water (200 ml) and made alkaline by the addition of concentrated ammonia solution. The solid material was collected by filtration and washed with water followed by ethyl acetate. The filtered solid was then extracted with boiling ethanol (3×200 ml) which was removed in vacuo to give 7-Nitro-5-pyridin-3-yl-benzothiazol-2-ylamine as a pale yellow solid (0.57 g, 95%).
LC-MS m/z 273 [M+H]⁺ Rt=2.24 min.

Step 5. 1-Ethyl-3-(7-nitro-5-pyridin-3-yl-benzothiazol-2-yl)-urea

A stirred mixture of 7-Nitro-5-pyridin-3-yl-benzothiazol-2-ylamine (100 mg, 0.3676 mmol), ethyl isocyanate (0.18 ml, 1.831 mmol) and dibutyltindiacetate (10 drops) in anhydrous 1,4-dioxane (10 ml) was heated in a sealed vessel at 100° C. for 16 h. After cooling to ambient temperature, the precipitated solid was collected by filtration, washed with 1,4-doxane and dried in vacuo to give 1-Ethyl-3-(7-nitro-5-pyridin-3-yl-benzothiazol-2-yl)-urea as a yellow solid (30 mg, 24%).
LC-MS m/z 344 [M+H]⁺ Rt=2.59 min.

Step 6. 1-(7-Amino-5-pyridin-3-yl-benzothiazol-2-yl)-3-ethyl-urea. [Example 149]

A stirred suspension of 1-Ethyl-3-(7-nitro-5-pyridin-3-yl-benzothiazol-2-yl)-urea (25 mg, 0.0728 mmol) in ethanol (0.5 ml) and concentrated hydrochloric acid (0.5 ml) was treated with tin (II) chloride (69 mg, 0.364 mmol) and heated at 80° C. for 5 h. After cooling to ambient temperature, the mixture was diluted with water (50 ml) and made alkaline (pH 11) by the addition of concentrated ammonia. The 1-(7-Amino-5-pyridin-3-yl-benzothiazol-2-yl)-3-ethyl-urea was extracted with ethyl acetate (3×50 ml) which was dried (MgSO4) and the solvent removed in vacuo to give an off-white solid (37 mg) which was used without further purification.
¹H NMR (400 MHz, δ, D₆DMSO): 1.14 (3H, t), 3.24 (2H, m), 5.63 (2H, br s), 6.79 (1H, br t), 6.80 (1H, s), 7.22 (1H, br s), 7.50 (1H, m), 8.03 (1H, d), 8.58 (1H, d), 8.86 (1H, s), 10.62 (1H, br s).

Step 7. 1-Ethyl-3-[2-(3-ethyl-ureido)-5-pyridin-3-yl-benzothiazol-7-yl]-urea. [Example 150]

A stirred mixture of 1-(7-Amino-5-pyridin-3-yl-benzothiazol-2-yl)-3-ethyl-urea (15 mg, 0.048 mmol), ethyl isocyanate (0.03 ml) and dibutyltindiacetate (2 drops) in anhydrous 1,4-dioxane (2 ml) was heated in a sealed vessel at 100° C. for 16 h. After cooling to ambient temperature, the 1-Ethyl-3-[2-(3-ethyl-ureido)-5-pyridin-3-yl-benzothiazol-7-yl]-urea was isolated by Preparative HPLC as a white solid (5.4 mg, 29%).
¹H NMR (400 MHz, δ, CD₃OD): 1.23 (6H, m), 3.29 (4H, m), 7.56 (1H, m), 7.66 (1H, s), 7.79 (1H, s), 8.16 (1H, d), 8.43 (1H, br s), 8.55 (1H, br s), 8.87 (1H, br s).
LC-MS m/z 385 [M+H]⁺ Rt=2.00 min.

Scheme 6

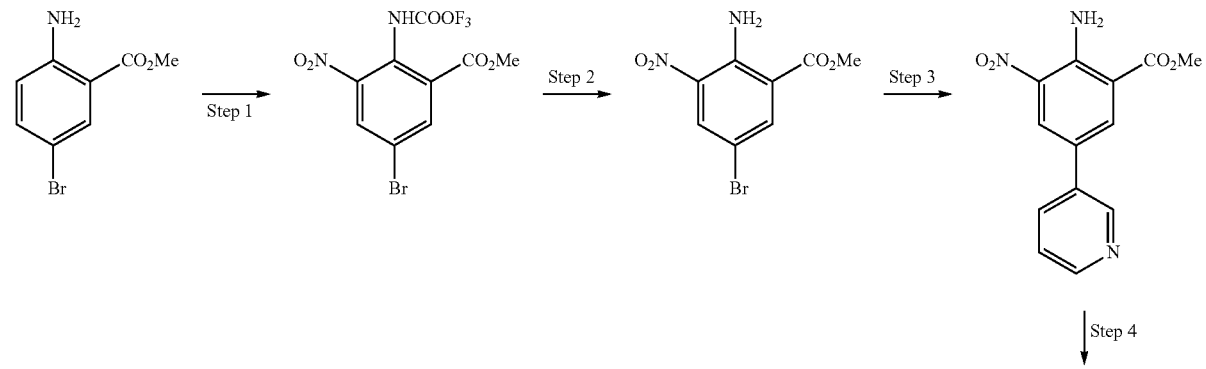

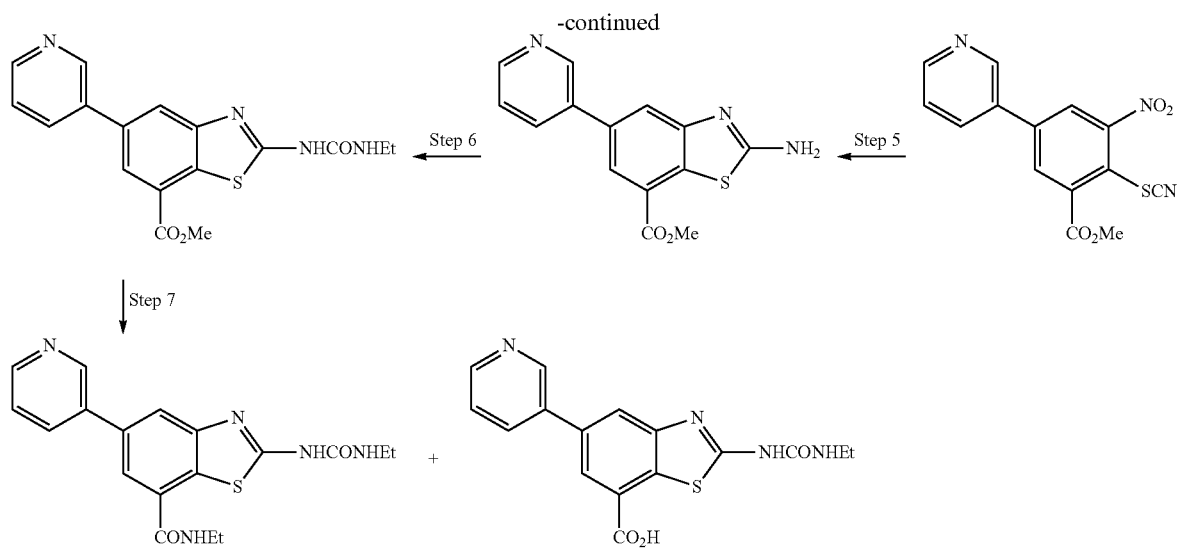

Step 1. 5-Bromo-3-nitro-2-(2,2,2-trifluoro-acetylamino)-benzoic acid methyl ester Stirred trifluoroacetic anhydride (120 ml) was cooled in an ice-salt bath and treated, over 5 min, with methyl-2-amino-5-bromobenzoate (10 g, 43.5 mmol), keeping the temperature below 6° C. When the addition was complete, the resultant suspension was stirred in the cold for a further 15 min when potassium nitrate (5.27 g, 52.2 mmol) was added in one portion. The reaction mixture was allowed to come to ambient temperature and stirred for 16 h. The resultant mixture was concentrated by evaporation, the residue diluted with saturated aqueous sodium hydrogen carbonate solution (300 ml) and extracted with ethyl acetate (3×250 ml) which was washed with brine (300 ml) and dried (MgSO$_4$). The solvent was removed in vacuo to give the crude product which was purified by flash chromatography (silica) eluting with 10% to 90% ethyl acetate in 40-60 petroleum ether. A byproduct (5-Bromo-2-(2,2,2-trifluoro-acetylamino)-benzoic acid methyl ester) was eluted before the 5-Bromo-3-nitro-2-(2,2,2-trifluoro-acetylamino)-benzoic acid methyl ester which was obtained as a yellow solid (11.1 g, 69%).

$^1$H NMR (400 MHz, δ, CDCl$_3$): 4.03 (3H, s), 7.26 (1H, s), 8.33 (1H, d), 8.44 (1H, d), 11.23 (1H, br s).

Step 2. 2-Amino-5-bromo-3-nitro-benzoic acid methyl ester

A stirred suspension of 5-Bromo-3-nitro-2-(2,2,2-trifluoro-acetylamino)-benzoic acid methyl ester (8 g, 21.56 mmol) in methanol (150 ml) was treated with hydrochloric acid (6M, 75 ml) and heated at 80° C. for 16 h. After cooling to ambient temperature, the yellow solid was collected by filtration and washed with cold water and dried in vacuo to give 2-Amino-5-bromo-3-nitro-benzoic acid methyl ester (5.0 g, 84%).

$^1$H NMR (400 MHz, δ, CDCl$_3$): 3.99 (3H, s), 8.33 (1H, d), 8.40 (2H, br s), 8.51 (1H, d).

Step 3. 2-Amino-3-nitro-5-pyridin-3-yl-benzoic acid methyl ester

A stirred solution of 2-Amino-5-bromo-3-nitro-benzoic acid methyl ester (2 g, 7.27 mmol) in 1,2-dimethoxyethane (53 ml) was purged with nitrogen for 15 min and treated with aqueous sodium hydrogen carbonate solution (1M, 14.5 ml) followed by pyridine 3-boronic acid (1.33 g, 10.9 mmol) and 1,1-bis-(diphenylphosphino)ferrocene palladium (II) chloride complex (0.6 g, 0.733 mmol). The resultant mixture was boiled under reflux in a nitrogen atmosphere for 18 h. After cooling to ambient temperature, the dark mixture was diluted with saturated aqueous sodium hydrogen carbonate solution (300 ml) and extracted with ethyl acetate (3×250 ml). This was washed with brine (200 ml), dried (MgSO$_4$) and the solvent removed in vacuo to give a residue which was purified by flash chromatography (silica) eluting with 30% to 100% ethyl acetate in 40-60 petroleum ether. The 2-Amino-3-nitro-5-pyridin-3-yl-benzoic acid methyl ester was obtained as a yellow solid (1.1 g, 56%).

$^1$H NMR (400 MHz, δ, CDCl$_3$): 3.97 (3H, s), 7.39 (1H, m), 7.87 (1H, m), 8.52 (1H, d), 8.55 (2H, br s), 8.62 (1H, m), 8.65 (1H, d), 8.84 (1H, m).

Step 4. 3-Nitro-5-pyridin-3-yl-2-thiocyanato-benzoic acid methyl ester

A suspension of 2-Amino-3-nitro-5-pyridin-3-yl-benzoic acid methyl ester (0.92 g, 3.37 mmol) in aqueous sulfuric acid (50% v/v, 9 ml) was stirred at ambient temperature for 1 h before being cooled in an ice bath and treated over 5 min with an aqueous sodium nitrite solution (20% w/v, 1.4 ml). The mixture was stirred in the cold for 1.5 h before being treated with a solution of potassium thiocyanate (0.42 g) in water (1.0 ml) in one portion. The resultant mixture was stirred in the cold for 15 min and then added to a suspension of copper (I) thiocyanate (0.71 g) in water (2.8 ml) whilst cooling in an ice-bath. The mixture was stirred in the cold for 2 h and then heated to 70° C. for 20 min. After cooling to ambient temperature, the mixture was poured into a saturated aqueous solution of sodium hydrogen carbonate (200 ml) and extracted with ethyl acetate (3×100 ml) which was washed with brine (200 ml) and dried (MgSO$_4$). The solvent was removed in vacuo to give a residue which was purified by flash chromatography (silica) eluting with 80% to 100% ethyl acetate in 40-60 petroleum ether. The 3-Nitro-5-pyridin-3-yl-2-thiocyanato-benzoic acid methyl ester was obtained as a pale yellow solid (0.78 g, 74%).

$^1$H NMR (400 MHz, δ, CDCl$_3$): 4.12 (3H, s), 7.49 (1H, m), 7.96 (1H, m), 8.34 (1H, d), 8.40 (1H, d), 8.76 (1H, m), 8.92 (1H, d).

Step 5. 2-Amino-5-pyridin-3-yl-benzothiazole-7-carboxylic acid methyl ester

A solution of 3-Nitro-5-pyridin-3-yl-2-thiocyanato-benzoic acid methyl ester (1.1 g, 3.49 mmol) in glacial acetic acid (23 ml) was treated with iron powder (0.97 g, 17.5 mmol) and stirred at ambient temperature for 16 h. The resultant mixture was diluted with water (200 ml) and made alkaline by the addition of concentrated ammonia solution. The mixture was filtered and the filtrate extracted with ethyl acetate (3×200 ml). The filtered solid was extracted with boiling ethanol (3×250 ml) and the combined organic fractions evaporated to dryness to give 2-Amino-5-pyridin-3-yl-benzothiazole-7-carboxylic acid methyl ester as an off-white solid (0.46 g, 46%).

$^1$H NMR (400 MHz, δ, D$_6$DMSO): 3.98 (3H, s), 7.55 (1H, m), 7.81 (2H, br s), 7.95 (2H, s), 8.18 (1H, m), 8.64 (1H, m), 8.98 (1H, s).

Step 6. 2-(3-Ethyl-ureido)-5-pyridin-3-yl-benzothiazole-7-carboxylic acid methyl ester. [Example 151]

A stirred mixture of 2-Amino-5-pyridin-3-yl-benzothiazole-7-carboxylic acid methyl ester (20 mg, 0.07 mmol), ethyl isocyanate (0.03 ml, 0.35 mmol) and dibutyltindiacetate (2 drops) in anhydrous 1,4-dioxane (1.5 ml) was heated by microwave irradiation in a CEM Discover reactor at 125° C. for 1 h. After cooling to ambient temperature, the 2-(3-Ethyl-ureido)-5-pyridin-3-yl-benzothiazole-7-carboxylic acid methyl ester was isolated by Preparative HPLC as a white solid (7.4 mg, 30%).

$^1$H NMR (400 MHz, δ, CDCl$_3$+CD$_3$OD): 1.26 (3H, t), 3.38 (2H, m), 4.06 (3H, s), 7.51 (1H, m), 8.06 (1H, d), 8.08 (1H, m), 8.19 (1H, d), 8.59 (1H, m), 8.88 (1H, d).

LC-MS m/z 357 [M+H]$^+$ Rt=2.25 min

Step 7. 2-(3-Ethyl-ureido)-5-pyridin-3-yl-benzothiazole-7-carboxylic acid ethylamide [Example 152] and 2-(3-Ethyl-ureido)-5-pyridin-3-yl-benzothiazole-7-carboxylic acid A stirred mixture of 2-Amino-5-pyridin-3-yl-benzothiazole-7-carboxylic acid methyl ester (125 mg, 0.439 mmol), ethyl isocyanate (0.21 ml, 2.187 mmol) and dibutyltindiacetate (12 drops) in anhydrous 1,4-dioxane (10 ml) was heated in a sealed vessel at 100° C. for 16 h. After cooling to ambient temperature, the solvent was removed in vacuo to give 2-(3-Ethyl-ureido)-5-pyridin-3-yl-benzothiazole-7-carboxylic acid methyl ester which was used without further purification. A stirred mixture of 2-(3-Ethyl-ureido)-5-pyridin-3-yl-benzothiazole-7-carboxylic acid methyl ester (78 mg, 0.22 mmol) and aqueous ethylamine solution (70% w/v, 3 ml) was heated by microwave irradiation in a CEM Discover reactor at 100° C. for 1 h. The reaction mixture was purified by Preparative HPLC to provide the 2-(3-Ethyl-ureido)-5-pyridin-3-yl-benzothiazole-7-carboxylic acid ethylamide as a white solid (8.7 mg, 5%).

$^1$H NMR (400 MHz, δ, CDCl$_3$+CD$_3$OD): 1.28 (6H, m), 3.40 (2H, m), 3.53 (2H, m), 7.51 (1H, m), 7.99 (2H, d), 8.12 (1H, d), 8.35 (1H, br d), 8.57 (1H, br s), 8.91 (1H, s).

LC-MS m/z 370 [M+H]$^+$ Rt=2.05 min.

2-(3-Ethyl-ureido)-5-pyridin-3-yl-benzothiazole-7-carboxylic acid was also isolated as a white solid (2.5 mg, 2%).

LC-MS m/z 343 [M+H]$^+$ Rt=1.91 min.

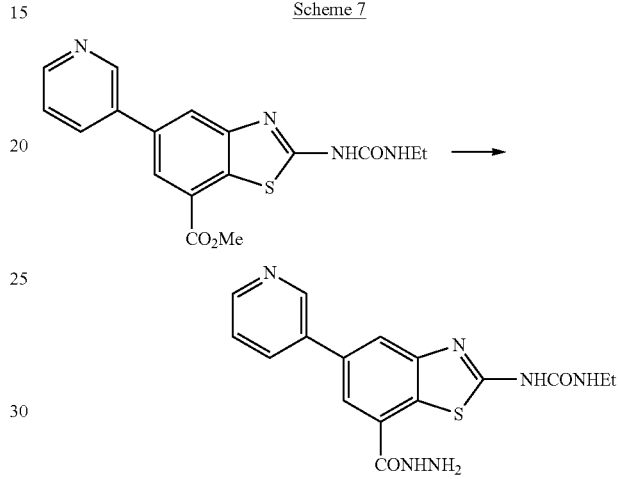

Scheme 7

1-Ethyl-3-(7-hydrazinocarbonyl-5-pyridin-3-yl-benzothiazol-2-yl)-urea. [Example 153]

A suspension of 2-(3-Ethyl-ureido)-5-pyridin-3-yl-benzothiazole-7-carboxylic acid methyl ester (319 mg, 0.895 mmol) in methanol (10 ml) was treated with hydrazine hydrate (2 ml) and stirred at ambient temperature for 16 h. HPLC indicated that the reaction mixture still contained a considerable amount of starter so a further 1 ml of hydrazine hydrate was added and the stirring continued for a further 24 h. The resultant mixture was diluted with water (50 ml) and the solid collected by filtration. This was washed with water (25 ml) followed by ethanol (25 ml) and dried in vacuo to give 1-Ethyl-3-(7-hydrazinocarbonyl-5-pyridin-3-yl-benzothiazol-2-yl)-urea as an off-white solid (312 mg, 98%).

$^1$H NMR (400 MHz, δ, D$_6$DMSO): 1.15 (3H, t), 3.26 (2H, m), 4.69 (2H, br s), 6.86 (1H, br t), 7.57 (1H, m), 8.15 (1H, s), 8.22 (1H, s), 8.29 (1H, d), 8.65 (1H, d), 9.12 (1H, s), 10.24 (1H, br s), 10.71 (1H, br s).

LC-MS m/z 357 [M+H]$^+$ Rt=2.22 min.

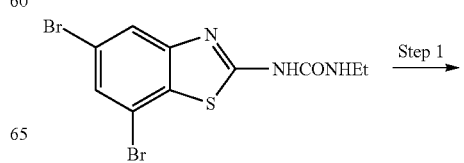

Scheme 9

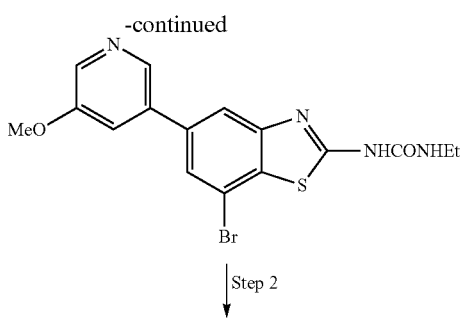

Step 2 ↓

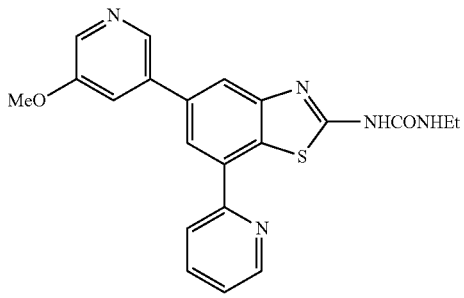

Step 1-[7-Bromo-5-(5-methoxy-pyridin-3-yl)-benzothiazol-2-yl]-3-ethyl-urea

A stirred mixture of 1-(5,7-dibromo-benzothiazol-2-yl-3-ethyl urea (300 mg, 0.79 mmol), sodium carbonate (167 mg, 1.58 mmol), (1,1′-bis(diphenylphosphino)ferrocene) dichloro-palladium(II) (45 mg, 0.05 mmol), 3-methoxy-5-pyridineboronic acid pinacol ester (186 mg, 0.79 mmol) in dimethyl formamide (8 ml) and water (2 ml), was purged with nitrogen for 5 min and heated at 100° C. for 1 h. The reaction mixture was concentrated in vacuo then partitioned between ethyl acetate and water. The organic phase was dried ($MgSO_4$), filtered and concentrated in vacuo. The crude material was purified by silica gel chromatography eluting with 0 to 5% methanol in ethyl acetate to give 1-[7-Bromo-5-(5-methoxy-pyridin-3-yl)-benzothiazol-2-yl]-3-ethyl-urea 1 as a white solid (49 mg, 15%).

$^1$HNMR (400 MHz, δ, $CDCl_3$) 1.25 (3H, t), 3.39 (2H, q), 3.98 (3H, s), 7.42 (1H, s), 7.50 (1H, m), 7.58 (1H, s), 7.67 (1H, m), 7.80 (1H, s), 8.29 (1H, s) 8.42 (1H, s).

LC-MS m/z 407 and 409 $[M+H]^+$ (79 Br and 81 Br). Rt=3.22 min

Step 2. 1-Ethyl-3-[5-(5-methoxy-pyridin-3-yl)-7-pyridin-2-yl-benzothiazol-2-yl]-urea [Example 179]

To a stirred solution of 1-[7-Bromo-5-(5-methoxy-pyridin-3-yl)-benzothiazol-2-yl]-3-ethyl-urea (90 mg, 0.22 mmol), and bis(triphenylphosphine)palladium(II) chloride (10 mg, 0.015 mmol), in tetrahydrofuran (4 ml), was added 2-pyridylzinc bromide (3.1 ml, 1.5 mmol, 0.5 M solution in THF). The reaction was purged with nitrogen then heated at 60° C. for 16 h. The reaction mixture was diluted with ethyl acetate and washed with saturated aqueous ammonium chloride solution followed by brine. The organic phase was dried ($MgSO_4$), filtered and concentrated in vacuo. The crude material was purified by preparative HPLC to give 1-Ethyl-3-[5-(5-methoxy-pyridin-3-yl)-7-pyridin-2-yl-benzothiazol-2-yl]-urea as a white solid (25 mg, 27%)

$^1$HNMR (400 MHz, δ, $CDCl_3$) 1.31 (3H, t), 3.48 (2H, q), 3.90 (3H, s), 7.21 (1H, m), 7.50 (1H, s), 7.80 (1H, m), 8.32 (1H, s), 8.57 (1H, br s), 8.60 (1H, s) 10.52 (1H, br s).

LC-MS m/z 406 $[M+H]^+$. Rt=2.91 min.

The following were prepared similarly using 1-[5-(2-Amino-pyrimidin-5-yl)-7-bromo-benzothiazol-2-yl]-3-ethyl-urea (Scheme 1):

| ID | NAME | LC/MS DATA |
|---|---|---|
| Example 154 | 1-[5-(2-Amino-pyrimidin-5-yl)-7-pyridin-2-yl-benzothiazol-2-yl]-3-ethyl-urea | m/z 392 $[M + H]^+$ Rt = 2.74 min. |

Scheme 9A

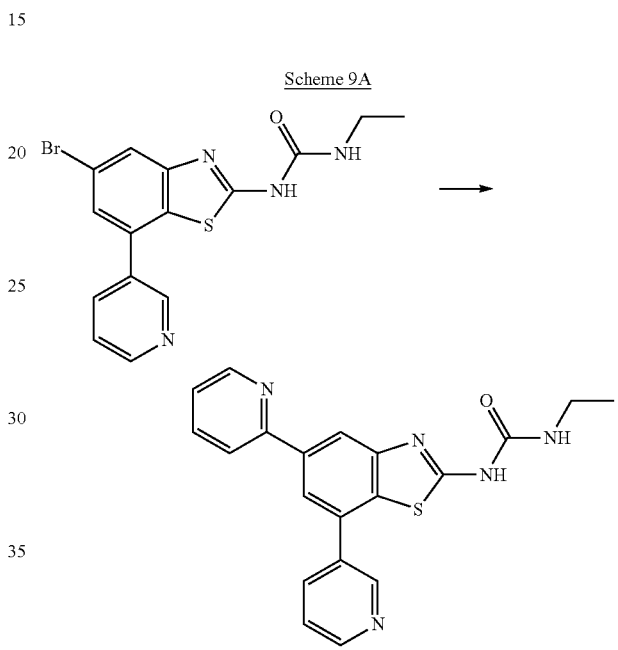

1-Ethyl-3-(5-pyridin-2-yl-7-pyridin-3-yl-benzothiazol-2-yl)-urea. [Example 155]

To a solution of 1-(5-bromo-7-pyridin-3-yl-benzothiazol-2-yl)-3-ethyl-urea (0.20 g, 0.53 mmol) in DMF (5 mL) was added 2-tributylstannyl pyridine (0.23 g, 0.53 mmol) under nitrogen atmosphere at room temperature. The reaction mixture was then degassed for half an hour followed by the addition of tetrakis(triphenylphosphine)palladium(0) (0.061 g, 0.053 mmol). The reaction mixture was then again degassed and heated at 120° C. for 8 h under nitrogen atmosphere. After the completion of the reaction (TLC monitoring), DMF was distilled off; water was added to the reaction mixture and extracted with ethyl acetate. The combined organic layers were dried over anhydrous $Na_2SO_4$, and evaporated to dryness under reduced pressure. The crude residue was purified over silica gel (230-400 M) using EtOAc-Hexane (80:20) to provide the title compound as off white solid (0.012 g, 6%).

$^1$H NMR (DMSO-$d_6$, 400 MHz): δ 1.08 (t, J=7.20 Hz, 3H), 3.10-3.20 (m, 2H), 6.73 (s, 3H), 7.37-7.40 (m, 1H), 7.60-7.63 (m, 1H), 7.87-.7.93 (m, 1H), 8.07 (s, 1H), 8.17-8.21 (m, 1H), 8.38 (s, 1H), 8.69-8.70 (m, 1H), 8.98 (m, 1H), and 10.78 (br s, 1H). MS: 376.09 $(M+H^+)$.

Scheme 9B

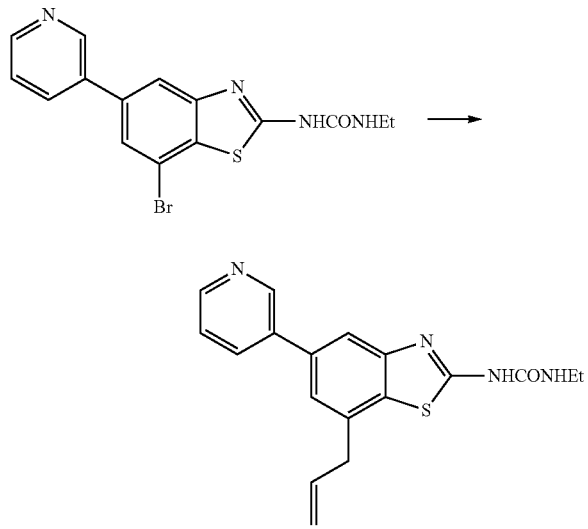

1-(7-Allyl-5-pyridin-3-yl-benzothiazol-2-yl)-3-ethyl-urea. [Example 156]

To a solution of 1-(7-bromo-5-pyridin-3-yl-benzothiazol-2-yl)-3-ethyl-urea (0.14 g, 0.37 mmol) in DMF (2 mL) was added tributylallyltin (0.15 g, 0.45 mmol) under nitrogen atmosphere at room temperature. The reaction mixture was then degassed for half an hour followed by the addition of tetrakis(triphenylphosphine)palladium(0) (0.043 g, 0.0371 mmol). The reaction mixture was then again degassed for half an hour and heated at 120° C. for 20 h under nitrogen atmosphere. After the completion of the reaction (TLC monitoring), DMF was distilled off; water was added to the reaction mixture and extracted with ethyl acetate (×3). The combined organic layer was dried over anhydrous $Na_2SO_4$, and evaporated to dryness under reduced pressure. The crude residue was purified over silica gel (230-400 M) using EtOAc-MeOH (95:5) to provide the title compound as off white solid (0.034 g, 27%).

$^1$H NMR (DMSO-d6, 400 MHz): δ 1.09 (t, J=7.2 Hz, 3H), 3.12-3.28 (m, 2H), 3.65 (m, 2H), 5.14-5.23 (m, 2H), 5.97-6.07 (m, 1H), 6.74 (br s, 1H), 7.43 (s, 1H), 7.47-7.50 (m, 1H), 7.83 (s, 1H), 8.12 (d, J=7.6 Hz, 1H), 8.56-8.57 (m, 1H), 8.93-8.94 (m, 1H) and 10.77 (br s, 1H). MS: 337.13 (M−H).

The following were prepared similarly:

| ID | NAME | NMR/LC-MS DATA |
|---|---|---|
| Example 157 | 1-Ethyl-3-[7-(2-methoxy-thiazol-4-yl)-5-pyridin-3-yl-benzothiazol-2-yl]-urea | $^1$H NMR (DMSO-d$_6$, 400 MHz): δ 1.10 (t, J = 7.2 Hz, 3H), 3.15-3.25 (m, 2H), 4.20 (s, 3H), 6.80 (br s, 1H), 7.51-7.54 (m, 1H), 7.91-2 (d, J = 5.2 Hz, 1H), 7.94 (s, 1H), 7.99 (d, J = 8.4 Hz, 1H), 8.13 (d, J = 7.8 Hz, 1H), 8.56-8.57 (m, 1H), 8.94 (s, 1H), 10.79 (br s, 1H). MS: 410.10 (M − H). |
| Example 158 | 1-Ethyl-3-(5-pyridin-3-yl-7-thiazol-4-yl-benzothiazol-2-yl)-urea | $^1$H NMR (DMSO-d$_6$, 400 MHz): δ 1.11 (t, J = 7.60 Hz, 3H), 3.21 (q, J = 7.20 Hz, 2H), 6.81 (br s, 1H), 7.52-7.55 (m, 1H), 7.96 (s, 1H), 8.21 (s, 1H), 8.28 (d, J = 7.60 Hz, 1H), 8.61 (m, 1H), 8.65 (s, 1H), 9.09 (s, 1H), 9.38 (s, 1H) and 10.69 (br s, 1H). MS: 382.25 (M + H)$^+$. |
| Example 159 | 1-Ethyl-3-(5-pyridin-3-yl-7-pyrimidin-5-yl-benzothiazol-2-yl)-urea | $^1$H NMR (DMSO-d$_6$, 400 MHz): δ 1.08 (t, J = 7.2 Hz, 3H), 3.14-3.18 (m, 2H), 6.77 (br s, 1H), 7.52-7.54 (m, 1H), 7.81 (s, 1H), 8.08 (s, 1H), 8.26-8.28 (m, 1H), 8.60-8.61 (m, 1H), 9.08 (s, 1H), 9.27 (s, 2H), 9.31 (s, 1H) and 10.96 (br s, 1H). MS: 377.14 (M + H$^+$). |
| Example 160 | 1-Ethyl-3-(7-pyridazin-3-yl-5-pyridin-3-yl-benzothiazol-2-yl)-urea | $^1$H NMR (DMSO-d$_6$, 400 MHz): δ 1.09 (t, J = 7.2 Hz, 3H), 3.18 (t, J = 6.4 Hz, 2H), 6.79 (br s, 1H), 7.53-7.54 (m, 1H), 7.90 (s, 1H), 8.13-8.15 (m, 2H), 8.28-8.30 (m, 1H), 8.62 (s, 1H), 9.10 (s, 1H), 9.42-9.44 (m, 1H), 9.75 (s, 1H) and 11.01 (br s, 1H). MS: 375.07 (M − H). |
| Example 161 | 1-Ethyl-3-(5-pyridin-3-yl-7-thiazol-5-yl-benzothiazol-2-yl)-urea | $^1$H NMR (DMSO-d$_6$, 400 MHz): δ 1.10 (t, J = 7.20 Hz, 3H), 3.19 (q, J = 7.20 Hz, 2H), 6.76 (br s, 1H), |

-continued

| ID | NAME | NMR/LC-MS DATA |
|---|---|---|
| | | 7.51-7.54 (m, 1H), 7.89 (s, 1H), 8.00 (s, 1H), 8.26 (d, J = 8.0 Hz, 1H), 8.54 (s, 1H), 8.60 (br s, 1H), 9.05 (s, 1H), 9.28 (s, 1H) and 10.96 (br s, 1H). MS: 382.11 (M + H)$^+$. |
| Example 162 | 1-Ethyl-3-[7-(1-methyl-1H-imidazol-2-yl)-5-pyridin-3-yl-benzothiazol-2-yl]-urea | $^1$H NMR (DMSO-d$_6$, 400 MHz): δ 1.08 (t, J = 7.2 Hz, 3H), 3.10-3.13 (m, 2H), 3.24 (s, 3H), 5.80 br s, 1H), 6.80 (br s, 1H), 7.26 (s, 1H), 7.48-7.52 (m, 1H), 7.59 (s, 1H), 7.83 (s, 1H), 7.95 (s, 1H), 8.19-8.21 (d, J = 7.2 Hz, 1H), 8.58-8.59 (d, J = 6.4 Hz, 1H) and 9.00 (s, 1H). MS: 379.18 (M + H)$^+$. |
| Example 163 | 1-Ethyl-3-(5-pyridin-3-yl-7-pyridin-2-yl-benzothiazol-2-yl)-urea | $^1$H NMR (DMSO-d$_6$, 400 MHz): δ 1.11 (t, J = 7.20 Hz, 3H), 3.16-3.24 (m, 2H), 7.01 (br s, 1H), 7.44-7.47 (m, 1H), 7.52-7.55 (m, 1H), 8.0 (t, J = 7.60 Hz, 1H), 8.04 (s, 1H), 8.30 (m, 2H), 8.51 (d, J = 8.0 Hz, 1H), 8.62 (m, 1H), 8.82 (m, 1H), 9.12 (s, 1H) and 10.78 (br s, 1H). MS: 376.09 (M + H)$^+$. |
| Example 164 | 1-Ethyl-3-[7-(3-methyl-3H-imidazol-4-yl)-5-pyridin-3-yl-benzothiazol-2-yl]-urea | $^1$H NMR (DMSO-d$_6$, 400 MHz): δ 1.08 (t, J = 7.20 Hz, 3H), 3.17 (q, J = 6.40 Hz, 2H), 3.71 (s, 3H), 6.74 (s, 1H), 7.27 (s, 1H), 7.49-7.52 (m, 1H), 7.61 (s, 1H), 7.85 (s, 1H), 7.97 (s, 1H), 8.19-8.22 (m, 1H), 8.60 (m, 1H), 9.01 (s, 1H) & 10.86 (br s, 1H). MS: 379.24 (M + H)$^+$. Qualitative HPLC Purity (Xbridge C18, 250 × 4.6 mm, 257 nm): 93.82% (Rt = 13.40 min). |
| Example 165 | 1-Ethyl-3-(7-oxazol-2-yl-5-pyridin-3-yl-benzothiazol-2-yl)-urea | MS: 366.24 (M + H)$^+$. Qualitative HPLC Purity (Xbridge C18, 250 × 4.6 mm, 268 nm): 83.86% (Rt = 13.62 min). |

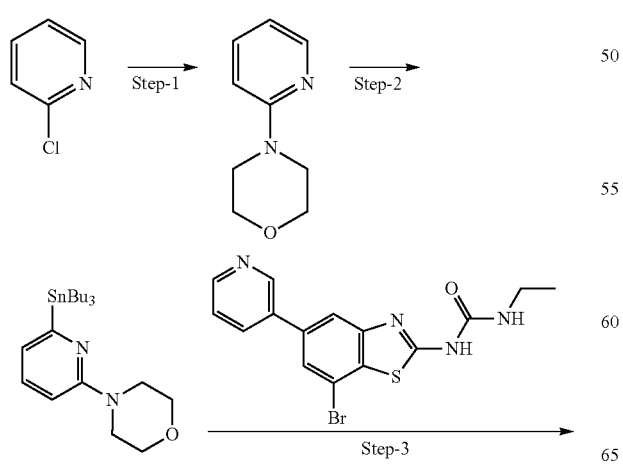

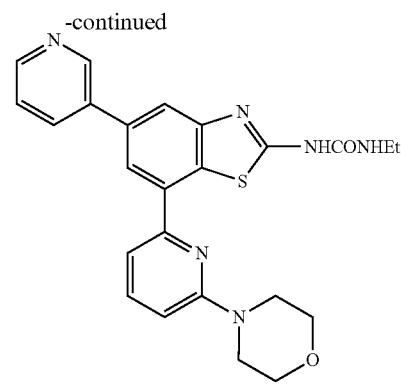

Step-1. 4-Pyridin-2-yl-morpholine

Mixture of 2-chloropyridine (1.0 g, 8.78 mmol), morpholine (1.14 g, 13.18 mmol), NaO$^t$Bu (1.27 g, 13.18 mmol), Pd(OAc)$_2$ (0.098 g, 0.44 mmol) and BINAP (0.12 g, 0.18 mmol) in toluene (10 ml) was degassed for 20 minutes. The reaction mixture was refluxed at 120° C. for 16 h. After completion of reaction (TLC monitoring) toluene was distilled off, water was added to the reaction mass and extracted with ethyl acetate (3×30 mL). The combined organic layers were dried over anhydrous Na$_2$SO$_4$, and evaporated to dryness. The crude residue was purified over silica gel (60-120 M) using EtOAc-Hexane (5:95) to provide the compound as yellow oil (1.10 g, 76%).

$^1$H NMR (DMSO-d$_6$, 400 MHz): δ 3.48-350 (m, 4H), 3.81-3.83 (m, 4H), 6.62-6.67 (m, 2H), 7.47-7.52 (m, 1H), 8.20 (d, J=8.80 Hz, 1H). MS: 165.15 (M+H)$^+$.

Step 2.
4-(6-Tributylstannanyl-pyridin-2-yl)-morpholine

To a solution of 2-dimethylaminoethanol (0.46 mL, 4.56 mmol) in hexane (7.0 mL, HPLC grade) cooled at −5° C. was added drop wise n-BuLi (1.60 M, 5.70 mL, 9.12 mmol) under nitrogen atmosphere. After 30 min at 0° C., 4-pyridin-2-yl-morpholine (0.25 g, 1.52 mmol) in hexane (2.0 mL) was added drop wise. After stirring the reaction mixture for 1 h at 0-5° C., the reaction medium was cooled to −78° C. followed by drop wise addition of tributyl tin chloride (1.03 mL, 3.70 mmol). The resulting reaction mixture was stirred at −78° C. for 30 min and then allowed to stir at 0-5° C. for 2 h. The reaction mixture was then allowed to come to room temperature. After the completion of reaction (TLC monitoring), the reaction mass was cooled to 0° C. and water was added slowly. The aqueous phase was extracted with diethyl ether (3×20 mL). The combined organic layers were dried over anhydrous Na$_2$SO$_4$, and evaporated to dryness. The crude residue was purified over silica gel (230-400 M) using EtOAc-Hexane (2:98) to provide the compound as yellow oil (0.050 g, 7.20%).

MS: 455 (M+H)$^+$.

Step 3. 1-Ethyl-3-[7-(6-morpholin-4-yl-pyridin-2-yl)-5-pyridin-3-yl-benzothiazol-2-yl]-urea Example 166

To a solution of 1-(7-iodo-5-pyridin-3-yl-benzothiazol-2-yl)-3-ethyl-urea (0.15 g, 0.35 mmol) in DMF (5 mL) was added 4-(6-tributylstannanyl-pyridin-2-yl)-morpholine (0.30 g, 0.70 mmol) under nitrogen atmosphere at room temperature. The reaction mixture was then degassed for half an hour followed by the addition of tetrakis(triphenylphosphine)palladium(0) (0.020 g, 0.018 mmol). The reaction mixture was then again degassed for half an hour and heated at 120° C. for 15 h under nitrogen atmosphere. After the completion of the reaction (TLC monitoring), DMF was distilled off; water was added to the reaction mixture and extracted with ethyl acetate. The combined organic layers were dried over anhydrous Na$_2$SO$_4$, and evaporated to dryness under reduced pressure. The crude residue was purified by prep HPLC to get the title compound (0.01 g, 6.0%) as white solid.

$^1$H NMR (DMSO-d$_6$, 400 MHz): δ 1.09 (t, J=7.20 Hz, 3H), 3.21 (m, 2H), 3.70-3.71 (m, 4H), 3.78-3.79 (m, 4H), 6.89-6.91 (m, 1H), 7.07 (br s, 1H), 7.50-7.54 (m, 1H), 7.68-7.77 (m, 2H), 7.98 (s, 1H), 8.15 (s, 1H), 8.26-8.28 (m, 1H), 8.59 (m, 1H), 9.08 (s, 1H) and 10.64 (br s, 1H). MS: 461.24 (M+H)$^+$.

Qualitative HPLC Purity (Xbridge C18, 250×4.6 mm, 260 nm): 90.43% (Rt=14.25 min).

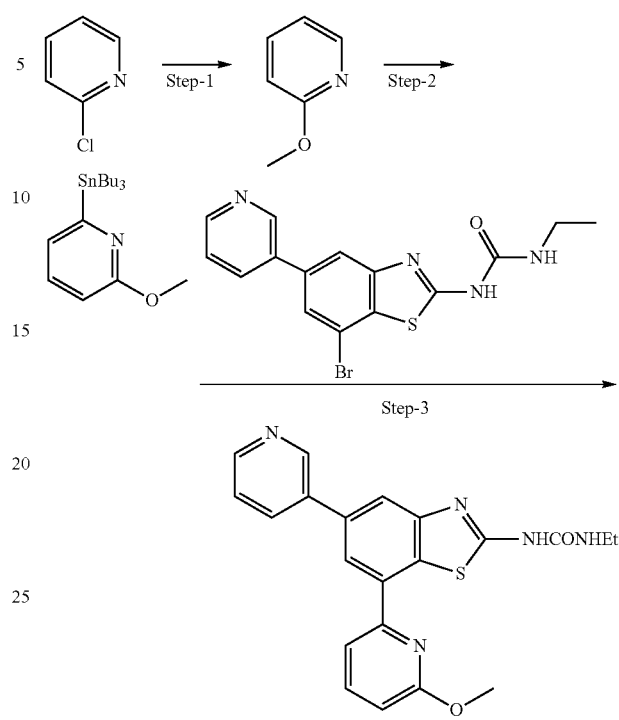

Scheme 9D.

Step 1. 2-Methoxy-pyridine

A mixture of 2-chloro pyridine (5.0 g, 44.0 mmol) and KOMe (3.10 g, 44.0 mmol) in MeOH (50.0 mL) was heated in a steel bomb at 180° C. for 48 h. After the completion of the reaction (TLC monitoring), MeOH was distilled off and the residue was purified over silica gel (60-120 M, 2% EtOAc-Hexane) to get the title compound (0.60 g, 12%).

$^1$H NMR (CDCl$_3$, 400 MHz): δ 3.93 (s, 3H), 6.75 (8.80 Hz, 1H), 6.84-6.87 (m, 1H), 7.53-7.58 (m, 1H) and 8.15–8.17 (m, 1H).

Step 2. 2-Methoxy-6-tributylstannanyl-pyridine

To a solution of 2-dimethylaminoethanol (3.50 mL, 16.36 mmol) in hexane (20.0 mL, HPLC grade) cooled at −5° C. was added drop wise n-BuLi (3.60 M, 9.0 mL, 32.40 mmol) under nitrogen atmosphere. After 30 min at 0° C., 2-methoxy-pyridine (0.60 g, 5.45 mmol) in hexane (20.0 mL) was added drop wise. After stirring the reaction mixture for 1 h at 0-5° C., the reaction medium was cooled to −78° C. followed by drop wise addition of tributyl tin chloride (3.70 mL, 13.62 mmol). The resulting reaction mixture was stirred at −78° C. for 30 min and then allowed to stir at 0-5° C. for 30 min. The reaction mixture was then allowed to come to room temperature. After the completion of reaction (TLC monitoring), the reaction mass was cooled to 0° C. and water was added slowly. The aqueous phase was extracted with diethyl ether (3×50 mL). The combined organic layers were dried over anhydrous Na$_2$SO$_4$, and evaporated to dryness. The crude residue (1.80 g, 72%) was carried forward to the next step without further purification.

Step 3. 1-Ethyl-3-[7-(6-methoxy-pyridin-2-yl)-5-pyridin-3-yl-benzothiazol-2-yl]-urea: [Example 167]

To a solution of 1-(7-bromo-5-pyridin-3-yl-benzothiazol-2-yl)-3-ethyl-urea (0.50 g, 1.32 mmol) in DMF (5.0 mL) was added 2-methoxy-6-tributylstannanyl-pyridine (1.05 g, 2.65 mmol) under nitrogen atmosphere at room temperature. The reaction mixture was then degassed for half an hour followed by the addition of tetrakis(triphenylphosphine)palladium(0) (0.23 g, 0.20 mmol). The reaction mixture was then again degassed for half an hour and heated at 120° C. for 6 h under nitrogen atmosphere. After the completion of the reaction (TLC monitoring), DMF was distilled off; water was added to the reaction mixture and extracted with ethyl acetate. The combined organic layers were dried over anhydrous $Na_2SO_4$, and evaporated to dryness under reduced pressure. The crude residue was purified by prep HPLC to get the title compound as white solid (0.06 g, 11%). M.P. 300.10° C.

$^1$H NMR (DMSO-$d_6$, 400 MHz): δ 1.10 (t, J=7.20 Hz, 3H), 3.21 (q, J=7.20 Hz, 2H), 4.17 (s, 3H), 6.81 (br s, 1H), 6.89 (d, J=8.40 Hz, 1H), 7.52-7.55 (m, 1H), 7.92 (t, J=8.0 Hz, 1H), 8.03 (s, 1H), 8.07 (d, J=8.0 Hz, 1H), 8.26 (s, 1H), 8.30 (d, J=8.0 Hz, 1H), 8.61 (m, 1H), 9.10 (s, 1H) and 10.65 (br s, 1H). MS: 406.18 (M+H)$^+$.

Qualitative HPLC Purity (Xbridge C18, 250×4.6 mm, 261 nm): 94.90% (Rt=14.73 min).

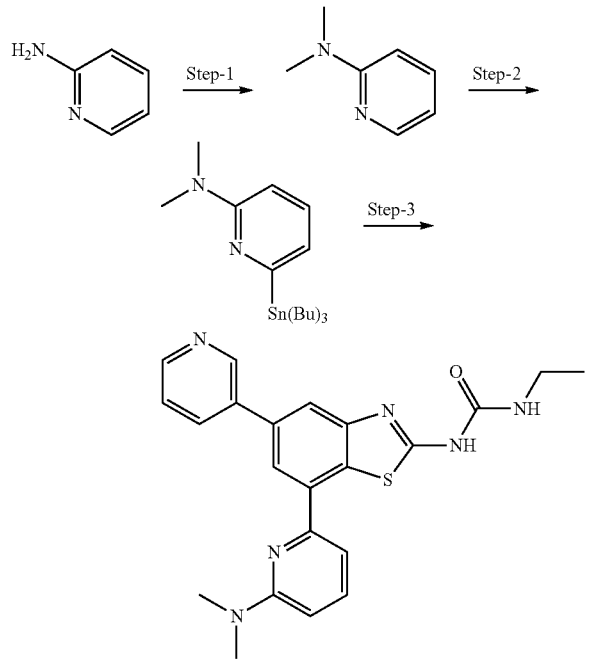

Scheme 9E.

Step-1. Dimethyl-pyridin-2-yl-amine

To an ice-cold solution of 2-aminopyridine (5.0 g, 53.12 mmol) in acetonitrile (150.0 mL) was added sequentially water (33.0 mL) followed by formaldehyde (37% aq. solution, 50.0 mL) and sodium cyanoborohydride (10.0 g, 159.13 mmol). The resulting reaction mixture was stirred at 0° C. for 10 min followed by drop wise addition of acetic acid (12.0 mL). The reaction mixture was then allowed to stir at room temperature for 15 h. After the completion of the reaction (TLC monitoring), the solvent was evaporated and the residue was treated with aqueous NaOH (2N, 50.0 mL) and extracted with hexane (3×50.0 mL). The combined organics was washed with brine, dried ($Na_2SO_4$), filtered and concentrated. The residue was purified over silica gel (100-200 M, 2% EtOAc-Hexane) to get the desired compound (3.50 g, 55%).

$^1$H-NMR (400 MHz, DMSO-$d_6$): δ 2.99 (s, 6H), 6.52-6.55 (m, 1H), 6.61 (d, J=8.80 Hz, 1H), 7.44-7.49 (m, 1H) and 8.07 (m, 1H). MS: 123.10 (M+H)$^+$.

Step-2.
Dimethyl-(6-tributylstannanyl-pyridin-2-yl)-amine

To a solution of 2-dimethylaminoethanol (0.65 mL, 9.60 mmol) in hexane (10.0 mL, HPLC grade) cooled at −5° C. was added drop wise n-BuLi (1.60 M, 11.38 mL, 18.20 mmol) under nitrogen atmosphere. After 30 min at 0° C., dimethyl-pyridin-2-yl-amine (0.40 g, 3.20 mmol) in hexane (5.0 mL) was added drop wise. After stirring the reaction mixture for 1 h at 0-5° C., the reaction medium was cooled to −78° C. followed by drop wise addition of tributyl tin chloride (1.55 mL, 8.0 mmol). The resulting reaction mixture was stirred at −78° C. for 30 min and then allowed to stir at 0-5° C. for 1 h. The reaction mixture was then allowed to stir at room temperature for 16 h. After the completion of reaction (TLC monitoring), the reaction mass was cooled to 0° C. and water was added slowly. The aqueous phase was extracted with diethyl ether (3×20 mL). The combined organic layers were dried over anhydrous $Na_2SO_4$, and evaporated to dryness. The crude residue was carried forward to the next step without further purification. MS: 413.22.

Step-3. 1-[7-(6-Dimethylamino-pyridin-2-yl)-5-pyridin-3-yl-benzothiazol-2-yl]-3-ethyl-urea
[Example 168]

To a solution of 1-(7-bromo-5-pyridin-3-yl-benzothiazol-2-yl)-3-ethyl-urea (0.125 g, 0.33 mmol) in DMF (5 mL) was added dimethyl-(6-tributylstannanyl-pyridin-2-yl)-amine (0.14 g, 0.33 mmol) under nitrogen atmosphere at room temperature. The reaction mixture was then degassed for half an hour followed by the addition of bis(triphenylphosphine)palladium(II) dichloride (0.023 g, 0.033 mmol). The reaction mixture was then again degassed for half an hour and heated at 100° C. for 15 h under nitrogen atmosphere. After the completion of the reaction (TLC monitoring), DMF was distilled off; water was added to the reaction mixture and extracted with ethyl acetate. The combined organic layers were dried over anhydrous $Na_2SO_4$, and evaporated to dryness under reduced pressure. The crude residue was purified by prep HPLC to get the title compound (0.006 g, 5.0%) as off-white solid.

$^1$H-NMR (400 MHz, DMSO-$d_6$): δ 1.10 (t, J=6.80 Hz, 3H), 3.19 (m, 2H), 3.23 (s, 6H), 6.84 (d, J=8.40 Hz, 1H), 6.97 (br s, 1H), 7.51 (m, 1H), 7.58 (d, J=7.20 Hz, 1H), 7.67 (t, J=7.60 Hz, 1H), 7.98 (s, 1H), 8.13 (s, 1H), 8.27 (m, 1H), 8.60 (m, 1H), 9.07 (s, 1H) and 11.03 (br s, 1H). MS: 419.24 (M+H)$^+$.

HPLC: (Xbridge C18, 250×4.6 mm, 259 nm): 92.51% (Rt=14.81 min).

The following was also prepared by the same method starting from step-2.

| ID | NAME | $^1$H-NMR/MS Data |
|---|---|---|
| Example 169 | 1-[7-(4-Dimethylamino-pyridin-2-yl)-5-pyridin-3-yl-benzothiazol-2-yl]-3-ethyl-urea | $^1$H-NMR (400 MHz, DMSO-$d_6$): δ 1.10 (t, J = 6.80 Hz, 3H), 3.18 (s, 6H), 3.21 (m, 2H), 6.86 (m, 1H), 7.07 (s, 1H), 7.46 (m, 1H), 7.55 (m, |

-continued

| ID | NAME | ¹H-NMR/MS Data |
|---|---|---|
| | | 1H), 8.02 (m, 1H), 8.26 (m, 1H), 8.33 (m, 1H), 8.62 (m, 1H), 8.80 (m, 1H), 9.10 (s, 1H) and 10.60 (br s, 1H). MS: 419.24 (M + H)⁺. HPLC: (Xbridge C18, 250 × 4.6 mm, 265 nm): 59.82% (Rt = 12.20 min). |

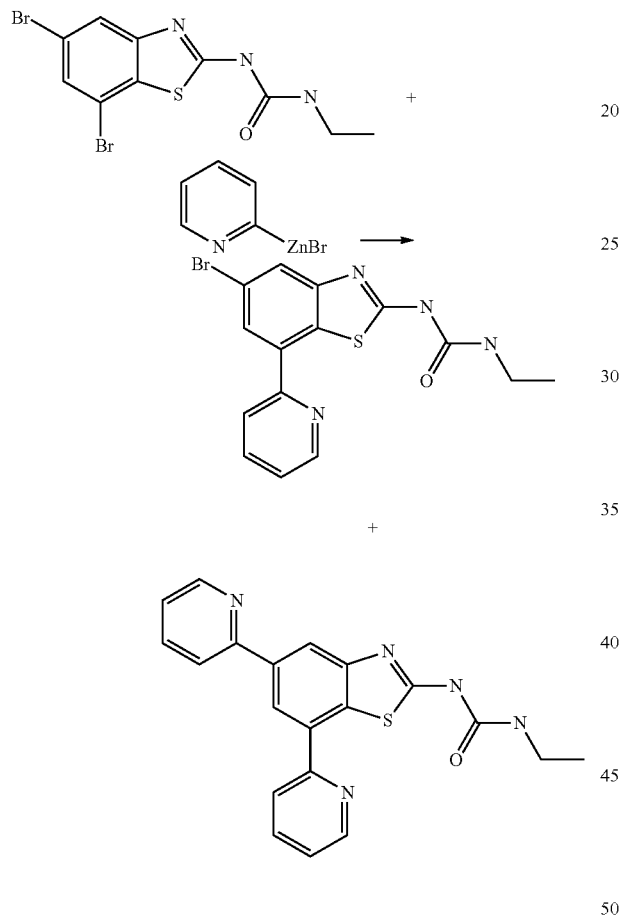

Scheme 10

1-(5-Bromo-7-pyridin-2-yl-benzothiazol-2-yl)-3-ethyl-urea

A stirred mixture of the 1-(5,7-dibromo-benzothiazol-2-yl)-3-ethyl urea (2.62 g, 0.00687 mol) and Dichlorobis(triphenylphosphine)-palladium (0.48 g 0.000687 mol), under nitrogen, was treated in one portion, via a syringe, with 2-pyridyl zinc bromide solution (0.5M solution in THF, 7.66 g, 0.0344 mol). The reaction mixture was heated, with stirring, at 55° C. for 18 hours, allowed to cool and poured into 500 ml of water containing ~5 ml of conc hydrochloric acid. The suspension was stirred and the solid filtered off, washed with water, followed by 20 ml of 1:1 DCM/Methanol mixture to give the crude 1-(5-Bromo-7-pyridin-2-yl-benzothiazol-2-yl)-3-ethyl-urea (1.43 g). This was purified by "flash" silica chromatography using 0 to 100% hexane/ethyl acetate followed by 0 to 100% methanol in ethyl acetate to elute the required product as a beige solid (1.1 g).
¹H NMR (400 MHz, δ, D₆DMSO): 1.13 (3H, t), 3.23 (2H, m), 6.83 (1H, t), 7.50 (1H, m), 7.91 (1H, s), 8.02 (1H, t), 8.20 (1H, s), 8.36 (1H, d), 8.84 (1H, dd), 10.76 (1H, br s).
LC-MS m/z 377 [M+H]⁺ Rt=3.82 min.

1-(4,6-Dipyridin-2-yl benzothiazol-2-yl) 3-ethylurea.
[Example 170]

Also isolated during the purification was a sample of 1-(4,6-Dipyridin-2-yl benzothiazol-2-yl) 3-ethylurea as an off-white solid.
¹H NMR (400 MHz, δ, D₆DMSO): 1.16 (3H, t), 3.26 (2H, m), 6.88 (1H, t), 7.44 (1H, m), 7.50 (1H, m), 7.97 (1H, m), 8.06 (1H, m), 8.29 (1H, d), 8.46 (2H, d), 8.71 (1H, s), 8.77 (1H, d), 8.65 (1 h, d), 10.70 (1 h, s).
LC-MS m/z 376 [M+H]⁺ Rt=2.90 min.

No Example 171

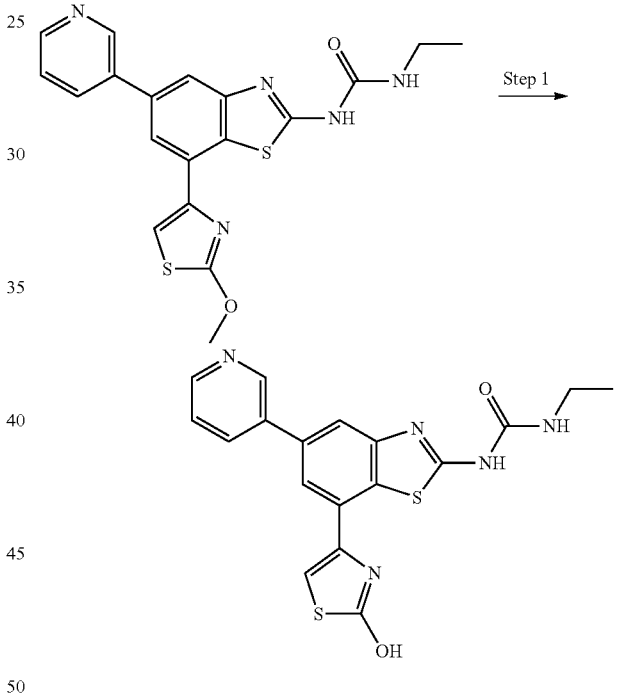

Scheme 13 A.

1-Ethyl-3-[7-(2-hydroxy-thiazol-4-yl)-5-pyridin-3-yl-benzothiazol-2-yl]-urea: [Example 172]

To a solution of 1-ethyl-3-[7-(2-methoxy-thiazol-4-yl)-5-pyridin-3-yl-benzothiazol-2-yl]-urea (0.05 g, 0.12 mmol) in dry DCM (5 mL) was added BBr₃ (0.20 mL) under nitrogen atmosphere at 0° C. The reaction mixture was then heated at 50° C. for 24 h under nitrogen atmosphere. After the completion of the reaction (TLC monitoring), the reaction mixture was cooled to 0° C. and then quenched with ice-cold water followed by extraction with DCM. The combined organic layers were dried over anhydrous Na₂SO₄, and evaporated to dryness under reduced pressure. The crude residue was purified over silica gel (230-400 M) using DCM-MeOH (96:4) to provide the title compound as light greenish solid (3.5 mg, 7%).

¹H-NMR (400 MHz, DMSO-d₆): δ 1.10 (t, J=7.20 Hz, 3H), 3.21 (q, J=7.20 Hz, 2H), 6.77 (br s, 1H), 6.87 (s, 1H), 7.51-7.56 (m, 1H), 7.79 (s, 1H), 8.01 (s, 1H), 8.26 (d, J=8.0 Hz, 1H), 8.62 (br s, 1H), 9.09 (s, 1H), 10.95 (s, 1H) and 11.99 (s, 1H). MS: 398.07 (M+H)⁺.

Qualitative HPLC Purity (Xbridge C18, 250×4.6 mm, 263 nm): 88.40% (Rt=13.21 min).

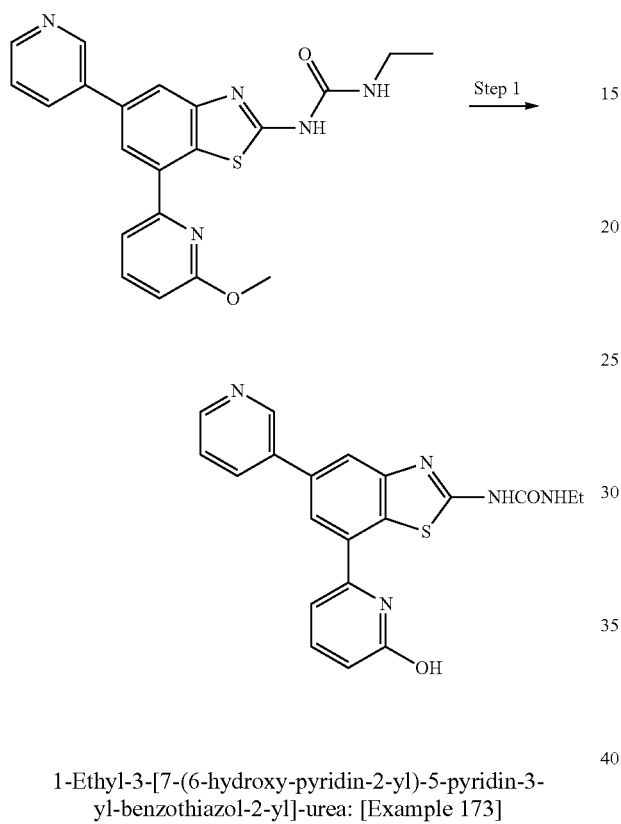

Scheme 13 B.

1-Ethyl-3-[7-(6-hydroxy-pyridin-2-yl)-5-pyridin-3-yl-benzothiazol-2-yl]-urea: [Example 173]

To a solution of 1-ethyl-3-[7-(6-methoxy-pyridin-2-yl)-5-pyridin-3-yl-benzothiazol-2-yl]-urea (0.04 g, 0.098 mmol) in dry DCM was added BBr₃ (0.50 ml) under nitrogen atmosphere at 0° C. The reaction mixture was then heated at 50° C. for 6 h under nitrogen atmosphere. Since the starting material was not consumed (TLC monitoring), toluene (5 mL) was added into the reaction mixture and heated at 120° C. for 16 h. After the completion of the reaction (TLC monitoring), the reaction mixture was cooled to 0° C. and quenched with ice-cold water. Toluene was distilled off, added water and extracted with DCM. The combined organic layers were dried over anhydrous Na₂SO₄, and evaporated to dryness under reduced pressure. The crude residue was purified over silica gel (100-200 M) using DCM-MeOH (96:4) to provide the title compound as off white solid (2.5 mg, 6%).

¹H NMR (DMSO-d₆, 400 MHz): δ 1.10 (t, J=7.20 Hz, 3H), 3.19 (q, J=7.20 Hz, 2H), 6.60 (br s, 1H), 7.0-7.06 (m, 1H), 7.52-7.54 (m, 1H), 7.62-7.72 (m, 2H), 8.0 (m, 2H), 8.28 (d, J=7.60 Hz, 1H), 8.60 (m, 1H), 9.08 (s, 1H) and 10.91-11.02 (br s, 2H). MS: 392.23 (M+H)⁺.

Qualitative HPLC Purity (Xbridge C18, 250×4.6 mm, 261 nm): 95.09% (Rt=11.74 min).

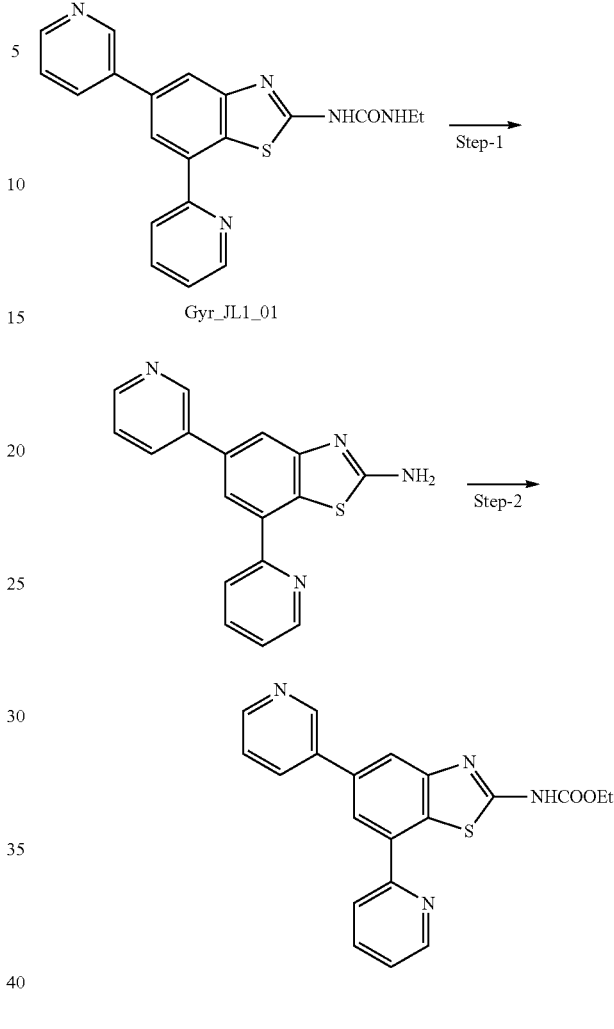

Scheme 14.

Gyr_JL1_01

Step 1. 5-Pyridin-3-yl-7-pyridin-2-yl-benzothiazol-2-ylamine

1-Ethyl-3-(5-pyridin-3-yl-7-pyridin-2-yl-benzothiazol-2-yl)-urea (0.19 g, 0.53 mmol) in DMF (10 mL), was heated at 120° C. for 10 h in pressure vessel. After the completion of the reaction (TLC monitoring), DMF was distilled off, added water and extracted with ethyl acetate. The crude solid (0.14 g, 90%) was used as such for the next step.

Step 2. (5-Pyridin-3-yl-7-pyridin-2-yl-benzothiazol-2-yl)-carbamic acid ethyl ester: [Example 174]

To a solution of 5-pyridin-3-yl-7-pyridin-2-yl-benzothiazol-2-ylamine (0.10 g, 0.33 mmol) in toluene (5 mL) was added triethylamine (0.10 ml, 0.07 mmol) at room temperature. The reaction mixture was heated to 40° C. followed by the addition of ethyl chloroformate (0.17 g, 0.16 mmol). The resulting reaction mixture was stirred under nitrogen atmosphere at 70° C. for 16 h. After the completion of reaction (TLC monitoring) toluene was evaporated under reduced pressure. The crude solid residue was washed with water and was purified by chromatography over silica gel (230-400 M) using ethyl acetate:hexane (60:40) to provide the title compound as white solid (0.046 g, 38%). M.P. 235° C.

¹H NMR (DMSO-d₆, 400 MHz): δ 1.31 (t, J=7.20 Hz, 3H), 4.25-4.30 (m, 2H), 7.45-7.48 (m, 1H), 7.53-7.56 (m, 1H), 8.02 (t, J=7.60 Hz, 1H), 8.11 (s, 1H), 8.33 (d, J=8.0 Hz, 1H), 8.39 (s, 1H, J=8.0 Hz), 8.56 (d, J=8.0 Hz, 1H), 8.63 (d, J=4.80 Hz, 1H), 8.84 (m, 1H), 9.13 (s, 1H) and 11.97 (br s, 1H). MS: 377.16 (M+H⁺). Qualitative HPLC Purity (Xbridge C18, 250×4.6 mm, 260 nm): 96.88% (Rt=14.77 min).

complex with dichloromethane (0.054 g, 0.066 mmol) was added to the reaction mixture, purged again with nitrogen for another 15 min followed by addition of 5-methyl-2-pyridyl zinc bromide (3.32 mL, 1.66 mmol). The resulting reaction mixture was stirred at 100° C. for 15 h followed by removal of DMF in vacuo. Water was added and extracted with EtOAc (3×20 mL). The combined organics was washed with brine, dried (Na₂SO₄) and concentrated. The residue was purified through prep-HPLC to get the desired product (0.011 g, 4%) as an off-white solid.

¹H-NMR (400 MHz, DMSO-d₆): δ 1.13 (t, J=6.80 Hz, 3H), 2.40 (s, 3H), 3.21 (m, 2H), 6.93 (br s, 1H), 7.53 (m, 1H), 7.83 (m, 1H), 8.01 (s, 1H), 8.27-8.31 (m, 2H), 8.41 (d, J=8.40 Hz, 1H), 8.61-8.65 (m, 2H), 9.11 (br s, 1H) and 10.71 (br s, 1H). MS: 390.19 (M+H)⁺. M.P. 231.0° C.

Qualitative HPLC Purity (Xbridge C18, 250×4.6 mm, 265 nm): 98.58 (Rt=14.41 min).

The following were prepared similarly:

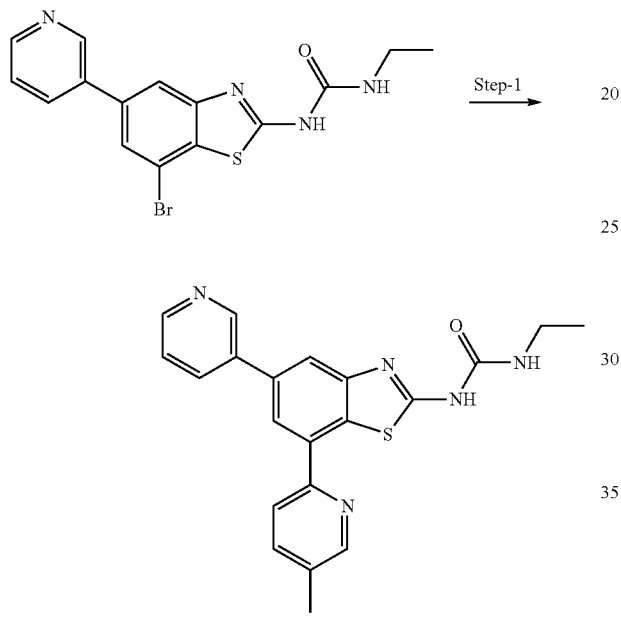

Scheme 16.

Step-1. 1-Ethyl-3-[7-(5-methyl-pyridin-2-yl)-5-pyridin-3-yl-benzothiazol-2-yl]-urea [Example 175]

To a solution of 1-(7-bromo-5-pyridin-3-yl-benzothiazol-2-yl)-3-ethyl-urea (0.25 g, 0.66 mmol) in anhydrous DMF (5.0 mL) was added K₂CO₃ (0.28 g, 1.99 mmol) and the resulting solution was purged with nitrogen for 15 min. [1,1'-Bis(diphenylphosphino)-ferrocene]dichloropalladium(II),

| Prolysis ID. | NAME | NMR/MS/HPLC Data |
|---|---|---|
| Example 176 | 1-Ethyl-3-[7-(4-methyl-pyridin-2-yl)-5-pyridin-3-yl-benzothiazol-2-yl]-urea | ¹H-NMR (400 MHz, DMSO-d₆): δ 1.13 (t, J = 7.20 Hz, 3H), 2.46 (s, 3H), 3.21 (m, 2H), 6.89 (br s, 1H), 7.29 (d, J = 5.20 Hz, 1H), 7.53 (m, 1H), 8.03 (s, 1H), 8.30-8.32 (m, 2H), 8.38 (s, 1H), 8.61 (m, 1H), 8.66 (d, J = 4.80 Hz, 1H), 9.13 (s, 1H) and 10.64 (br s, 1H). MS: 390.21 (M + H)⁺. HPLC: (DHSC-18 (250 × 4.6 mm, 262 nm): 90.42% (Rt = 19.01 min). |
| Example 177 | 1-Ethyl-3-[7-(6-methyl-pyridin-2-yl)-5-pyridin-3-yl-benzothiazol-2-yl]-urea | ¹H-NMR (400 MHz, DMSO-d₆): δ 1.13 (t, J = 7.20 Hz, 3H), 2.66 (s, 3H), 3.30 (m, 2H), 6.88 (br s, 1H), 7.32 (d, J = 7.60 Hz, 1H), 7.54 (m, 2H), 7.88 (t, J = 7.60 Hz, 1H), 8.02 (s, 1H), 8.29-8.31 (m, 2), 8.61 (m, 1H), 9.11 (s, 1H), 10.58 (br s, 1H). MS: 390.29 (M + H)⁺. HPLC: (Xbridge C18, 250 × 4.6 mm, 262 nm): 85.29% (Rt = 14.31 min). |

No Example 178

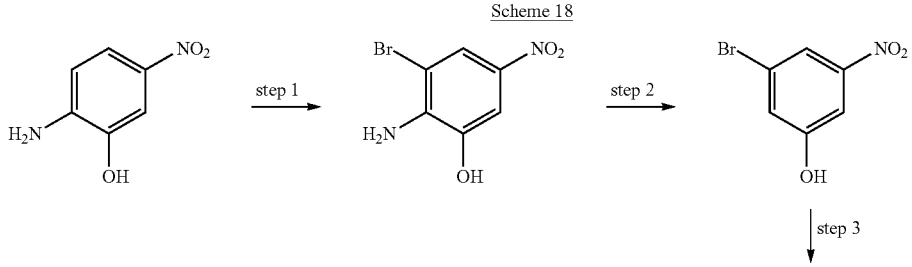

Scheme 18

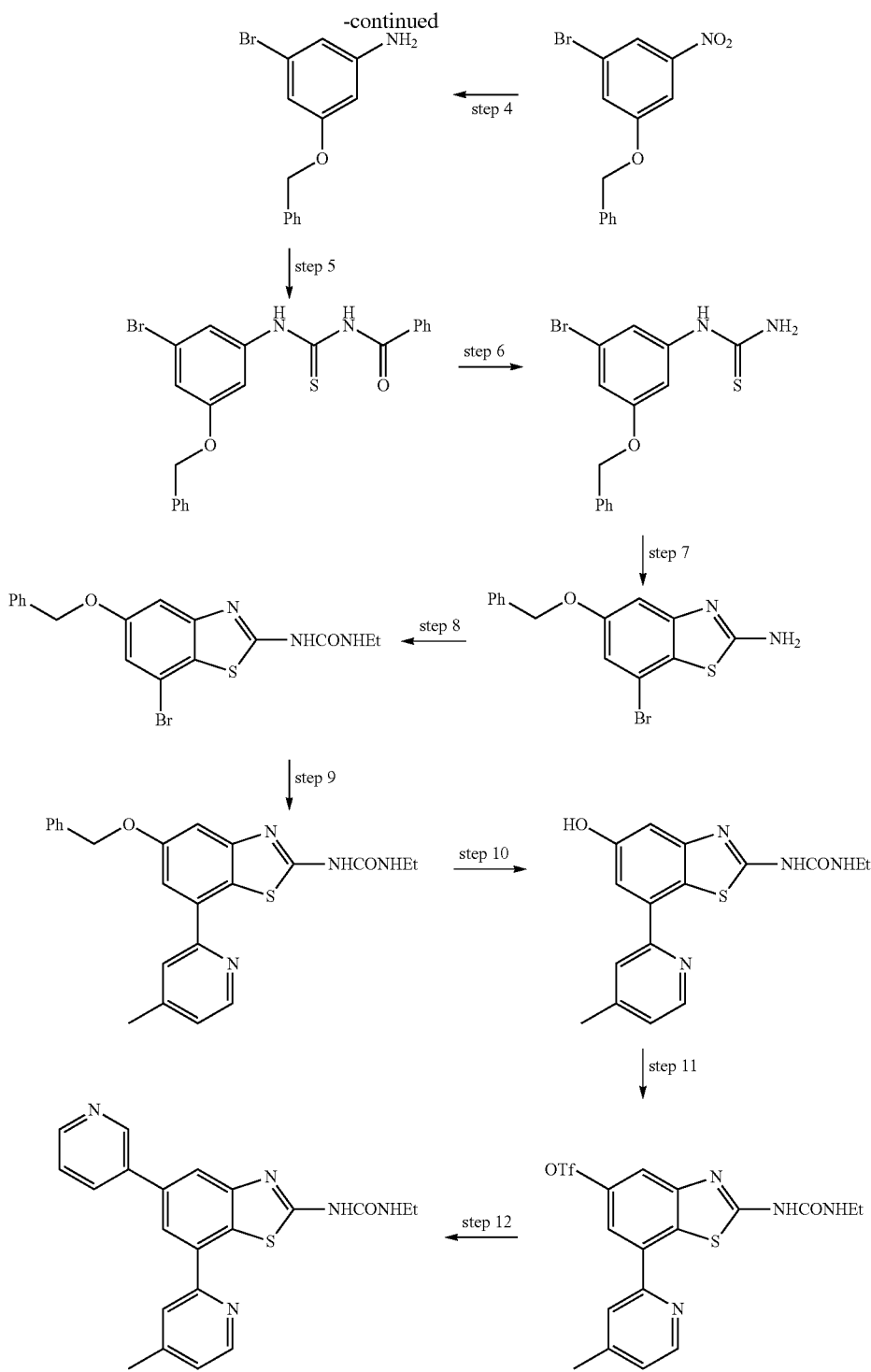

Step 1. 2-Amino-3-bromo-5-nitro-phenol

To an ice-cold solution of 2-amino-5-nitro phenol (40.0 g, 259.52 mmol) in DCM (1.0 L), was added bromine (13.38 mL, 259.52 mmol) drop wise. The resulting reaction mixture was stirred at room temperature for 45 min. After the completion of the reaction (TLC monitoring), water was added and extracted with EtOAc (3×1.0 L). The combined organics was dried over anhydrous $Na_2SO_4$ and concentrated under reduced pressure. The crude (55.0 g, 92%) was carried forward to the next step without further purification.

$^1$H-NMR (400 MHz, DMSO-$d_6$): δ 6.06 (s, 2H), 7.48 (s, 1H), 7.85 (s, 1H) and 10.68 (s, 1H).

Step 2. 3-Bromo-5-nitro-phenol

To an ice-cold solution of 2-amino-3-bromo-5-nitro-phenol (6.50 g, 27.89 mmol) in EtOH (150.0 mL) was added concentrated H$_2$SO$_4$ (9.40 mL, 177.13 mmol) portion wise. The reaction mixture was then heated to 50° C. followed by portion wise addition of NaNO$_2$ (6.19 g, 89.82 mmol). The resulting solution was refluxed at 80° C. for 2 h. The reaction mixture was then diluted with water and extracted with EtOAc (3×150.0 mL). The combined organics was dried over anhydrous Na$_2$SO$_4$ and concentrated under reduced pressure. The crude was purified over silica gel (100-200 M, 10% EtOAc-Hexane) to get the desired product (5.0 g, 82%).

$^1$H-NMR (400 MHz, DMSO-d$_6$): δ 7.37 (s, 1H), 7.53 (s, 1H), 7.77 (s, 1H) and 10.91 (s, 1H).

Step 3. 3-Benzyloxy-5-bromo-nitrobenzene

To an ice-cold solution of 3-bromo-5-nitro-phenol (21.0 g, 96.33 mmol) in acetone (420.0 mL) was added K$_2$CO$_3$ (40.0 g, 289.41 mmol) followed by addition of benzyl bromide (17.20 mL, 144.40 mmol). The resulting reaction mixture was stirred at room temperature for 2 h. The reaction mixture was then diluted with water and extracted with EtOAc (3×250.0 mL). The combined organics was dried over anhydrous Na$_2$SO$_4$ and concentrated under reduced pressure. The crude was purified over silica gel (100-200 M, 5% EtOAc-Hexane) to get the desired product (27.0 g, 91%).

$^1$H-NMR (400 MHz, DMSO-d$_6$): δ 5.13 (s, 2H), 7.35-7.45 (m, 6H), 7.75 (s, 1H) and 7.98 (s, 1H).

Step 4. 3-Benzyloxy-5-bromo-phenylamine

To a solution of 3-benzyloxy-5-bromo-nitrobenzene (27.0 g, 87.60 mmol) in THF (800.0 mL) was added SnCl$_2$.2H$_2$O (99.0 g, 438.30 mmol) and the resulting reaction mixture was heated to reflux at 65° C. for 2 h. The reaction mass was then cooled to 0-5° C. and basified with a saturated solution of NaHCO$_3$ till pH 8 and then extracted with EtOAc (3×1.0 L). The combined organics was dried over anhydrous Na$_2$SO$_4$ and concentrated under reduced pressure. The residue thus obtained (23.60 g, 95%) was carried forward to the next step without further purification.

$^1$H-NMR (400 MHz, CDCl$_3$): δ 3.70 (br s, 2H), 5.03 (s, 2H), 6.25 (s, 1H), 6.46 (s, 1H), 6.65 (s, 1H) and 7.33-7.52 (m, 5H). MS: 278.04 (M+H)$^+$.

Step 5. 1-Benzoyl-3-(3-benzyloxy-5-bromo-phenyl)-thiourea

To a solution of 3-benzyloxy-5-bromo-phenylamine (23.50 g, 84.40 mmol) in acetone (550.0 mL) was added benzoyl isothiocyanate (18.50 mL, 93.13 mmol) and the reaction mixture was stirred at room temperature for 30 min. After the completion of the reaction (TLC monitoring), the solvent was evaporated and the residue thus obtained was washed with hexane to get the desired product (33.0 g, 89%).

$^1$H-NMR (400 MHz, CDCl$_3$): δ 5.05 (s, 2H), 7.05 (m, 1H), 7.38-7.50 (m, 6H), 7.52-7.55 (m, 3H), 7.57-7.67 (m, 1H), 7.90 (d, J=7.60 Hz, 2H), 9.05 (br s, 1H) and 12.67 (br s, 1H).

Step 6. (3-Benzyloxy-5-bromo-phenyl)-thiourea

To an ice-cold solution of 1-benzoyl-3-(3-benzyloxy-5-bromo-phenyl)thiourea (33.0 g, 74.70 mmol) in THF (500.0 mL) was added a solution of NaOH (15.0 g, 375.0 mmol) in H$_2$O (180.0 mL). The resulting reaction mixture was stirred at 65° C. for 15 h. The reaction mass was then cooled to room temperature, added water and extracted with EtOAc (3×1.0 L). The combined organics was washed with water, dried over anhydrous Na$_2$SO$_4$ and concentrated under reduced pressure to get the desired compound (23.50 g, 94%) that was carried forward to the next step without further purification.

$^1$H-NMR (400 MHz, CDCl$_3$): δ 5.10 (s, 2H), 6.97 (s, 1H), 7.14 (s, 1H), 7.29 (s, 1H), 7.32-7.44 (m, 7H) and 9.78 (br s, 1H). MS: 337.04 (M+H)$^+$.

Step 7. 5-Benzyloxy-7-bromo-benzothiazol-2-ylamine

A solution of (3-benzyloxy-5-bromo-phenyl)-thiourea (2.0 g, 5.93 mmol) in CHCl$_3$ (80.0 mL) was cooled to −60° C. followed by drop wise addition of a solution of bromine (0.30 mL, 5.93 mmol) in CHCl$_3$ (20.0 mL). The resulting reaction mixture was stirred at room temperature for 15 minutes followed by refluxing at 70° C. for 1 h. The reaction mass was then cooled and basified with 25% aqueous ammonia solution to pH 8-9 and then extracted with EtOAc (3×150.0 mL). The combined organics was dried over anhydrous Na$_2$SO$_4$ and concentrated under reduced pressure. The crude residue was purified over silica gel (60-120 M, 40% EtOAc-Hexane) to get the desired compound (1.35 g, 68%).

$^1$H-NMR (400 MHz, DMSO-d$_6$): δ 5.12 (s, 2H), 6.93 (d, J=2.0 Hz, 1H), 6.98 d, J=2.0 Hz, 1H), 7.30-7.45 (m, 5H) and 7.70 (br s, 2H). MS: 335.0 (M+H)$^+$.

Step 8. 1-(5-Benzyloxy-7-bromo-benzothiazol-2-yl)-3-ethyl-urea

To a solution of 5-benzyloxy-7-bromo-benzothiazol-2-ylamine (1.35 g, 4.02 mmol) in dioxane (50.0 mL) was added ethyl isocyanate (1.90 mL, 24.22 mmol) and the resulting reaction mixture was heated to 80° C. for 15 h. The solvent was then evaporated and the residue was stirred in water at 85° C. for 5-6 h. The solution was then filtered and the solid thus obtained was washed with hot water and hexane to get the desired product (1.50 g, 92%) as an off-white solid. M.P. 294.2° C.

$^1$H-NMR (400 MHz, DMSO-d$_6$): δ 1.08 (t, J=7.20 Hz, 3H), 3.21 (m, 2H), 5.24 (s, 2H), 6.71 (br s, 1H), 7.15 (s, 1H), 7.21 (s, 1H), 7.26-7.47 (m, 5H) and 10.83 (br s, 1H). MS: 406.0 (M+H)$^+$.

Step 9. 1-[5-Benzyloxy-7-(4-methyl-pyridin-2-yl)-benzothiazol-2-yl]-3-ethyl-urea A mixture of 1-[5-Benzyloxy-7-bromo-benzothiazol-2-yl]-3-ethyl-urea (406 mg, 1.0 mmol), bis(neopentyl)glycolato diboron (452 mg, 2.0 mmol) and potassium acetate (294 mg, 3.0 mmol) in dimethyl sulfoxide (7 ml) was purged with nitrogen for 5 minutes. Bis(diphenylphosphino)ferrocene palladium(II)chloride complex (82 mg, 0.1 mmol) was added, the reaction mixture sealed and heated at 80° C. for 16 h.

The reaction mixture was cooled to ambient temperature. 2-Bromo-4-methylpyridine (258 mg, 1.5 mmol) was added followed by aqueous cesium carbonate solution (3.7M, 0.405 ml, 1.5 mmol). The reaction mixture was purged with nitrogen for 5 minutes, treated with tetrakistriphenylphosphine palladium (0) (115 mg, 0.1 mmol), sealed and heated at 80° C. for 8 h. The reaction mixture was cooled to ambient temperature, diluted with ethylacetate (150 ml), washed with water (3×20 ml) followed by brine (25 ml) and dried (MgSO$_4$). The solvent was removed in vacuo and the residue purified by flash silica chromatography eluting with 1:1 ethyl acetate: petrol ether to give 1-[5-Benzyloxy-7-(4-methyl-pyridin-2-yl)-benzothiazol-2-yl]-3-ethyl-urea as an off white solid (290 mg, 69%).

LC-MS m/z 419 [M+H]$^+$ Rt=4.11 min.

Step 10. 1-Ethyl-3-[5-hydroxy-7-(4-methyl-pyridin-2-yl)-benzothiazol-2-yl]-urea A stirred solution of 1-[5-Benzyloxy-7-(4-methyl-pyridin-2-yl)-benzothiazol-2-yl]-3-ethyl-urea (100 mg, 0.239 mmol) in anhydrous dichloromethane (2 ml) was treated with methanesulfonic acid (0.25 ml) and kept at ambient temperature for 2 h. The dichloromethane was then evaporated off and the residue treated with water (3 ml). The resultant mixture was extracted with ethyl acetate (3×20 ml) and the aqueous portion basified with sodium hydrogen carbonate. The resultant mixture was extracted with ethyl acetate (3×30 ml), dried (MgSO$_4$) and the solvent removed in vacuo to give the crude 1-Ethyl-3-[5-hydroxy-7-(4-methyl-pyridin-2-yl)-benzothiazol-2-yl]-urea (38 mg, 46%) as an off-white solid which was used without further purification.

LC-MS m/z 329 [M+H]$^+$ Rt=2.86 min.

Step 11. Trifluoro-methanesulfonic acid 2-(3-ethyl-ureido)-7-(4-methyl-pyridin-2-yl)-benzothiazol-5-yl ester A stirred suspension of the crude 1-Ethyl-3-[5-hydroxy-7-(4-methyl-pyridin-2-yl)-benzothiazol-2-yl]-urea (38 mg, 0.116 mmol) in anhydrous dichloromethane (3 ml) was treated with anhydrous pyridine (31 mg, 0.394 mmol). The resultant solution was cooled in an ice-bath and treated with trifluoromethanesulfonic anhydride (111 mg, 0.394 mmol). After stirring at ambient temperature for 2 h, the solution was diluted with dichloromethane (75 ml), washed with water (4×25 ml), dried (MgSO$_4$) and the solvent removed to give the crude Trifluoro-methanesulfonic acid 2-(3-ethyl-ureido)-7-(4-methyl-pyridin-2-yl)-benzothiazol-5-yl ester (44 mg, 100%) which was used without further purification.

Step 12. 1-Ethyl-3-[7-(4-methyl-pyridin-2-yl)-5-pyridin-3-yl-benzothiazol-2-yl]-urea [Example 176]

A stirred mixture of the crude Trifluoro-methanesulfonic acid 2-(3-ethyl-ureido)-7-(4-methyl-pyridin-2-yl)-benzothiazol-5-yl ester (44 mg, 0.096 mmol), 3-pyridineboronic acid (13 mg, 0.106 mmol), powdered potassium phosphate tribasic (25 mg, 0.115 mmol), anhydrous 1,4-dioxane (0.7 ml) and anhydrous methanol (1.2 ml) was purged with nitrogen for 15 min. 1,1'-bis(diphenylphosphino)ferrocene palladium (II) chloride complex (12 mg, 0.0144 mmol) was added and the mixture heated at 80° C. for 16 h under an atmosphere of nitrogen. After cooling to ambient temperature, the mixture was filtered through celite and washed through with methanol. The filtrate was evaporated in vacuo to give the crude 1-Ethyl-3-[7-(4-methyl-pyridin-2-yl)-5-pyridin-3-yl-benzothiazol-2-yl]urea.

LC-MS m/z 390 [M+H]$^+$ Rt=2.63 min.

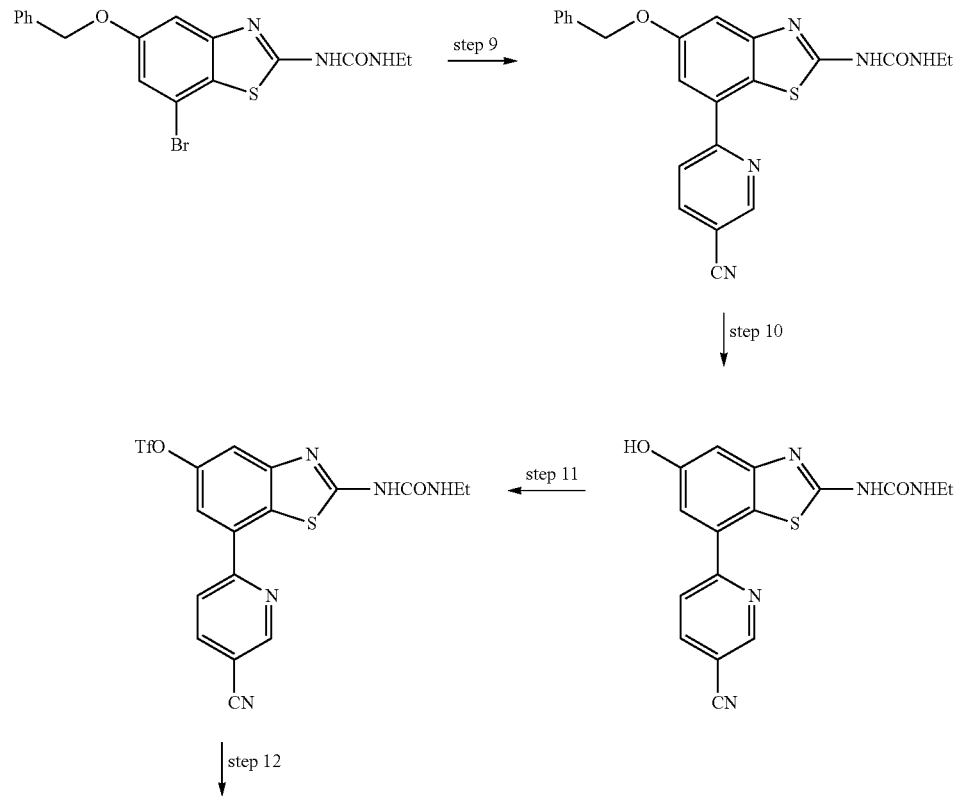

Scheme 18b

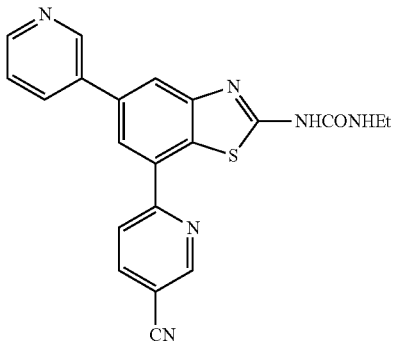

Steps 1 to 8 as Scheme 18

Step 9. 1-[5-Benzyloxy-7-(5-cyano-pyridin-2-yl)-benzothiazol-2-yl]-3-ethyl-urea

A mixture of 1-[5-Benzyloxy-7-bromo-benzothiazol-2-yl]-3-ethyl-urea (406 mg, 1.0 mmol), bis(neopentyl)glycolato diboron (452 mg, 2.0 mmol) and potassium acetate (294 mg, 3.0 mmol) in dimethyl sulfoxide (7 ml) was purged with nitrogen for 5 minutes. Bis(diphenylphosphino)ferrocene palladium(II)chloride complex (82 mg, 0.1 mmol) was added, the reaction mixture sealed and heated at 80° C. for 16 h. The reaction mixture was cooled to ambient temperature. 2-chloro-4-cyanopyridine (208 mg, 1.5 mmol) was added followed by aqueous cesium carbonate solution (3.7M, 0.405 ml, 1.5 mmol). The reaction mixture was purged with nitrogen for 5 minutes, treated with tetrakistriphenylphosphine palladium (0) (115 mg, 0.1 mmol), sealed and heated at 80° C. for 8 h. The reaction mixture was cooled to ambient temperature, diluted with ethylacetate (150 ml), washed with water (3×20 ml) followed by brine (25 ml) and dried (MgSO$_4$). The solvent was removed in vacuo and the residue purified by flash silica chromatography eluting with 1:1 ethyl acetate:petrol ether to give 1-[5-Benzyloxy-7-(5-cyano-pyridin-2-yl)-benzothiazol-2-yl]-3-ethyl-urea as a pale yellow solid (140 mg, 32%).

LC-MS m/z 430 [M+H]$^+$ Rt=3.92 min.

Step 10. 1-[7-(5-Cyano-pyridin-2-yl)-5-hydroxy-benzothiazol-2-yl]-3-ethyl-urea

A stirred solution of 1-[5-Benzyloxy-7-(5-cyano-pyridin-2-yl)-benzothiazol-2-yl]-3-ethyl-urea (110 mg, 0.26 mmol) in anhydrous dichloromethane (3 ml) was treated with methanesulfonic acid (1 ml) and kept at ambient temperature for 2 h. The organic layer was diluted with ethyl acetate then washed with water (3×30 ml), dried (MgSO$_4$) and the solvent removed in vacuo to give the crude 1-[7-(5-Cyano-pyridin-2-yl)-5-hydroxy-benzothiazol-2-yl]-3-ethyl-urea (80 mg, 90%) as an off-white solid which was used without further purification.

LC-MS m/z 340 [M+H]$^+$ Rt=2.96 min.

Step 11. Trifluoro-methanesulfonic acid 7-(5-cyano-pyridin-2-yl)-2-(3-ethyl-ureido)-benzothiazol-5-yl ester A stirred suspension of the crude 1-[7-(5-Cyano-pyridin-2-yl)-5-hydroxy-benzothiazol-2-yl]-3-ethyl-urea (80 mg, 0.23 mmol) in anhydrous dimethylformamide (3 ml) was treated with N-phenylbis(trifluoromethanesulfonimide) (99 mg, 0.276 mmol) and anhydrous triethylamine (32 μl, 0.23 mmol). After stirring at ambient temperature for 2 h, the solution was diluted with ethylacetate (100 ml), washed with water (3×30 ml), dried (MgSO$_4$) and the solvent removed to give the crude trifluoro-methanesulfonic acid 7-(5-cyano-pyridin-2-yl)-2-(3-ethyl-ureido)-benzothiazol-5-yl ester (108 mg, 100%) which was used without further purification.

Step 12. 1-[7-(5-Cyano-pyridin-2-yl)-5-pyridin-3-yl-benzothiazol-2-yl]-3-ethyl-urea [Example 107]

A stirred mixture of the crude trifluoro-methanesulfonic acid 7-(5-cyano-pyridin-2-yl)-2-(3-ethyl-ureido)-benzothiazol-5-yl ester (108 mg, 0.23 mmol), 3-pyridineboronic acid (56 mg, 0.46 mmol), aqueous caesium carbonate (0.155 ml, 0.57 mmol, 3.7M), dimethylformamide (2.4 ml) and water (0.4 ml) was purged with nitrogen for 15 min. treated with tetrakistriphenylphosphine palladium (0) (27 mg, 0.023 mmol), sealed and heated at 80° C. for 8 h. After cooling to ambient temperature, the mixture was filtered through celite and washed through with methanol. The filtrate was evaporated in vacuo to give the crude 1-[7-(5-Cyano-pyridin-2-yl)-5-pyridin-3-yl-benzothiazol-2-yl]-3-ethyl-urea as a brown solid.

LC-MS m/z 401 [M+h]$^+$ Rt=2.61 min.

Analytical Methods Used in the Above Syntheses

The typical analytical and preparative methods used are described below:

Standard acidic LC-MS conditions (3 cm_mode_formic)

Analytical HPLC Setup

| Solvents: | Acetonitrile (Far UV grade) with 0.1% (V/V) formic acid Water (High purity via Elga UHQ unit) with 0.1% formic acid |
|---|---|
| Column: | Phenomenex Luna 5μ C18 (2), 30 × 4.6 mm. |
| Flow Rate: | 2 ml/min |
| Gradient: | A: Water/formic B: MeCN/formic |

| Time | A % | B % |
|---|---|---|
| 0.00 | 80 | 20 |
| 2.50 | 0.00 | 100 |
| 3.50 | 0.00 | 100 |
| 3.60 | 80 | 20 |
| 4.50 | 80 | 20 |

UV Detection via HP or Waters DAD

Start Range (nm) 210 End Range (nm) 400 Range interval (nm) 4.0 Other wavelength traces are extracted from the DAD data.

MS Detection: Either Micromass Platform or ZQ, Both Single Quadrapole LC-MS Instruments.

Flow splitter gives approximately 300 μl/min to mass spec

Scan range for MS Data (m/z)

Start (m/z) 100
End (m/z) 650 or 1000 when required
With +ve/−ve switching
  Ionisation is either electrospray or APCI dependent on compound types (the ZQ has an ESCI option which can give both ESI and APCI data from a single run).
Typical ESI voltages and temperatures are:
Source 120-150 C 3.5 KV capillary 25V cone
Typical APCI voltages and temperatures are:
Source 140-160 C 17uA corona 25V cone Desolvation (Platform) 350 C
HPLC Purification Conditions.
Trilution Standard Conditions—(Samples with analytical Ret Time 0 to 2 min, Acidic)
Preparative HPLC Setup 1

| Solvents: | Acetonitrile with 0.1% Formic Acid (Far UV grade) |  |
|---|---|---|
|  | Water with 0.1% Formic Acid |  |
| Column: | Waters Sunfire C18, 100 × 19 mm. (Plus guard cartridge) |  |
| Flow Rate: | 10 ml/min |  |
| Gradient:- | A: Water/Formic B: MeCN/Formic |  |
| Time | A % | B % |
| 0.00 | 95 | 5 |
| 10 | 80 | 20 |
| 22 | 0 | 100 |
| 25 | 0 | 100 |
| 26 | 95 | 5 |
| 33 | 95 | 5 |

Typical Injections 100-600 ul (10-50 mg/ml)
UV detection via Gilson Dual Wavelength Detector
Collection and 'observation' wavelengths selected from the LC-MS DAD results.
Trilution Standard Conditions—(Samples with analytical Ret Time 2 to 3 min, Acidic)
Preparative HPLC Setup 2

| Solvents: | Acetonitrile with 0.1% Formic Acid (Far UV grade) |  |
|---|---|---|
|  | Water with 0.1% Formic Acid |  |
| Column: | Waters Sunfire C18, 100 × 19 mm. (Plus guard cartridge) |  |
| Flow Rate:- | 10 ml/min |  |
| Gradient: | A: Water/Formic B: MeCN/Formic |  |
| Time | A % | B % |
| 0.00 | 95 | 5 |
| 6 | 90 | 10 |
| 18 | 0 | 100 |
| 23 | 0 | 100 |
| 23.5 | 95 | 5 |
| 30 | 95 | 5 |

Typical Injections 100-600 ul (10-50 mg/ml) in compatible solvent
UV detection via Gilson Dual Wavelength Detector
Collection and 'observation' wavelengths selected from the LC-MS DAD results.
NMR.
$^1$H NMR spectra were recorded on a 400 MHz NMR machine.

TABLE 1

Structures of the examples described herein

| Example number | Structure |
|---|---|
| 1 | [Structure: 6-bromo-benzothiazole with NH-C(O)-NH-Et urea at 2-position and 6-aminopyridin-3-yl substituent] |
| 2 | [Structure: 6-bromo-benzothiazole with pyridin-3-yl substituent and NH-C(O)-NH-Et urea at 2-position] |
| 3 | [Structure: bromo-benzothiazole with pyridin-3-yl substituent and NHCONHEt at 2-position] |

TABLE 1-continued

Structures of the examples described herein

| Example number | Structure |
|---|---|
| 4 | (structure) |
| 5 | (structure) |
| 6 | (structure) |
| 7 | (structure) |
| 8 | (structure) |

TABLE 1-continued
Structures of the examples described herein
| Example number | Structure |
|---|---|
| 9 | 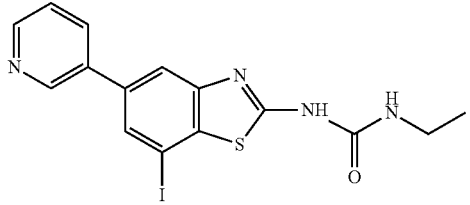 |
| 10 | 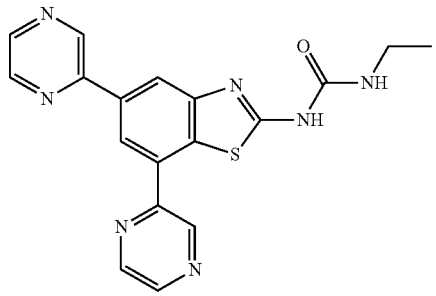 [SMILES: CCNC(=O)Nc1nc2cc(-c3cccnc3)cc(-c3cccnc3)c2s1] |
| 11 | 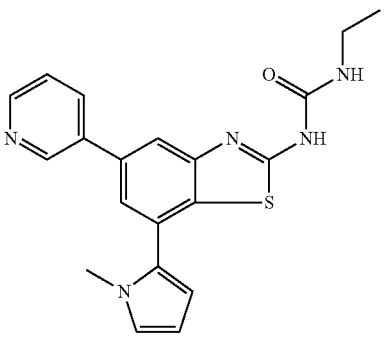 [SMILES: CCNC(=O)Nc1nc2cc(-c3cccnc3)cc(-c3cccn3C)c2s1] |
| 12 | 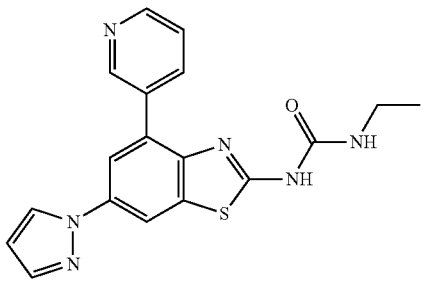 [SMILES: CCNC(=O)Nc1nc2c(-c3cccnc3)cc(-n3cccn3)cc2s1] |
| 13 | 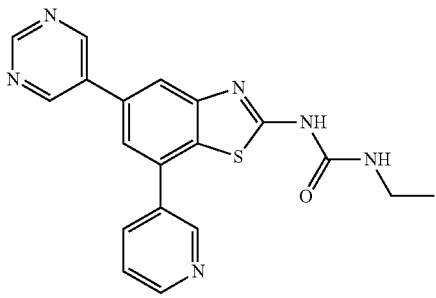 [SMILES: CCNC(=O)Nc1nc2cc(-c3cncnc3)cc(-c3cccnc3)c2s1] |

TABLE 1-continued

Structures of the examples described herein

| Example number | Structure |
|---|---|
| 14 | 5-(2-aminopyrimidin-5-yl)-7-(pyridin-3-yl)-benzothiazol-2-yl ethylurea |
| 15 | 5-(2-methoxypyrimidin-5-yl)-7-(pyridin-3-yl)-benzothiazol-2-yl ethylurea |
| 16 | 5-(6-hydroxypyridin-3-yl)-7-(pyridin-3-yl)-benzothiazol-2-yl ethylurea |
| 17 | 5-(6-aminopyridin-3-yl)-7-(pyridin-3-yl)-benzothiazol-2-yl ethylurea |

TABLE 1-continued
Structures of the examples described herein
| Example number | Structure |
|---|---|
| 18 | 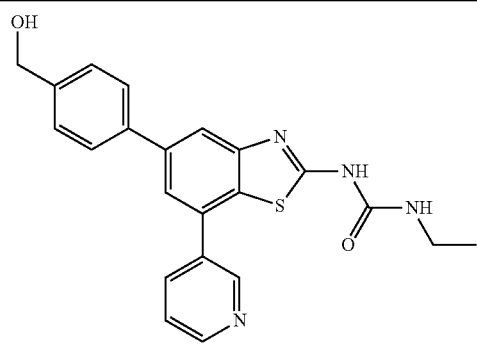 |
| 19 | 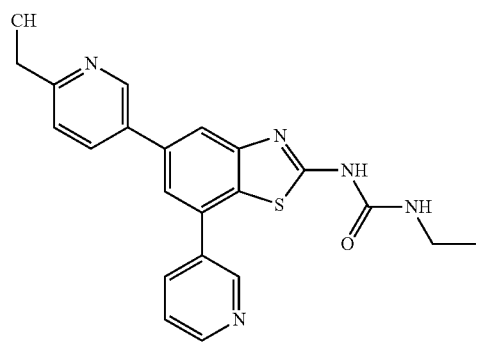 [SMILES: CCNC(=O)Nc1nc2cc(-c3ccc(CC)nc3)cc(-c3cccnc3)c2s1] |
| 20 | 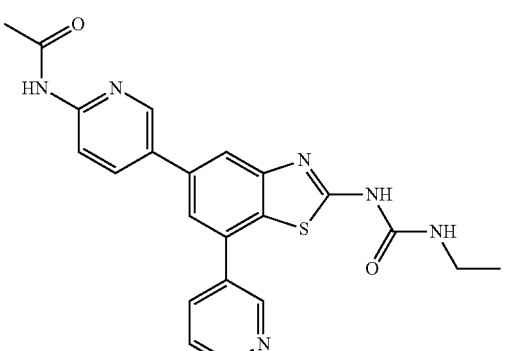 |
| 21 | 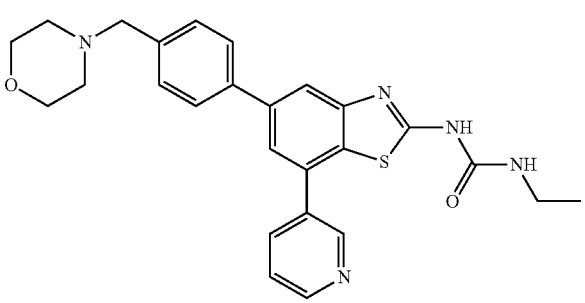 [SMILES: CCNC(=O)Nc1nc2cc(-c3ccc(CN4CCOCC4)cc3)cc(-c3cccnc3)c2s1] |

TABLE 1-continued

Structures of the examples described herein

| Example number | Structure |
| --- | --- |
| 22 | 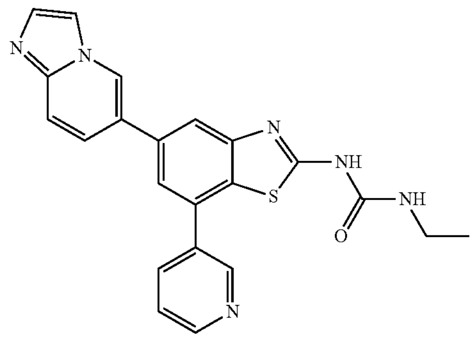 [SMILES: CCNC(=O)Nc1nc2cc(-c3ccc4nccn4c3)cc(-c3cccnc3)c2s1] |
| 23 | 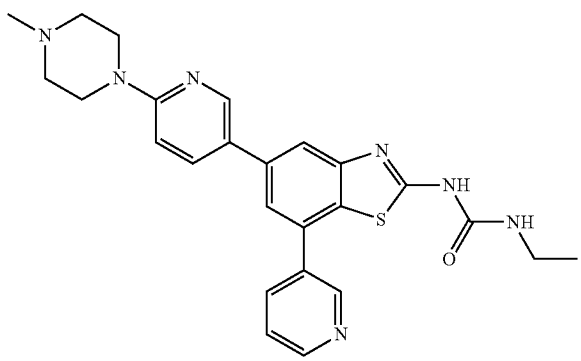 [SMILES: CCNC(=O)Nc1nc2cc(-c3ccc(N4CCN(C)CC4)nc3)cc(-c3cccnc3)c2s1] |
| 24 | 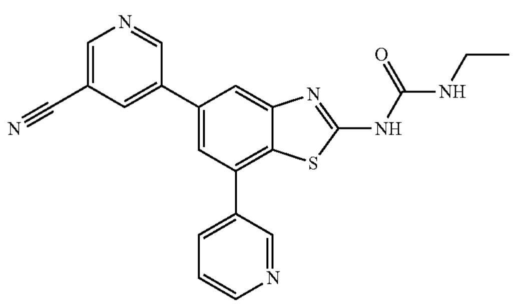 [SMILES: CCNC(=O)Nc1nc2cc(-c3cncc(C#N)c3)cc(-c3cccnc3)c2s1] |
| 25 | 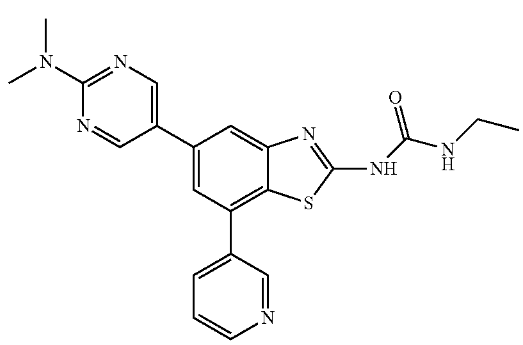 [SMILES: CCNC(=O)Nc1nc2cc(-c3cnc(N(C)C)nc3)cc(-c3cccnc3)c2s1] |

TABLE 1-continued

Structures of the examples described herein

| Example number | Structure |
|---|---|
| 26 | 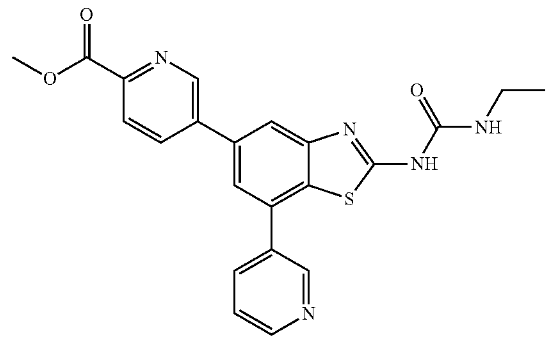 [SMILES: CCNC(=O)Nc1nc2cc(-c3ccc(C(=O)OC)nc3)cc(-c3cccnc3)c2s1] |
| 27 | 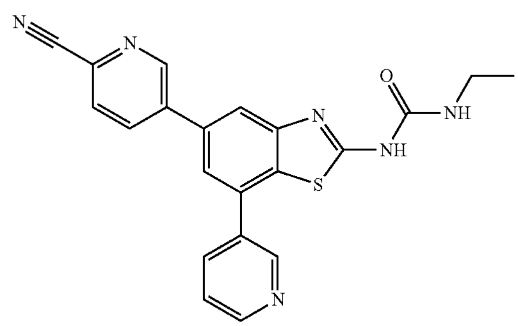 [SMILES: CCNC(=O)Nc1nc2cc(-c3ccc(C#N)nc3)cc(-c3cccnc3)c2s1] |
| 28 | 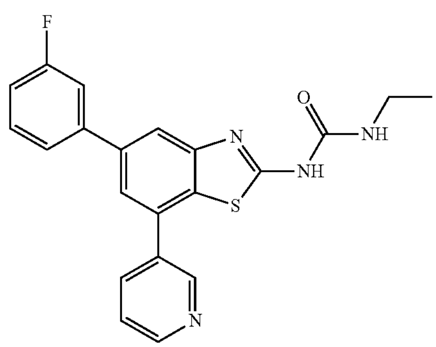 [SMILES: CCNC(=O)Nc1nc2cc(-c3cccc(F)c3)cc(-c3cccnc3)c2s1] |
| 29 | 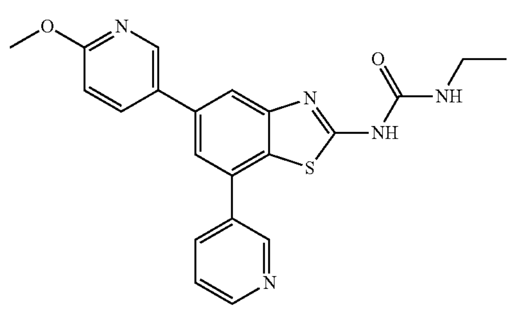 [SMILES: CCNC(=O)Nc1nc2cc(-c3ccc(OC)nc3)cc(-c3cccnc3)c2s1] |

TABLE 1-continued
Structures of the examples described herein
| Example number | Structure |
|---|---|
| 30 | 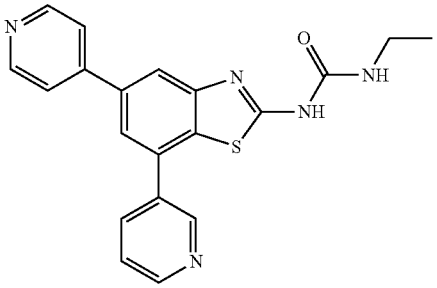 [SMILES: CCNC(=O)Nc1nc2cc(-c3ccncc3)cc(-c3cccnc3)c2s1] |
| 30 | 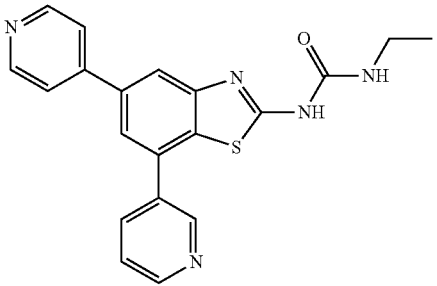 [SMILES: CCNC(=O)Nc1nc2cc(-c3ccncc3)cc(-c3cccnc3)c2s1] |
| 31 | 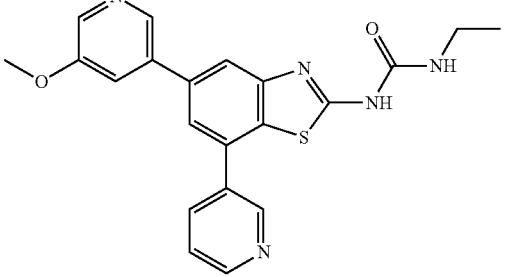 |
| 32 | 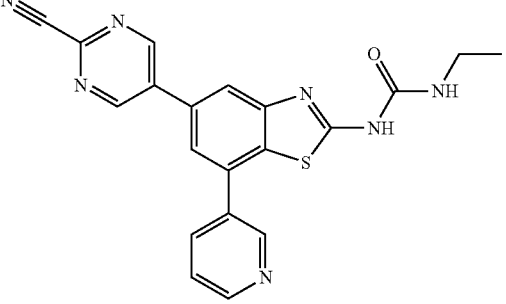 |
| 33 | 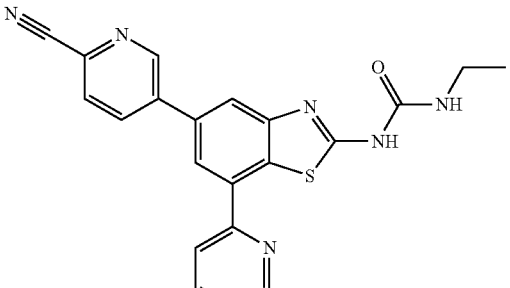 |

TABLE 1-continued

Structures of the examples described herein

| Example number | Structure |
|---|---|
| 34 | 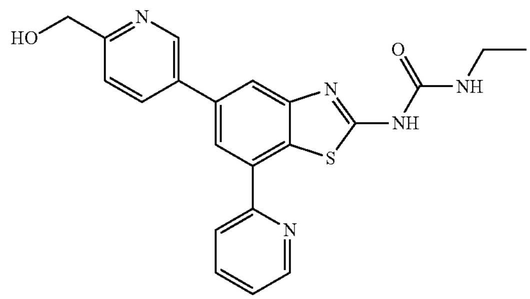 [SMILES: CCNC(=O)Nc1nc2cc(-c3ccc(CO)nc3)cc(-c3ccccn3)c2s1] |
| 35 | 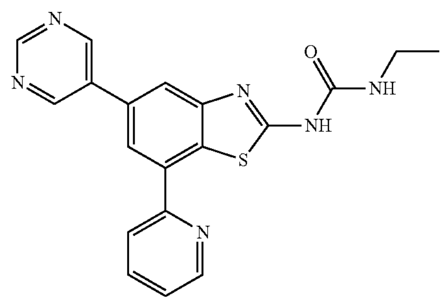 [SMILES: CCNC(=O)Nc1nc2cc(-c3cncnc3)cc(-c3ccccn3)c2s1] |
| 36 | 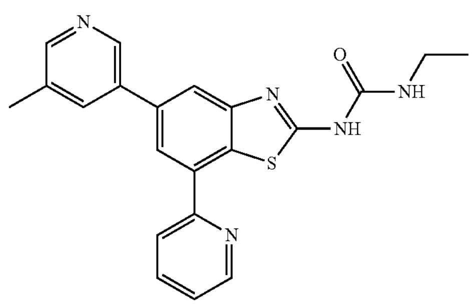 [SMILES: CCNC(=O)Nc1nc2cc(-c3cncc(C)c3)cc(-c3ccccn3)c2s1] |
| 37 | 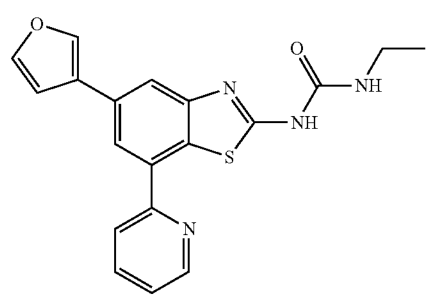 [SMILES: CCNC(=O)Nc1nc2cc(-c3ccoc3)cc(-c3ccccn3)c2s1] |
| 38 | 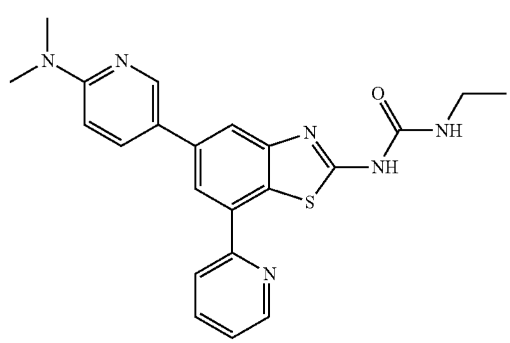 [SMILES: CCNC(=O)Nc1nc2cc(-c3ccc(N(C)C)nc3)cc(-c3ccccn3)c2s1] |

TABLE 1-continued
Structures of the examples described herein
| Example number | Structure |
|---|---|
| 39 | 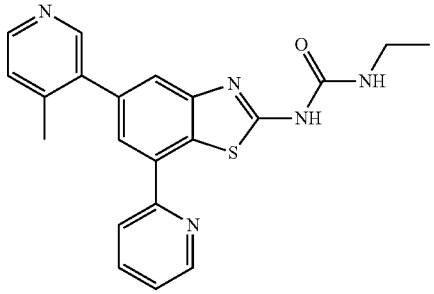 [SMILES: CCNC(=O)Nc1nc2cc(-c3cnccc3C)cc(-c3ccccn3)c2s1] |
| 40 | 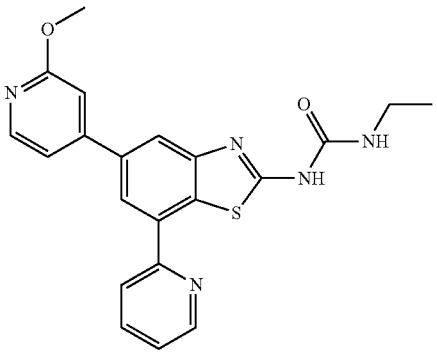 [SMILES: CCNC(=O)Nc1nc2cc(-c3ccnc(OC)c3)cc(-c3ccccn3)c2s1] |
| 41 | 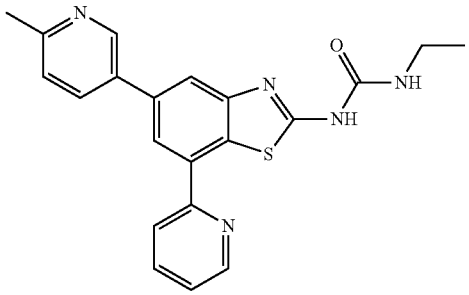 [SMILES: CCNC(=O)Nc1nc2cc(-c3ccc(C)nc3)cc(-c3ccccn3)c2s1] |
| 42 | 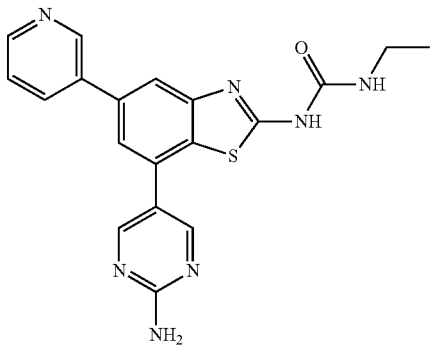 [SMILES: CCNC(=O)Nc1nc2cc(-c3cccnc3)cc(-c3cnc(N)nc3)c2s1] |

TABLE 1-continued

Structures of the examples described herein

| Example number | Structure |
|---|---|
| 43 | (structure) |
| 44 | (structure) |
| 45 | (structure) |
| 46 | (structure) |
| 47 | (structure) |

TABLE 1-continued
Structures of the examples described herein
| Example number | Structure |
|---|---|
| 48 | 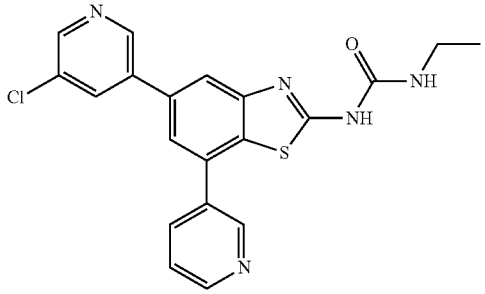 [SMILES: CCNC(=O)Nc1nc2cc(-c3cncc(Cl)c3)cc(-c3cccnc3)c2s1] |
| 49 | 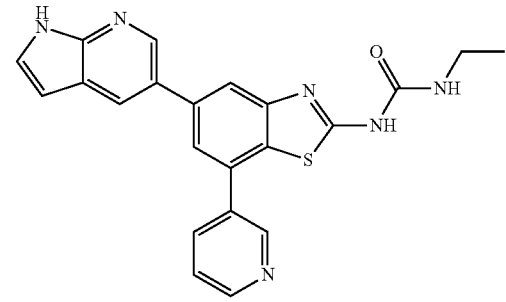 [SMILES: CCNC(=O)Nc1nc2cc(-c3cnc4[nH]ccc4c3)cc(-c3cccnc3)c2s1] |
| 50 | 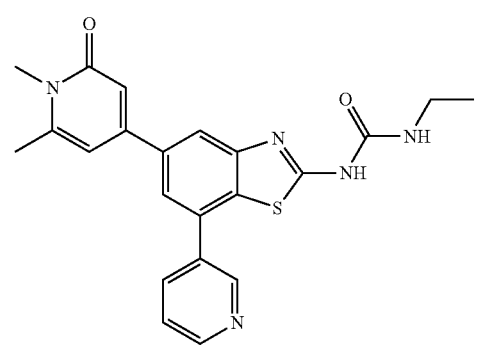 [SMILES: CCNC(=O)Nc1nc2cc(-c3cc(C)n(C)c(=O)c3)cc(-c3cccnc3)c2s1] |
| 51 | 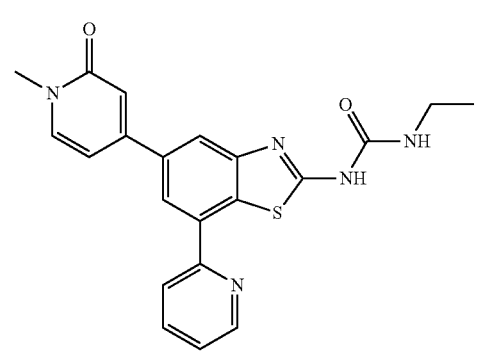 |

TABLE 1-continued

Structures of the examples described herein

| Example number | Structure |
|---|---|
| 52 | (structure) |
| 53 | (structure) |
| 54 | (structure) |
| 55 | (structure) |
| 56 | (structure) |

TABLE 1-continued

Structures of the examples described herein

| Example number | Structure |
|---|---|
| 57 | 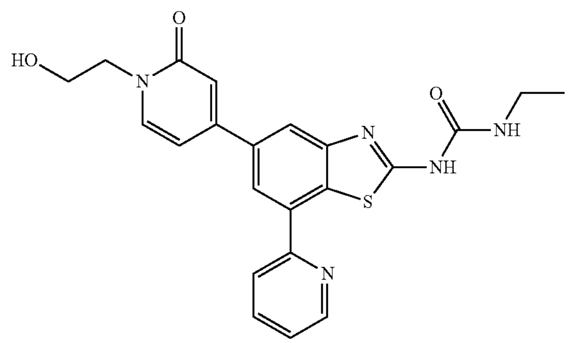 [SMILES: CCNC(=O)Nc1nc2cc(-c3ccn(CCO)c(=O)c3)cc(-c3ccccn3)c2s1] |
| 58 | 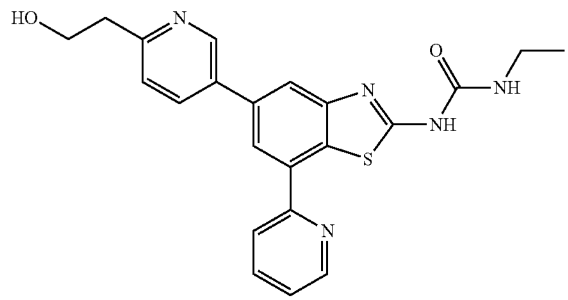 [SMILES: CCNC(=O)Nc1nc2cc(-c3ccc(CCO)nc3)cc(-c3ccccn3)c2s1] |
| 59 | 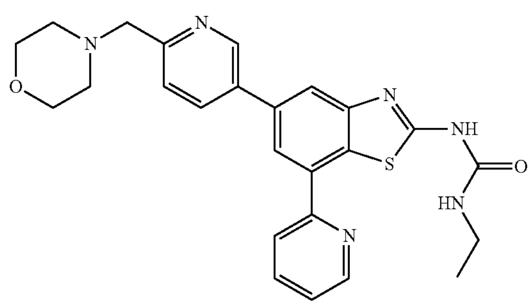 [SMILES: CCNC(=O)Nc1nc2cc(-c3ccc(CN4CCOCC4)nc3)cc(-c3ccccn3)c2s1] |
| 60 | 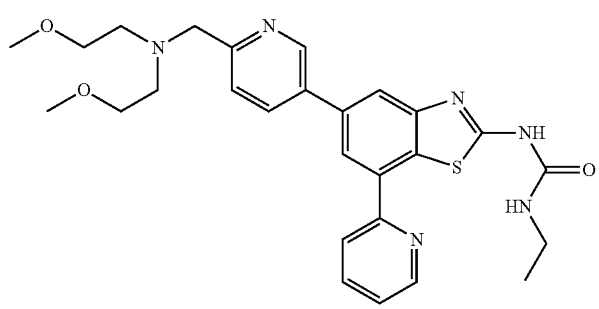 [SMILES: CCNC(=O)Nc1nc2cc(-c3ccc(CN(CCOC)CCOC)nc3)cc(-c3ccccn3)c2s1] |
| 61 | 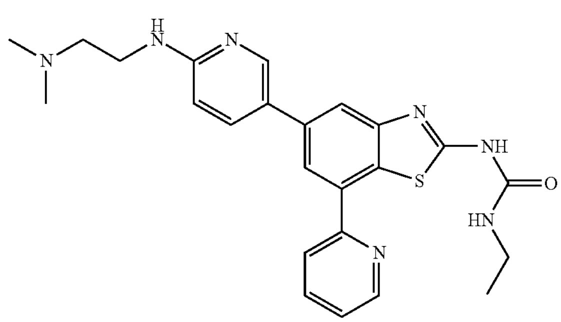 [SMILES: CCNC(=O)Nc1nc2cc(-c3ccc(NCCN(C)C)nc3)cc(-c3ccccn3)c2s1] |

TABLE 1-continued

Structures of the examples described herein

| Example number | Structure |
|---|---|
| 62 | 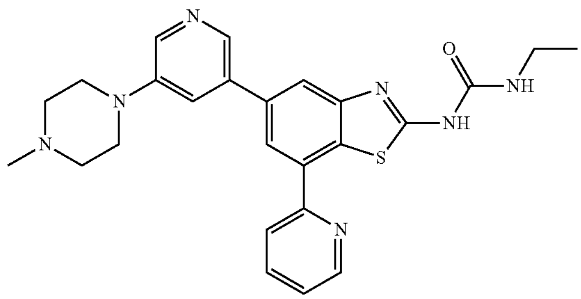 [SMILES: CCNC(=O)Nc1nc2cc(-c3cncc(N4CCN(C)CC4)c3)cc(-c3ccccn3)c2s1] |
| 63 | 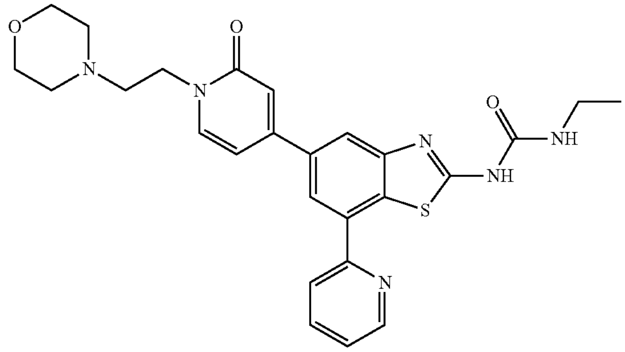 [SMILES: CCNC(=O)Nc1nc2cc(-c3ccn(CCN4CCOCC4)c(=O)c3)cc(-c3ccccn3)c2s1] |
| 64 | 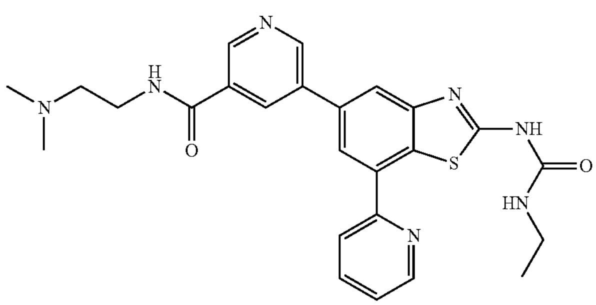 [SMILES: CCNC(=O)Nc1nc2cc(-c3cncc(C(=O)NCCN(C)C)c3)cc(-c3ccccn3)c2s1] |
| 65 | 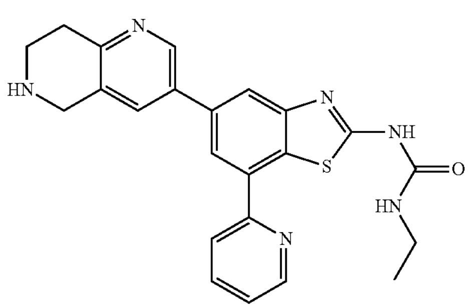 [SMILES: CCNC(=O)Nc1nc2cc(-c3cnc4c(c3)CNCC4)cc(-c3ccccn3)c2s1] |

TABLE 1-continued

Structures of the examples described herein

| Example number | Structure |
|---|---|
| 66 | 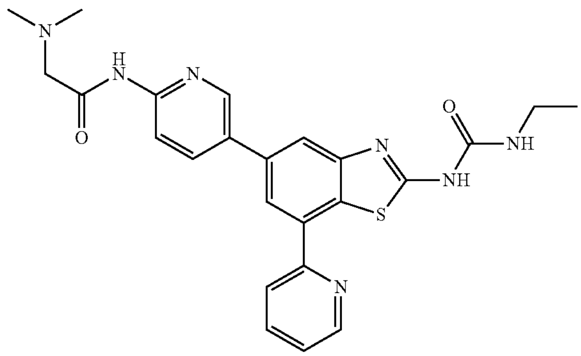 [SMILES: CCNC(=O)Nc1nc2cc(-c3ccc(NC(=O)CN(C)C)nc3)cc(-c3ccccn3)c2s1] |
| 67 | 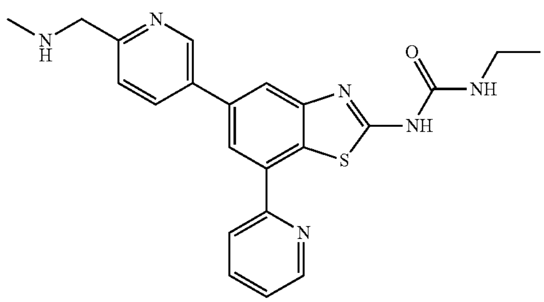 [SMILES: CCNC(=O)Nc1nc2cc(-c3ccc(CNC)nc3)cc(-c3ccccn3)c2s1] |
| 68 | 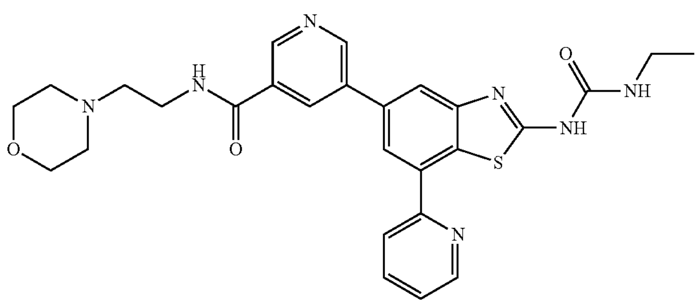 [SMILES: CCNC(=O)Nc1nc2cc(-c3cncc(C(=O)NCCN4CCOCC4)c3)cc(-c3ccccn3)c2s1] |
| 69 | 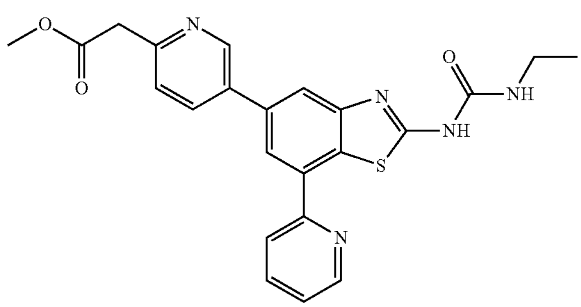 [SMILES: CCNC(=O)Nc1nc2cc(-c3ccc(CC(=O)OC)nc3)cc(-c3ccccn3)c2s1] |
| 70 | 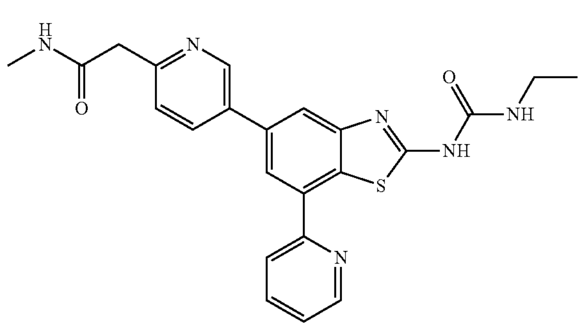 [SMILES: CCNC(=O)Nc1nc2cc(-c3ccc(CC(=O)NC)nc3)cc(-c3ccccn3)c2s1] |

TABLE 1-continued
Structures of the examples described herein
| Example number | Structure |
| --- | --- |
| 71 | 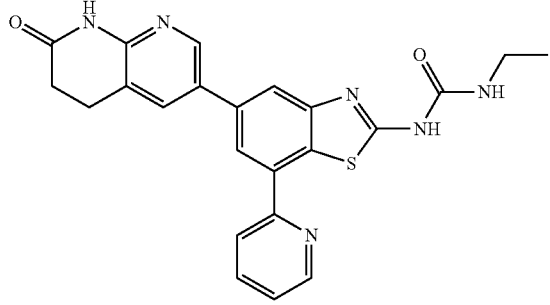 [SMILES: CCNC(=O)Nc1nc2cc(-c3cnc4c(c3)CCC(=O)N4)cc(-c3ccccn3)c2s1] |
| 72 | 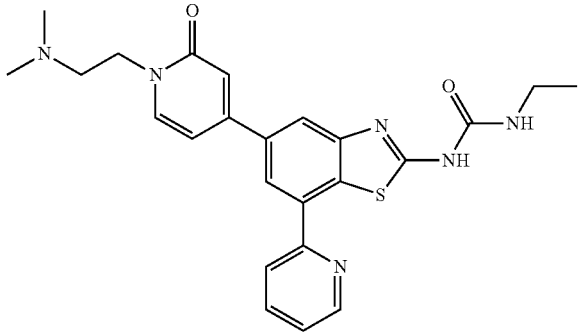 [SMILES: CCNC(=O)Nc1nc2cc(-c3ccn(CCN(C)C)c(=O)c3)cc(-c3ccccn3)c2s1] |
| 73 | 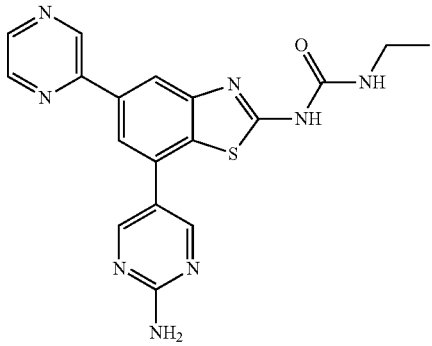 |
| 74 | 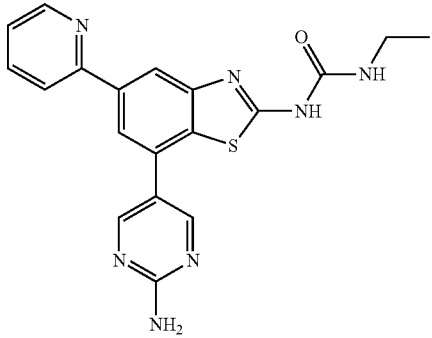 [SMILES: CCNC(=O)Nc1nc2cc(-c3ccccn3)cc(-c3cnc(N)nc3)c2s1] |

TABLE 1-continued

Structures of the examples described herein

| Example number | Structure |
|---|---|
| 75 | 5-(pyridin-3-yl)-7-(2-fluorophenyl)-benzothiazol-2-yl ethylurea |
| 76 | 5-(pyridin-3-yl)-7-(2-fluoropyridin-3-yl)-benzothiazol-2-yl ethylurea |
| 77 | 5-(pyridin-3-yl)-7-(thiophen-3-yl)-benzothiazol-2-yl ethylurea |
| 78 | 5-(pyridin-3-yl)-7-phenyl-benzothiazol-2-yl ethylurea |
| 79 | 5-(pyridin-3-yl)-7-cyclopropyl-benzothiazol-2-yl ethylurea |

TABLE 1-continued

Structures of the examples described herein

| Example number | Structure |
|---|---|
| 80 | 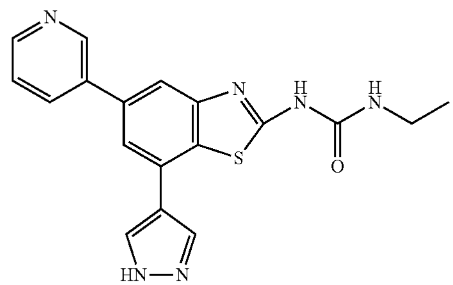 [SMILES: CCNC(=O)Nc1nc2cc(-c3cccnc3)cc(-c3cn[nH]c3)c2s1] |
| 81 | 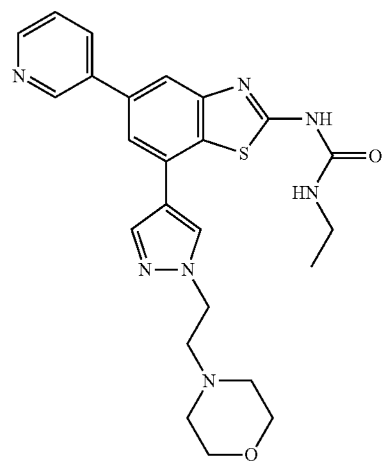 [SMILES: CCNC(=O)Nc1nc2cc(-c3cccnc3)cc(-c3cnn(CCN4CCOCC4)c3)c2s1] |
| 82 | 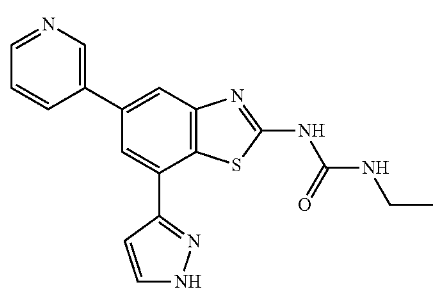 [SMILES: CCNC(=O)Nc1nc2cc(-c3cccnc3)cc(-c3cc[nH]n3)c2s1] |
| 83 | 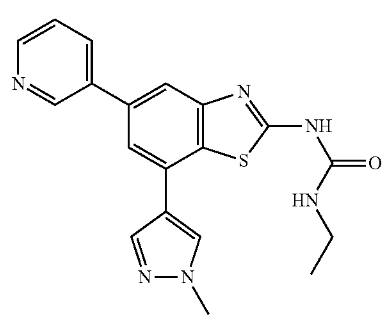 [SMILES: CCNC(=O)Nc1nc2cc(-c3cccnc3)cc(-c3cnn(C)c3)c2s1] |

TABLE 1-continued
Structures of the examples described herein
| Example number | Structure |
|---|---|
| 84 | 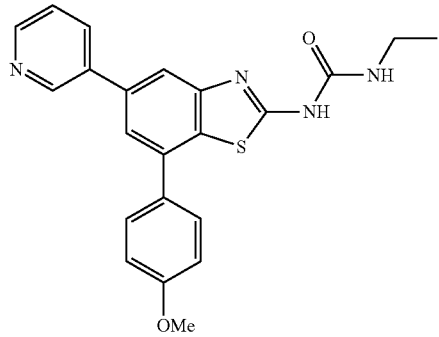 [SMILES: CCNC(=O)Nc1nc2cc(-c3cccnc3)cc(-c3ccc(OC)cc3)c2s1] |
| 85 | 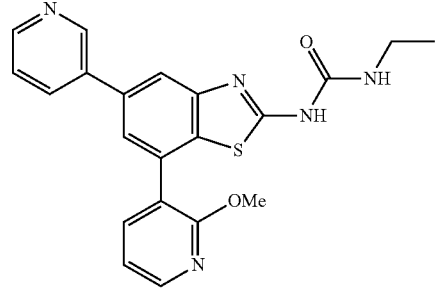 [SMILES: CCNC(=O)Nc1nc2cc(-c3cccnc3)cc(-c3cccnc3OC)c2s1] |
| 86 | 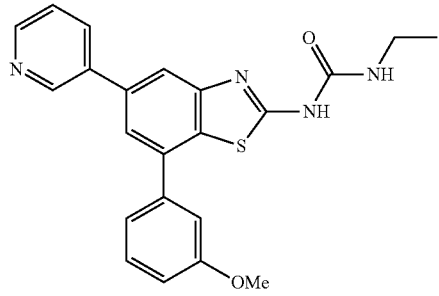 [SMILES: CCNC(=O)Nc1nc2cc(-c3cccnc3)cc(-c3cccc(OC)c3)c2s1] |
| 87 | 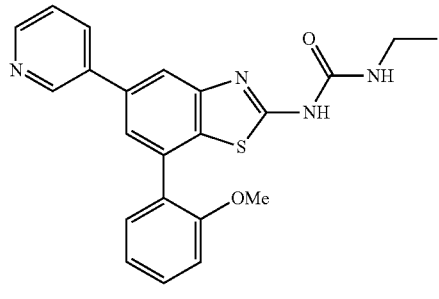 [SMILES: CCNC(=O)Nc1nc2cc(-c3cccnc3)cc(-c3ccccc3OC)c2s1] |
| 88 | 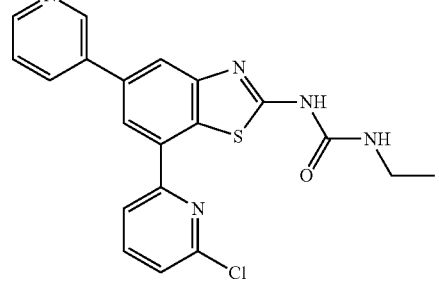 |

TABLE 1-continued
Structures of the examples described herein
| Example number | Structure |
|---|---|
| 89 | 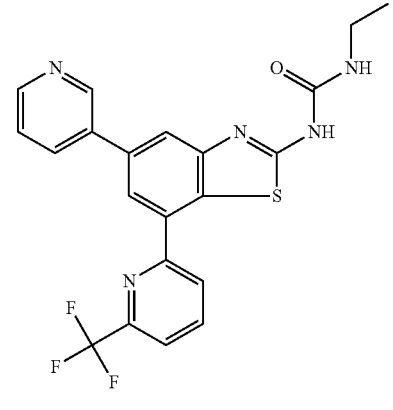 |
| 90 | 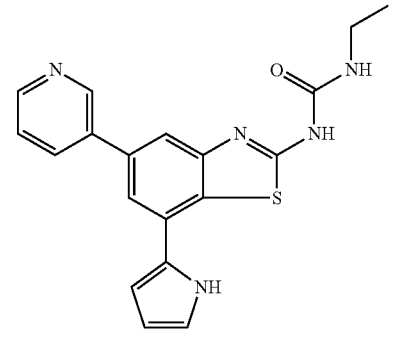 |
| 90 | 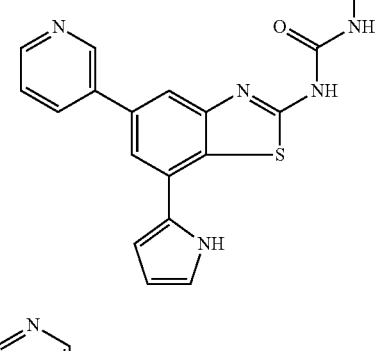 |
| 91 | 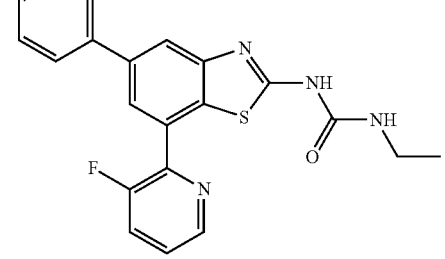 |

TABLE 1-continued

Structures of the examples described herein

| Example number | Structure |
|---|---|
| 92 | 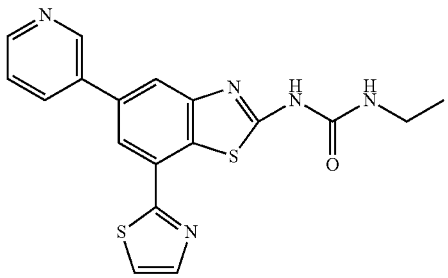 [SMILES: CCNC(=O)Nc1nc2cc(-c3cccnc3)cc(-c3nccs3)c2s1] |
| 93 | 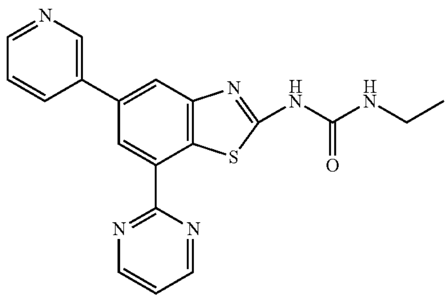 [SMILES: CCNC(=O)Nc1nc2cc(-c3cccnc3)cc(-c3ncccn3)c2s1] |
| 94 | 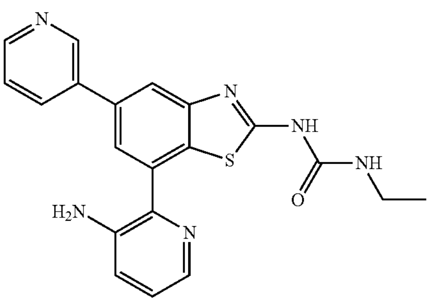 [SMILES: CCNC(=O)Nc1nc2cc(-c3cccnc3)cc(-c3ncccc3N)c2s1] |
| 95 | 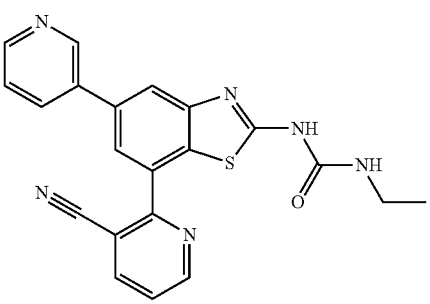 [SMILES: CCNC(=O)Nc1nc2cc(-c3cccnc3)cc(-c3ncccc3C#N)c2s1] |
| 96 | 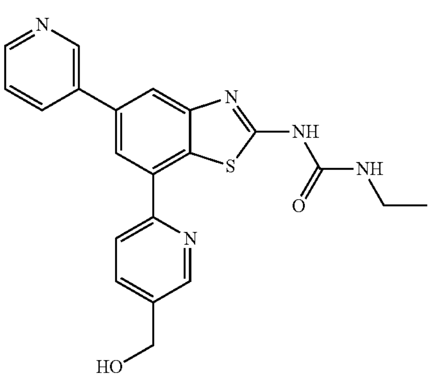 [SMILES: CCNC(=O)Nc1nc2cc(-c3cccnc3)cc(-c3ccc(CO)cn3)c2s1] |

TABLE 1-continued

Structures of the examples described herein

| Example number | Structure |
|---|---|
| 97 | (chemical structure) |
| 98 | (chemical structure) |
| 99 | (chemical structure) |
| 100 | (chemical structure) |

TABLE 1-continued

Structures of the examples described herein

| Example number | Structure |
|---|---|
| 101 | 5-(pyridin-3-yl)-7-(pyrazin-2-yl)benzothiazol-2-yl ethylurea |
| 102 | 5-(pyridin-3-yl)-7-(2,4-dimethylthiazol-5-yl)benzothiazol-2-yl ethylurea |
| 103 | 5-(pyridin-3-yl)-7-(3-cyano-6-methylpyridin-2-yl)benzothiazol-2-yl ethylurea |
| 104 | 5-(pyridin-3-yl)-7-(6-(hydroxymethyl)pyridin-2-yl)thiazolopyridin-2-yl ethylurea |

TABLE 1-continued
Structures of the examples described herein
| Example number | Structure |
|---|---|
| 105 | 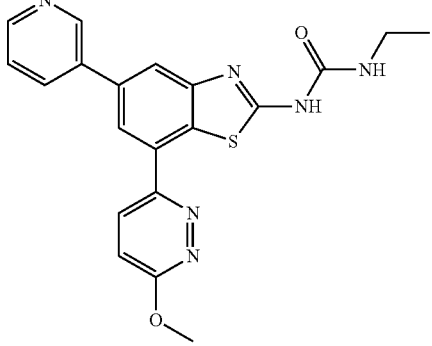 |
| 106 | 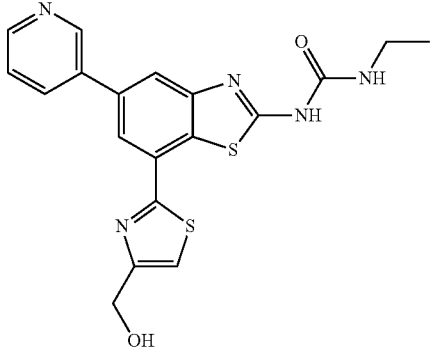 [SMILES: CCNC(=O)Nc1nc2cc(-c3cccnc3)cc(-c3nc(CO)cs3)c2s1] |
| 107 | 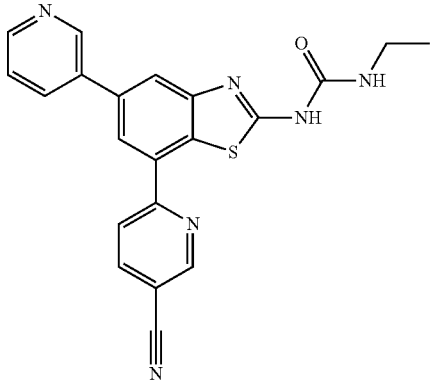 [SMILES: CCNC(=O)Nc1nc2cc(-c3cccnc3)cc(-c3ccc(C#N)cn3)c2s1] |
| 108 | 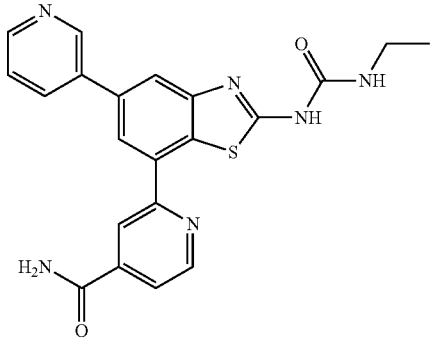 [SMILES: CCNC(=O)Nc1nc2cc(-c3cccnc3)cc(-c3cc(C(N)=O)ccn3)c2s1] |

TABLE 1-continued
Structures of the examples described herein
| Example number | Structure |
|---|---|
| 109 | 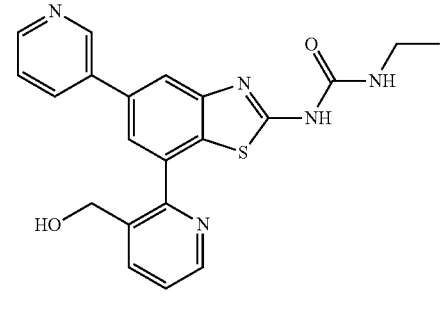 [SMILES: CCNC(=O)Nc1nc2cc(-c3cccnc3)cc(-c3ncccc3CO)c2s1] |
| 110 | 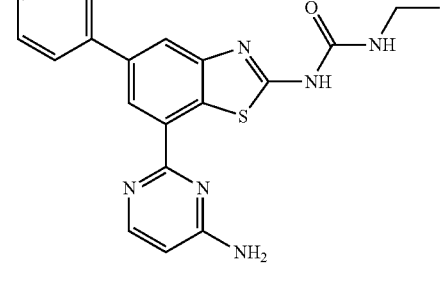 |
| 111 | 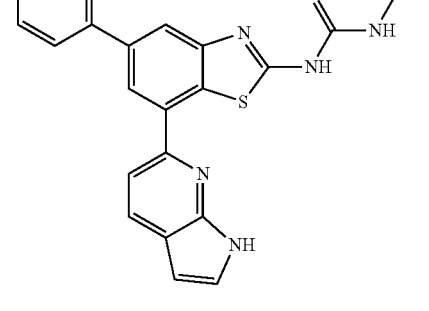 |
| 112 | 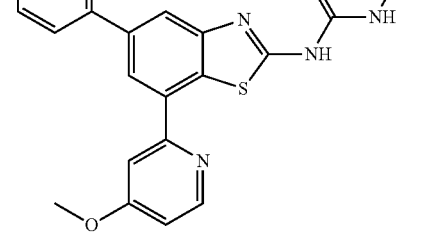 |

TABLE 1-continued
Structures of the examples described herein
| Example number | Structure |
| --- | --- |
| 113 | 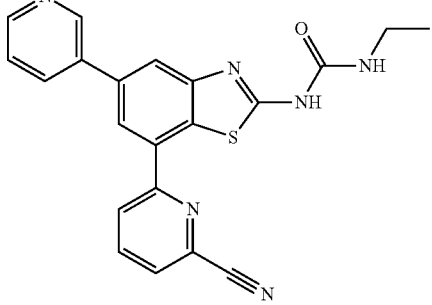 |
| 114 | 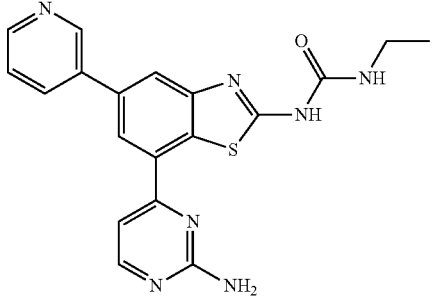 [SMILES: CCNC(=O)Nc1nc2cc(-c3cccnc3)cc(-c3nccc(N)n3)c2s1] |
| 115 | 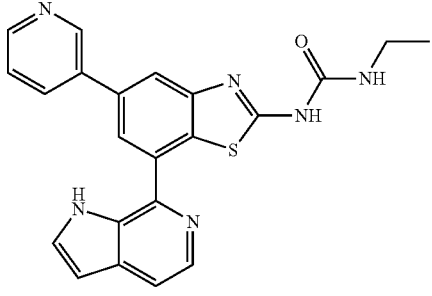 [SMILES: CCNC(=O)Nc1nc2cc(-c3cccnc3)cc(-c3nccc4cc[nH]c34)c2s1] |
| 116 | 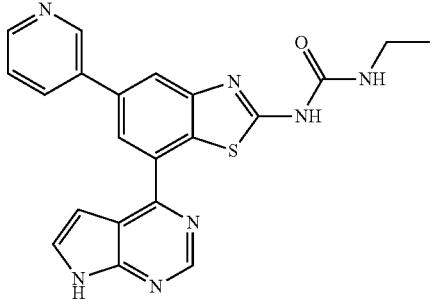 [SMILES: CCNC(=O)Nc1nc2cc(-c3cccnc3)cc(-c3ncnc4[nH]ccc34)c2s1] |

TABLE 1-continued
Structures of the examples described herein
| Example number | Structure |
|---|---|
| 117 | 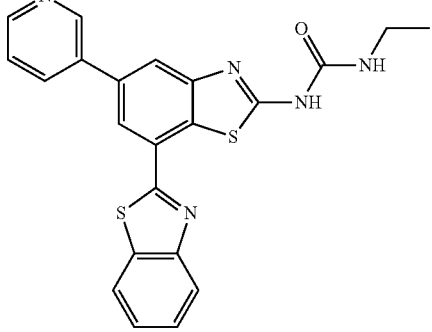 |
| 118 | 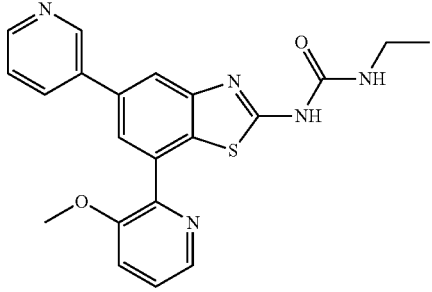 |
| 119 | 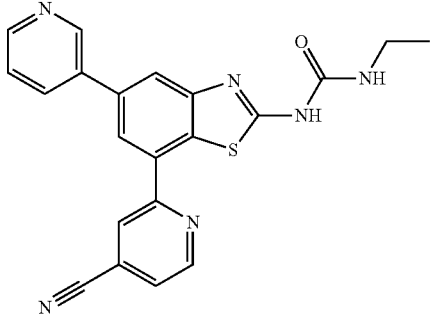 [SMILES: CCNC(=O)Nc1nc2cc(-c3cccnc3)cc(-c3cc(C#N)ccn3)c2s1] |
| 120 | 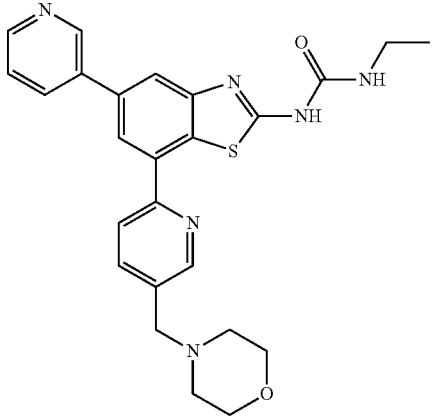 [SMILES: CCNC(=O)Nc1nc2cc(-c3cccnc3)cc(-c3ccc(CN4CCOCC4)cn3)c2s1] |

TABLE 1-continued

Structures of the examples described herein

| Example number | Structure |
|---|---|
| 121 | (structure) |
| 122 | (structure) |
| 123 | (structure) |
| 124 | (structure) |
| 125 | (structure) |

TABLE 1-continued

Structures of the examples described herein

| Example number | Structure |
|---|---|
| 126 | 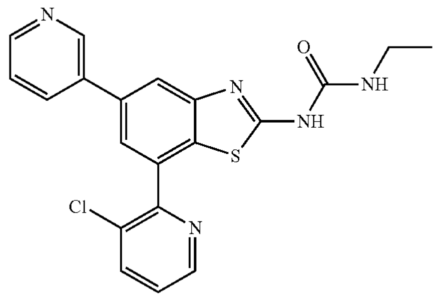 [SMILES: CCNC(=O)Nc1nc2cc(-c3cccnc3)cc(-c3ncccc3Cl)c2s1] |
| 127 | 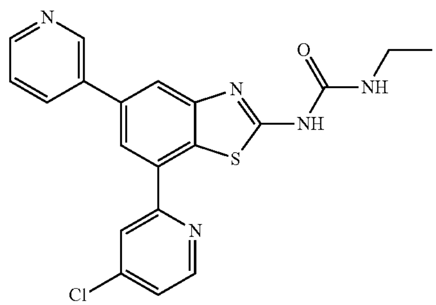 [SMILES: CCNC(=O)Nc1nc2cc(-c3cccnc3)cc(-c3cc(Cl)ccn3)c2s1] |
| 128 | 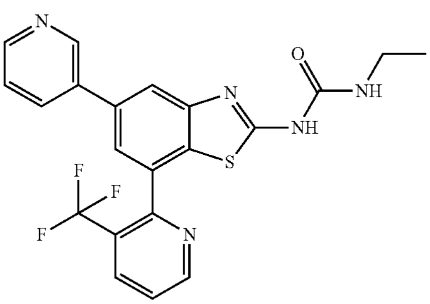 [SMILES: CCNC(=O)Nc1nc2cc(-c3cccnc3)cc(-c3ncccc3C(F)(F)F)c2s1] |
| 129 | 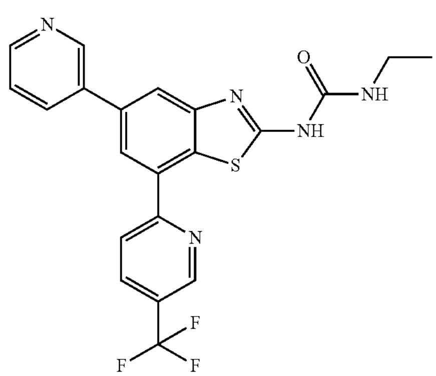 [SMILES: CCNC(=O)Nc1nc2cc(-c3cccnc3)cc(-c3ccc(C(F)(F)F)cn3)c2s1] |

TABLE 1-continued

Structures of the examples described herein

| Example number | Structure |
|---|---|
| 130 | 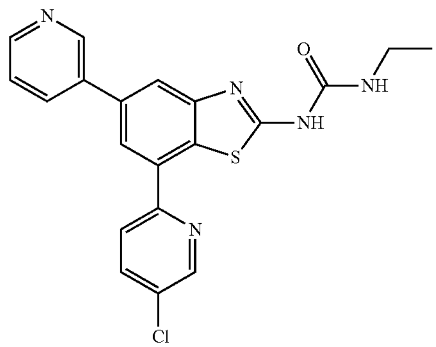 [SMILES: CCNC(=O)Nc1nc2cc(-c3cccnc3)cc(-c3ccc(Cl)cn3)c2s1] |
| 131 | 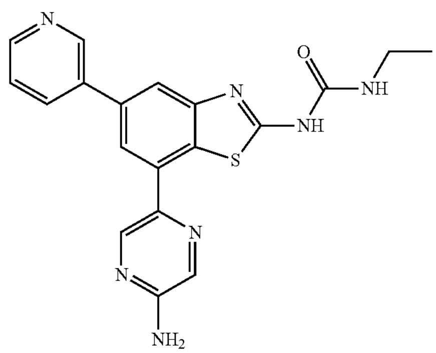 [SMILES: CCNC(=O)Nc1nc2cc(-c3cccnc3)cc(-c3cnc(N)cn3)c2s1] |
| 132 | 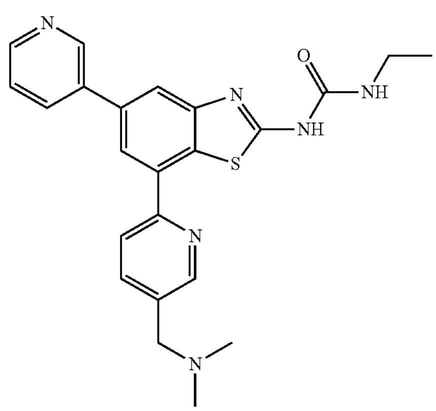 [SMILES: CCNC(=O)Nc1nc2cc(-c3cccnc3)cc(-c3ccc(CN(C)C)cn3)c2s1] |
| 133 | 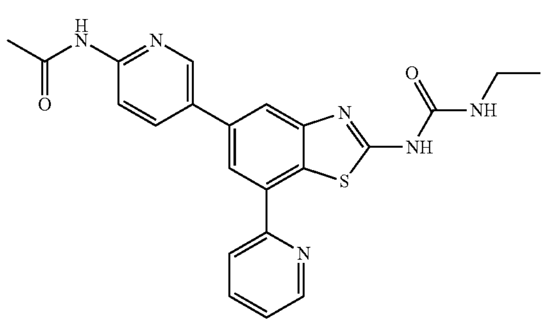 [SMILES: CCNC(=O)Nc1nc2cc(-c3ccc(NC(C)=O)nc3)cc(-c3ccccn3)c2s1] |

TABLE 1-continued

Structures of the examples described herein

| Example number | Structure |
|---|---|
| 134 | 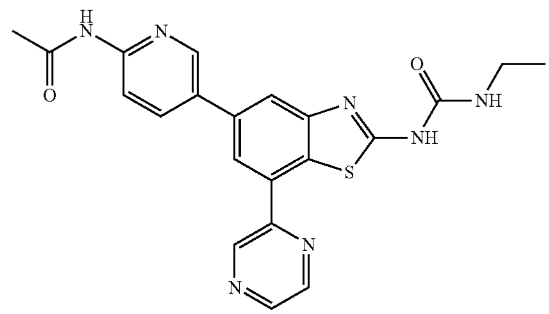 [SMILES: CCNC(=O)Nc1nc2cc(-c3ccc(NC(C)=O)nc3)cc(-c3cnccn3)c2s1] |
| 135 | 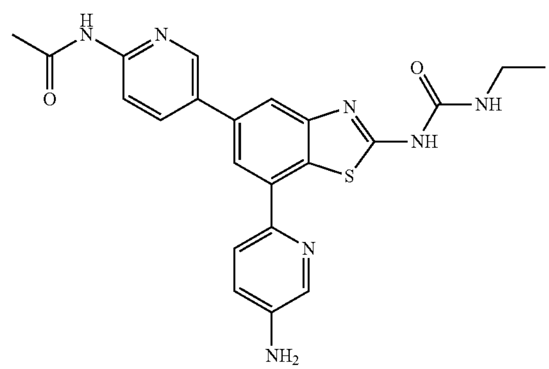 [SMILES: CCNC(=O)Nc1nc2cc(-c3ccc(NC(C)=O)nc3)cc(-c3ccc(N)cn3)c2s1] |
| 136 | 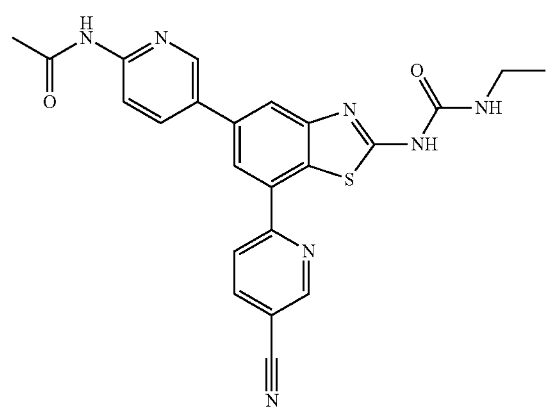 [SMILES: CCNC(=O)Nc1nc2cc(-c3ccc(NC(C)=O)nc3)cc(-c3ccc(C#N)cn3)c2s1] |
| 137 | 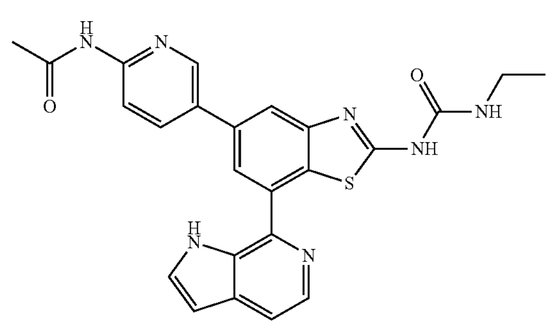 [SMILES: CCNC(=O)Nc1nc2cc(-c3ccc(NC(C)=O)nc3)cc(-c3nccc4cc[nH]c34)c2s1] |

TABLE 1-continued

Structures of the examples described herein

| Example number | Structure |
|---|---|
| 138 | 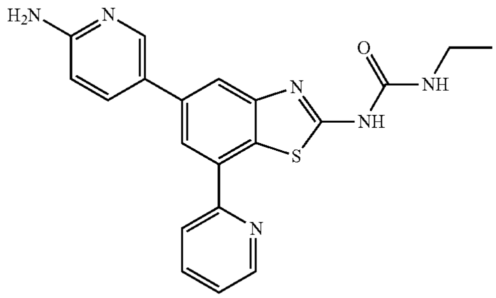 [SMILES: CCNC(=O)Nc1nc2cc(-c3ccc(N)nc3)cc(-c3ccccn3)c2s1] |
| 139 | 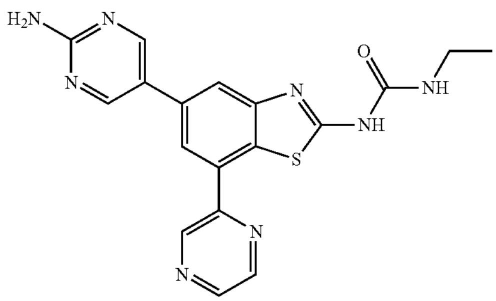 |
| 140 | 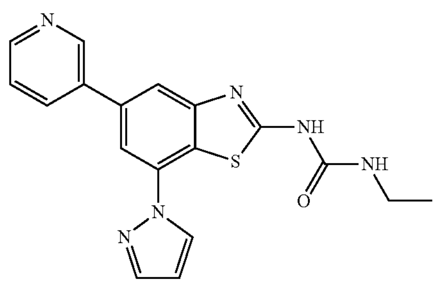 [SMILES: CCNC(=O)Nc1nc2cc(-c3cccnc3)cc(-n3cccn3)c2s1] |
| 141 | 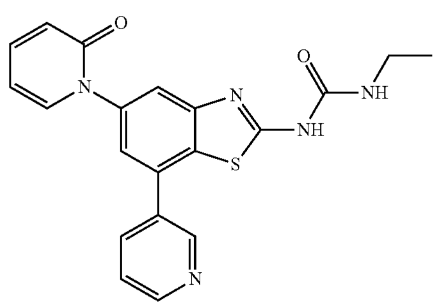 [SMILES: CCNC(=O)Nc1nc2cc(-n3ccccc3=O)cc(-c3cccnc3)c2s1] |
| 142 | 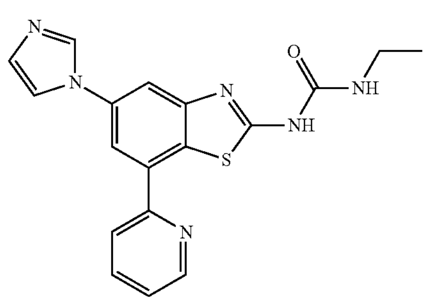 [SMILES: CCNC(=O)Nc1nc2cc(-n3ccnc3)cc(-c3ccccn3)c2s1] |

TABLE 1-continued

Structures of the examples described herein

| Example number | Structure |
|---|---|
| 143 | (structure) |
| 144 | (structure) |
| 145 | (structure) |
| 146 | (structure) |

TABLE 1-continued

Structures of the examples described herein

| Example number | Structure |
|---|---|
| 147 | 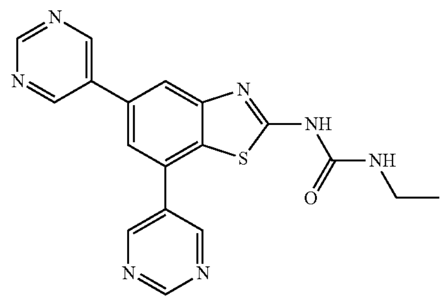 [SMILES: CCNC(=O)Nc1nc2cc(-c3cncnc3)cc(-c3cncnc3)c2s1] |
| 148 | 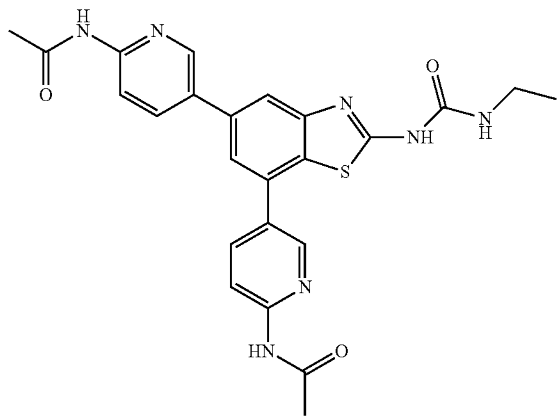 [SMILES: CCNC(=O)Nc1nc2cc(-c3ccc(NC(C)=O)nc3)cc(-c3ccc(NC(C)=O)nc3)c2s1] |
| 149 | 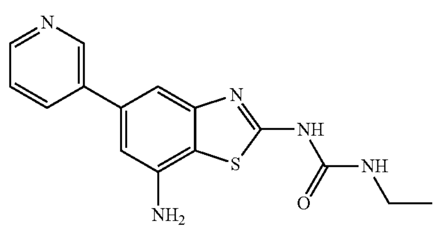 [SMILES: CCNC(=O)Nc1nc2cc(-c3cccnc3)cc(N)c2s1] |
| 150 | |
| 150 | |

TABLE 1-continued

Structures of the examples described herein

| Example number | Structure |
|---|---|
| 151 | 5-(pyridin-3-yl)-2-(3-ethylureido)benzothiazole-7-carboxylic acid methyl ester |
| 152 | 5-(pyridin-3-yl)-2-(3-ethylureido)-N-ethylbenzothiazole-7-carboxamide |
| 153 | 5-(pyridin-3-yl)-2-(3-ethylureido)benzothiazole-7-carbohydrazide |
| 154 | 5-(2-aminopyrimidin-5-yl)-7-(pyridin-2-yl)-2-(3-ethylureido)benzothiazole |
| 155 | 5-(pyridin-2-yl)-7-(pyridin-3-yl)-benzothiazol-2-yl—NHCONHEt |

TABLE 1-continued

Structures of the examples described herein

| Example number | Structure |
|---|---|
| 156 | (structure) |
| 157 | (structure) |
| 158 | (structure) |
| 159 | (structure) |
| 160 | (structure) |

TABLE 1-continued

Structures of the examples described herein

| Example number | Structure |
|---|---|
| 161 | (structure) |
| 162 | (structure) |
| 163 | (structure) |
| 164 | (structure) |
| 165 | (structure) |

TABLE 1-continued
Structures of the examples described herein
| Example number | Structure |
|---|---|
| 166 | 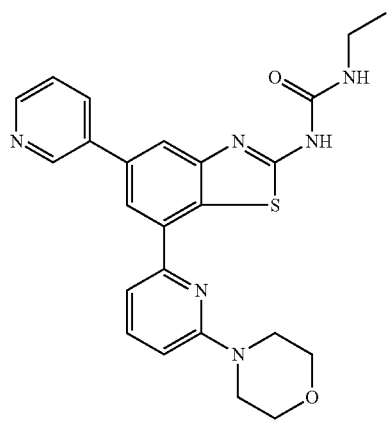 [SMILES: CCNC(=O)Nc1nc2cc(-c3cccnc3)cc(-c3cccc(N4CCOCC4)n3)c2s1] |
| 167 | 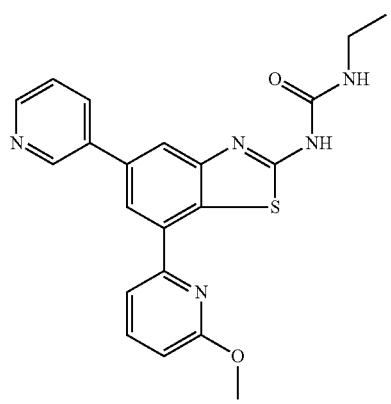 [SMILES: CCNC(=O)Nc1nc2cc(-c3cccnc3)cc(-c3cccc(OC)n3)c2s1] |
| 168 | 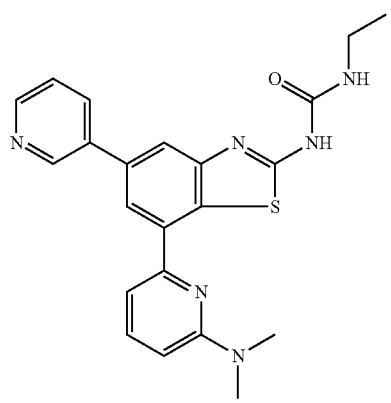 [SMILES: CCNC(=O)Nc1nc2cc(-c3cccnc3)cc(-c3cccc(N(C)C)n3)c2s1] |

TABLE 1-continued
Structures of the examples described herein
| Example number | Structure |
|---|---|
| 169 | 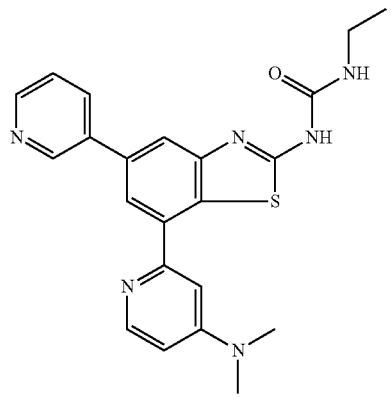 [SMILES: CCNC(=O)Nc1nc2cc(-c3cccnc3)cc(-c3cc(N(C)C)ccn3)c2s1] |
| 170 | 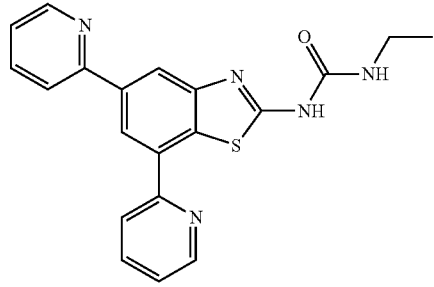 [SMILES: CCNC(=O)Nc1nc2cc(-c3ccccn3)cc(-c3ccccn3)c2s1] |
| 171 | no example 171 |
| 172 | 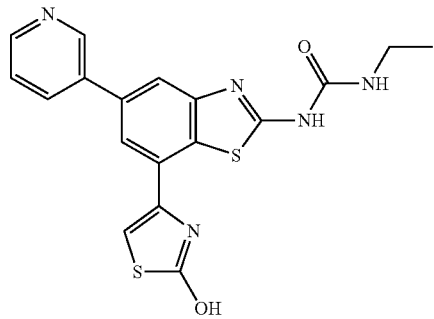 [SMILES: CCNC(=O)Nc1nc2cc(-c3cccnc3)cc(-c3csc(O)n3)c2s1] |
| 173 | 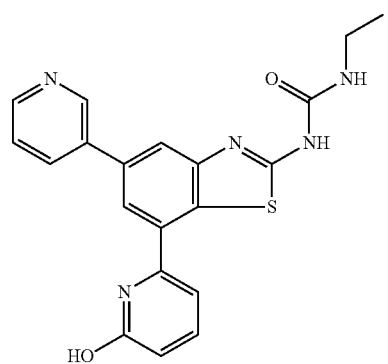 |

TABLE 1-continued
Structures of the examples described herein
| Example number | Structure |
|---|---|
| 174 | 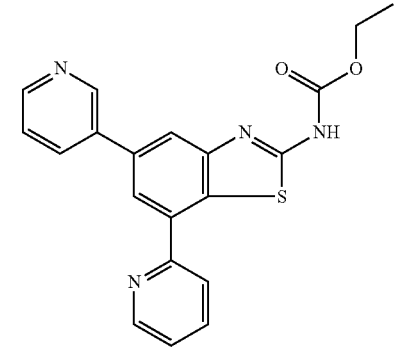 |
| 175 | 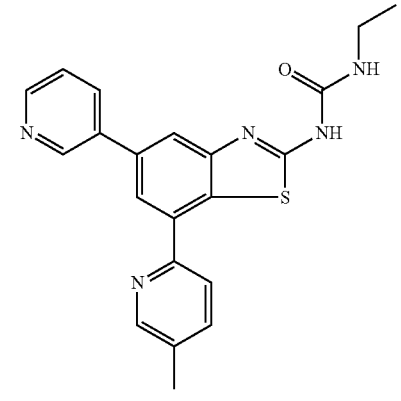 |
| 176 | 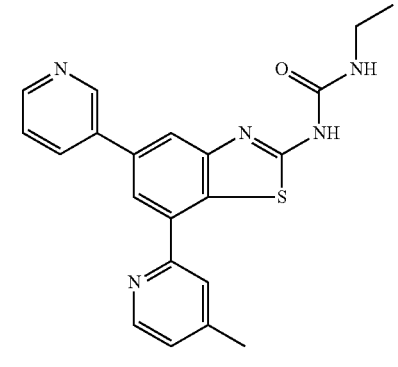 |
| 177 | 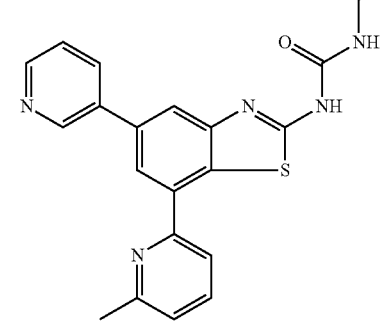 |

TABLE 1-continued

Structures of the examples described herein

| Example number | Structure |
|---|---|
| 178 | no example 178 |
| 179 | [structure] |

Biological Data

Minimum Inhibitory Concentration (MIC) Testing

Compounds of this invention were tested for antimicrobial activity by susceptibility testing in liquid or on solid media. MICs for compounds against each strain were determined by the broth microdilution or agar dilution method according to the guidelines of the Clinical Laboratories and Standards Institute, formerly the National Committee for Clinical Laboratory Standards (Clinical Laboratories and Standards Institute. *Methods for Dilution Antimicrobial Susceptibility Tests for Bacteria That Grow Aerobically; Approved Standard—Seventh Edition.* Document M7-A7. CLSI, Wayne, Pa., 2006; Clinical Laboratories and Standards Institute. *Methods for Antimicrobial Susceptibility Testing of Anaerobic Bacteria; Approved Standard—Sixth Edition. Document M*11-A6. CLSI, Wayne, Pa., 2004). MICs against *Chlamydia trachomatis* and *Chlamydophila pneumoniae* were measured using the microtitre tissue culture incorporation technique with demonstration of inclusions by immunofluorescence straining.

Compounds of the current invention were found to have antimicrobial activity in the MIC assays described above.

Gyrase ATPase Assay

Gyrase converts ATP into ADP and inorganic phosphate. The released phosphate can be detected by the addition of malachite green solution and measured by monitoring the increase in absorbance at 600 nm.

The ATPase assay is carried out in a buffer containing 4.8 μg/ml Gyrase enzyme ($A_2B_2$ complex from *Escherichia coli*), 0.08 μg/ml ssDNA, 35 mM Tris pH 7.5, 24 mM KCl, 2 mM $MgCl_2$, 6.5% Glycerol, 2 mM DTT, 1.8 mM Spermidine, 0.5 mg/ml BSA, and 5% DMSO solution containing the inhibitor. The reaction is started by adding ATP to a final concentration of 1 mM and allowed to incubate at 30° C. for 60 minutes. The reaction is stopped by adding 200 μl of malachite green solution (0.034% malachite green, 10 mM ammonium molybdate, 1 M HCl, 3.4% ethanol, 0.01% tween 20). Colour is allowed to develop for 5 minutes and the absorbance at 600 nm is measured spectrophotometrically. The $IC_{50}$ values are determined from the absorbance readings using no compound and no enzyme controls.

All Example compounds above of the current invention were found to inhibit the gyrase ATPase assay described above, with 50% inhibitory concentrations ($IC_{50}$) of less than 0.75 micro molar.

All of the Examples inhibited the growth of bacteria. Table 2 shows the MIC value for each Example against *Enterococcus faecalis* ATCC 29212 in the MIC Assay described above. Examples with activity "C" demonstrate MICs of 2-16 μg/ml. Examples with activity "B" demonstrate MICs of 0.25-1 μg/ml. Examples with activity "A" demonstrate MICs of <0.25 μg/ml.

TABLE 2

MICs against *Enterococcus faecalis*

| Example number | Activity |
|---|---|
| 1 | C |
| 2 | C |
| 3 | B |
| 4 | B |
| 5 | C |
| 6 | B |
| 7 | B |
| 8 | C |
| 9 | B |
| 10 | A |
| 11 | B |
| 12 | C |
| 13 | B |
| 14 | B |
| 15 | B |
| 16 | C |
| 17 | B |
| 18 | C |
| 19 | B |
| 20 | B |
| 21 | C |
| 22 | B |
| 23 | C |
| 24 | B |
| 25 | B |
| 26 | B |
| 27 | A |
| 28 | B |
| 29 | B |
| 30 | B |
| 31 | B |
| 32 | C |
| 33 | A |
| 34 | A |
| 35 | A |
| 36 | A |
| 37 | B |
| 38 | B |
| 39 | B |
| 40 | B |
| 41 | A |
| 42 | B |

TABLE 2-continued

MICs against *Enterococcus faecalis*

| Example number | Activity |
|---|---|
| 43 | B |
| 44 | C |
| 45 | B |
| 46 | C |
| 47 | B |
| 48 | B |
| 49 | B |
| 50 | B |
| 51 | A |
| 52 | B |
| 53 | A |
| 54 | B |
| 55 | B |
| 56 | B |
| 57 | B |
| 58 | A |
| 59 | A |
| 60 | B |
| 61 | B |
| 62 | B |
| 63 | B |
| 64 | C |
| 65 | B |
| 66 | B |
| 67 | B |
| 68 | B |
| 69 | A |
| 70 | A |
| 71 | A |
| 72 | B |
| 73 | C |
| 74 | C |
| 75 | B |
| 76 | B |
| 77 | B |
| 78 | B |
| 79 | B |
| 80 | B |
| 81 | C |
| 82 | B |
| 83 | B |
| 84 | B |
| 85 | B |
| 86 | B |
| 87 | B |
| 88 | A |
| 89 | A |
| 90 | B |
| 91 | A |
| 92 | A |
| 93 | B |
| 94 | C |
| 95 | A |
| 96 | A |
| 97 | B |
| 98 | B |
| 99 | A |
| 100 | A |
| 101 | A |
| 102 | B |
| 103 | A |
| 104 | A |
| 105 | B |
| 106 | B |
| 107 | A |
| 108 | B |
| 109 | C |
| 110 | A |
| 111 | A |
| 112 | A |
| 113 | A |
| 114 | A |
| 115 | A |
| 116 | A |
| 117 | A |

TABLE 2-continued

MICs against *Enterococcus faecalis*

| Example number | Activity |
|---|---|
| 118 | A |
| 119 | A |
| 120 | B |
| 121 | A |
| 122 | A |
| 123 | A |
| 124 | A |
| 125 | A |
| 126 | A |
| 127 | A |
| 128 | B |
| 129 | B |
| 130 | A |
| 131 | A |
| 132 | C |
| 133 | A |
| 134 | A |
| 135 | B |
| 136 | A |
| 137 | B |
| 138 | A |
| 139 | A |
| 140 | B |
| 141 | C |
| 142 | A |
| 143 | B |
| 144 | B |
| 145 | C |
| 146 | C |
| 147 | C |
| 148 | B |
| 149 | C |
| 150 | C |
| 151 | B |
| 152 | C |
| 153 | C |
| 154 | A |
| 155 | C |
| 156 | B |
| 157 | B |
| 158 | B |
| 159 | B |
| 160 | C |
| 161 | A |
| 162 | C |
| 163 | A |
| 164 | C |
| 165 | B |
| 166 | B |
| 167 | A |
| 168 | B |
| 169 | B |
| 170 | B |
| No 171 | |
| 172 | C |
| 173 | C |
| 174 | A |
| 175 | A |
| 176 | A |
| 177 | A |
| No 178 | |
| 179 | A |

Some of the Example compounds were also tested for activity against other bacterial species. For example, Table 3 shows the MICs of Example 163 against various bacterial species. Activity "C" demonstrates an MIC of 2-16 µg/ml. Activity "B" demonstrates an MIC of 0.25-1 µg/ml. Activity "A" demonstrates an MIC of <0.25 µg/ml.

TABLE 3

MICs against various bacteria

| Species | Isolate ID | Activity |
|---|---|---|
| Bacteroides fragilis | ATCC 25285 | C |
| Chlamydia trachomatis | T71214 | B |
| Chlamydophila pneumoniae | IOL207 | A |
| Clostridium difficile | NQS 84 | B |
| Clostridium perfringens | IV306001 | B |
| Enterococcus faecalis (VRE) | ATCC 51299 | A |
| Enterococcus faecium (VRE) | ATCC 700221 | A |
| Enterococcus faecium (VSE) | ATCC 19434 | B |
| Escherichia coli | N43 | C |
| Haemophilus influenzae | ATCC 49247 | C |
| Helicobacter pylori | DJF 11 | A |
| Lactococcus lactis | ATCC 11454 | A |
| Legionella pneumophila | LP NCTC 11192 | B |
| Listeria monocytogenes | ATCC 19115 | A |
| Moraxella catarrhalis | ATCC 25240 | A |
| Mycoplasma hominis | MH NCTC 10111 | B |
| Mycoplasma hominis | MH 10 | B |
| Mycoplasma pneumoniae | MP 9 | B |
| Mycoplasma pneumoniae | MP NCTC 10119 | B |
| Neisseria gonorrhoeae | NG ATCC 49226 | B |
| Propionibacterium acnes | ATCC 11821 | A |
| Staphylococcus aureus | ATCC 29213 | B |
| Staphylococcus aureus | VRS1 | A |
| Staphylococcus aureus | VRS2 | A |
| Staphylococcus aureus | VRS3 | A |
| Staphylococcus epidermidis | ATCC 12228 | A |
| Staphylococcus haemolyticus | ATCC 29970 | A |
| Streptococcus mutans | ATCC 35668 | A |
| Streptococcus pneumoniae | ATCC 700671 | A |
| Streptococcus pneumoniae | SP 051430 | A |
| Streptococcus pneumoniae (FQR) | SP 26054 | A |
| Streptococcus pneumoniae (FQR) | SP 25058 | A |
| Streptococcus pneumoniae (MacR) | SP 051431 | A |
| Streptococcus pyogenes | ATCC 51339 | B |

Some of the Example compounds were also tested for activity in a mouse *Staphylococcus aureus* septicaemia model of infection. For example, Table 4 shows the survival at day 7 of infected mice treated as indicated with one or two intraperitoneal doses of each of the compounds of Examples 4, 91 and 163 at 1 hour or 1 and 6 hours after intraperitoneal inoculation with a lethal dose of *Staphylococcus aureus*.

TABLE 4

Murine Survival

| Example | Dose | Percent survival |
|---|---|---|
| Vehicle control | n/a | 0 |
| Example 4 | 2 × 100 mg/kg | 100 |
| Example 163 | 2 × 30 mg/kg | 100 |
| Example 91 | 2 × 30 mg/kg | 100 |
| Example 163 | 1 × 30 mg/kg | 100 |
| Example 163 | 1 × 10 mg/kg | 60 |

The invention claimed is:

1. A method of treating a subject suffering from a bacterial infection or a community acquired bacterial pneumonia (CAPB), comprising administering to said subject an antibacterially effective amount of a compound of formula (I), or a salt or N-oxide thereof:

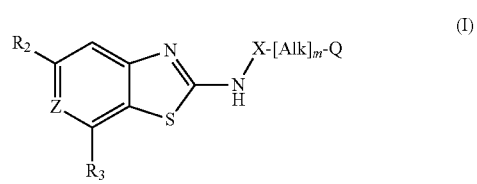

wherein:
m is 0 or 1;
Q is hydrogen or cyclopropyl;
Alk is an optionally substituted, divalent $C_1$-$C_6$ alkylene, alkenylene or alkynylene radical which may contain an ether (—O—), thioether (—S—) or amino (—NR)— link, wherein R is hydrogen, —CN or $C_1$-$C_3$ alkyl;
X is —C(=O)NR$_6$—, —S(O)NR$_6$—, —C(=O)O— or —S(=O)O— wherein R$_6$ is hydrogen, optionally substituted $C_1$-$C_6$ alkyl, $C_2$-$C_6$ alkenyl, $C_2$-$C_6$ alkynyl, -Cyc, or —($C_1$-$C_3$ alkyl)-Cyc wherein Cyc is optionally substituted monocyclic carbocyclic or heterocyclic having 3-7 ring atoms;
Z is N or CR, or CF;
R$_2$ is a group Q$^1$-[Alk$^1$]$_q$-Q$^2$-, wherein
q is 0 or 1;
Alk$^1$ is an optionally substituted, divalent, straight chain or branched $C_1$-$C_6$ alkylene, or $C_2$-$C_6$ alkenylene or $C_2$-$C_6$ alkynylene radical which may contain or terminate in an ether (—O—), thioether (—S—) or amino (—NR)-link;
Q$^2$ is an optionally substituted divalent monocyclic carbocyclic or heterocyclic radical having 5 or 6 ring atoms or an optionally substituted divalent bicyclic carbocyclic or heterocyclic radical having 9 or 10 ring atoms;
Q$^1$ is hydrogen, an optional substituent, or an optionally substituted carbocyclic or heterocyclic radical having 3-7 ring atoms;
R$_3$ is a group Q$^4$-[Alk$^2$]$_p$-[Q$^3$]$_q$- other than hydrogen wherein
p and q are independently 0 or 1;
Alk$^2$ is optionally substituted divalent $C_1$-$C_6$ alkylene or $C_2$-$C_6$ alkenylene or $C_2$-$C_6$ alkynylene radical;
Q$^3$ is an optionally substituted divalent monocyclic carbocyclic or heterocyclic radical having 5 or 6 ring atoms or an optionally substituted divalent bicyclic carbocyclic or heterocyclic radical having 9 or 10 ring atoms;
Q$^4$ is hydrogen, an optional substituent, or optionally substituted carbocyclic or heterocyclic ring having 3-7 ring atoms;
wherein the bacterial infection or CAPB is caused by (i) a Gram positive bacteria selected from the group consisting of *Staphylococci*, *Enterococci*, *Streptococci*, *Clostridia*, *Lactococci*, *Listeria*, *Propionibacteria* and *Mycobacteria*; (ii) a Gram negative bacteria selected from the group consisting of *Haemophili*, *Moraxellas*, *Legionellas*, *Bacteroides*, *Escherichia*, *Helicobacter* and *Neisseria*; or (iii) an atypical bacteria selected from the group consisting of *Chlamydophilas*, *Mycoplasmas* and *Chlamydia*.

2. The method as claimed in claim 1 wherein, in the said compound, Z is CH.

3. The method as claimed in claim 1 wherein, in the said compound, m is 1 and Q is hydrogen.

4. The method as claimed in claim 1 wherein, in the said compound, X is —C(O)NH—.

5. The method as claimed in claim 1 wherein, in the said compound, m is 1, Q is hydrogen, Alk is —CH$_2$CH$_2$—, and X is —C(O)NH—.

6. The method as claimed in claim 1 wherein, in the substituent $R_2$ of the said compound, $Q^2$ is an optionally substituted pyridine, pyrimidine, or pyrazine.

7. The method of claim 6 wherein $Q^2$ is an optionally substituted pyridine-2-one ring.

8. The method as claimed in claim 1 wherein, in the substituent $R_2$ of the said compound, $Q^2$ is an optionally substituted pyridine-3-yl ring, an optionally substituted pyrimidine-5-yl ring, an optionally substituted pyrazine-2-yl ring or an optionally substituted pyridine-2-one-4-yl ring.

9. The method as claimed in claim 1 wherein, in the substituent $R_2$ of the said compound, optional substituents in $Q^2$ are selected from $CH_3$—, $CH_3O$—, —CN, and —$NH_2$.

10. The method as claimed in claim 1 wherein, in the substituent $R_2$ of the said compound, $Alk^1$ is present and is an optionally substituted divalent $C_1$-$C_3$ alkylene radical.

11. The method as claimed in claim 10 wherein, in the substituent $R_2$ of the said compound, $Q^1$ is a primary, secondary or cyclic amino group.

12. The method as claimed in claim 10 wherein, in the substituent $R_2$, of the said compound, $Q^1$ is a group of formula —$NR^A R^B$, wherein $R^A$ and $R^B$ are independently hydrogen or a ($C_1$-$C_6$)alkyl, hydroxy($C_1$-$C_6$)alkyl, or ($C_1$-$C_3$)alkoxy($C_1$-$C_3$)alkyl group.

13. The method as claimed in claim 10 wherein, in the substituent $R_2$ of the said compound, $Q^1$ is a group of formula —$NR^A R^B$, wherein $R^A$ and $R^B$ taken together with that nitrogen form a cyclic amino ring.

14. The method as claimed in claim 13 wherein the cyclic amino ring is a morpholinyl, piperidinyl, or piperazinyl ring.

15. The method as claimed in claim 1 wherein, in the substituent $R_2$ of the said compound, $Alk^1$ is present and is an optionally substituted divalent $C_1$-$C_3$ alkylene radical which includes an —NH— link, or optionally terminates in an —NH— link to $Q^2$.

16. The method as claimed in claim 15 wherein $Alk^1$ is a divalent $C_2$-$C_3$ alkylene radical which terminates in an —NH— link to $Q^2$, and which is oxo-substituted on the C atom adjacent that —NH— link, whereby $Alk^1$ has the formula —$(CH_2)_{1-2}C(=O)NH$—.

17. The method as claimed in claim 15 wherein $Alk^1$ has the formula —$(CH_2)_{1-2}NHC(=O)$—, with the (C=O) being linked to $Q^2$.

18. The method as claimed in claim 1 wherein the substituent $R_2$ of the said compound is selected from the following radicals:

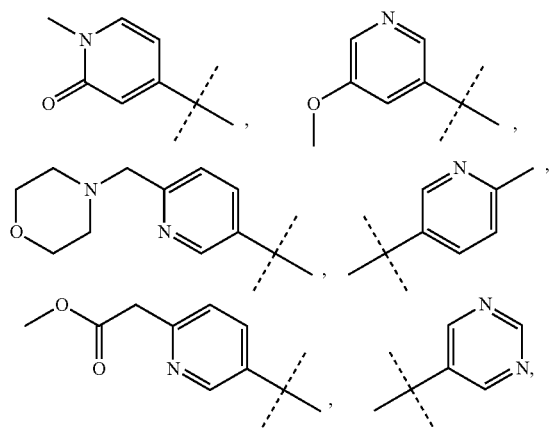

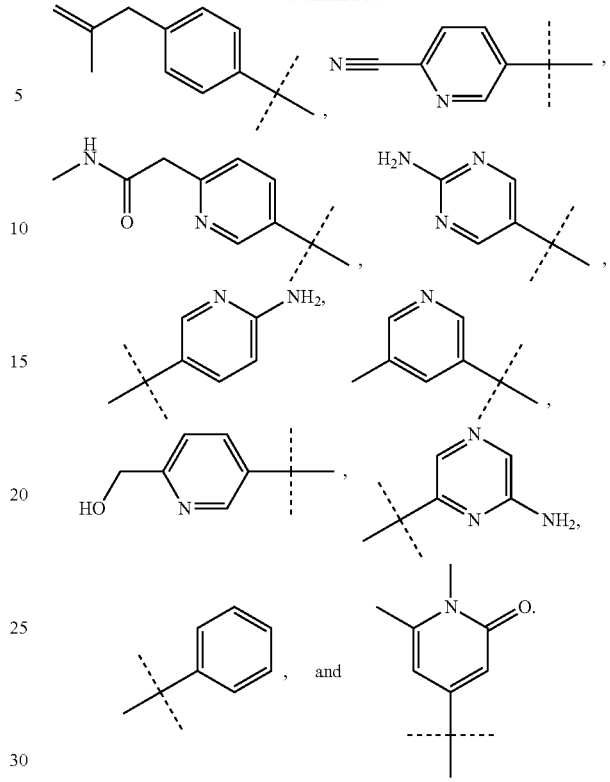

19. The method as claimed in claim 1 wherein, in the substituent $R_3$ of the said compound, q is 1.

20. The method as claimed in claim 19 wherein, in the substituent $R_3$ of the said compound, p is 1.

21. The method as claimed in claim 20 wherein, in the substituent $R_3$ of the said compound, $Alk^2$ is an optionally substituted divalent $C_1$-$C_3$ alkylene radical.

22. The method as claimed in claim 19 wherein, in the substituent $R_3$ of the said compound, $Q^4$ is hydrogen and p is 0.

23. The method as claimed in claim 19 wherein, in the substituent $R_3$ of the said compound, $Q^3$ is an optionally substituted pyridine ring an optionally substituted pyrimidine ring or an optionallly substituted pyrazine ring.

24. The method as claimed in claim 19 wherein, in the substituent $R_3$ of the said compound, $Q^3$ is an optionally substituted pyridine-2-yl ring, an optionally substituted pyrimidine-2-yl ring or an optionally substituted pyrazine-2-yl ring.

25. The method as claimed in claim 1 wherein, in the substituent $R_3$ of the said compound, optional substituents in $Q^3$ are selected from $CH_3O$—, —$NH_2$, —CN, Cl, $CH_3$—, and —$CF_3$.

26. The method as claimed in claim 1 wherein, in the substituent $R_3$ of the said compound, p and q are 0 and $Q^4$ is selected from halo, —$CONHR^A$, —$NHCONHR^B$, wherein $R^A$ and $R^B$ are hydrogen or a ($C_1$-$C_6$)alkyl, hydroxyl ($C_1$-$C_6$) alkyl, or ($C_1$-$C_3$)alkoxy($C_1$-$C_3$)alkyl group.

27. The method as claimed in claim 1 wherein the substituent $R_3$ of the said compound is selected from the following radicals:

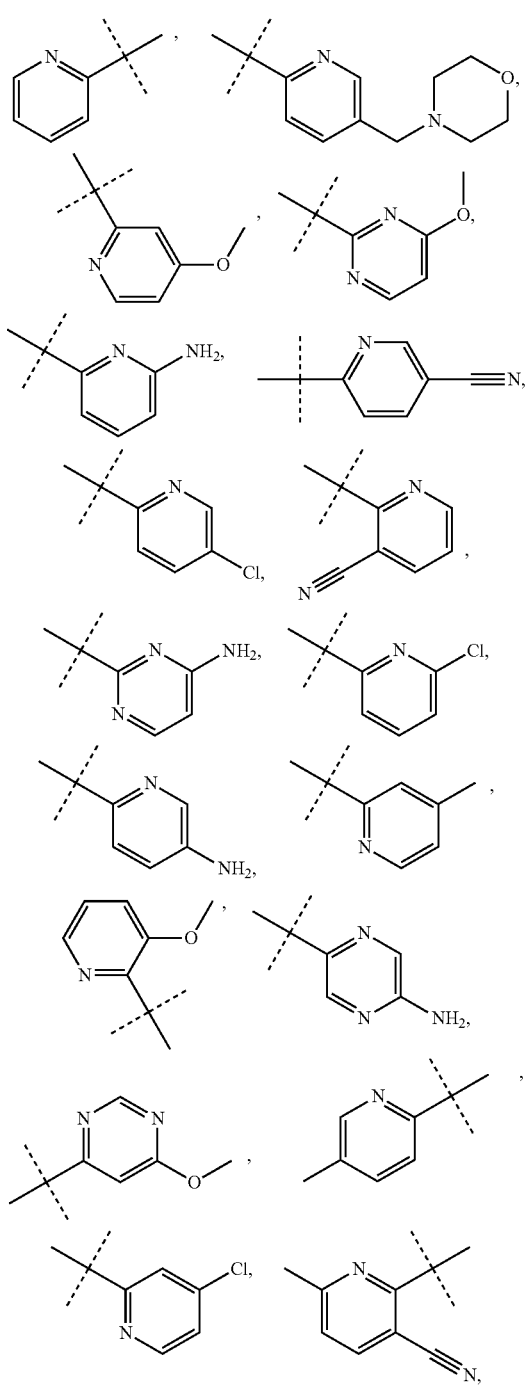

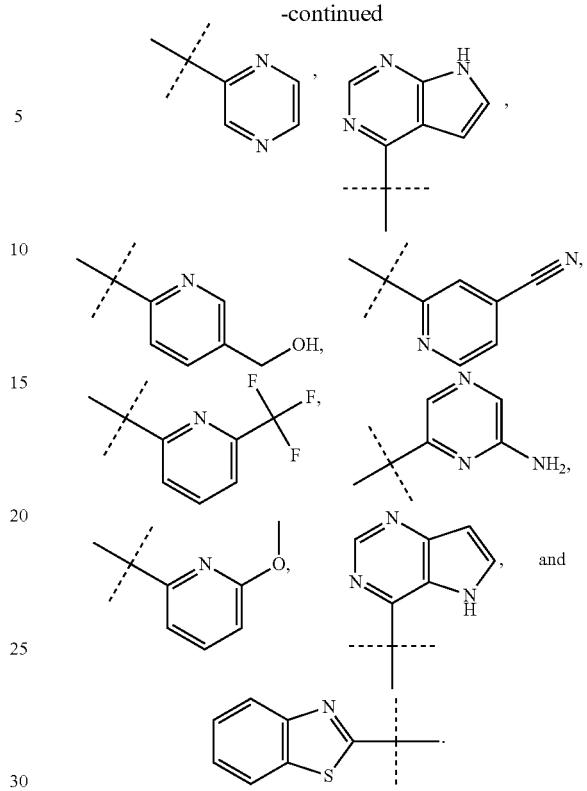

28. The method of claim 1, comprising applying a compound of formula (I) to a site of a bacterial contamination.

29. The method according to claim 1 where the species of Gram positive bacteria is selected from the group consisting of *Staphylococcus aureus, Staphylococcus epidermidis, Staphylococcus haemolyticus, Enterococcus faecalis* (VRE), *Enterococcus faecium* (VRE), *Enterococcus faecium* (VSE), *Streptococcus mutans, Streptococcus pneumoniae, Streptococcus pneumonia* (FQR), *Streptococcus pneumonia* (MacR), *Streptococcus pyogenes, Clostridium difficile, Clostridium perfringens, Lactococcus lactis, Listeria monocytogenes, Propionibacterium acnes, Mycobacterium tuberculosis* and *Mycobacterium avium*.

30. The method according to claim 1 where the species of Gram negative bacteria is selected from the group consisting of *Haemophilus influenzae, Moraxella catarrhalis, Legionella pneumophila, Bacteroides fragilis, Escherichia coli, Helicobacter pylori* and *Nesseria gonorrhoeae*.

31. The method according to claim 1 where the species of atypical bacteria is selected from the group consisting of *Chlamydophila pneumoniae, Mycoplasma hominism, Mycoplasma pneumoniae* and *Chlamydia trachomatis*.

* * * * *

UNITED STATES PATENT AND TRADEMARK OFFICE
CERTIFICATE OF CORRECTION

PATENT NO. : 8,389,516 B2  Page 1 of 1
APPLICATION NO. : 13/154592
DATED : March 5, 2013
INVENTOR(S) : David John Haydon et al.

It is certified that error appears in the above-identified patent and that said Letters Patent is hereby corrected as shown below:

In the Claims

Column 164, Claim 18, Lines 1-5:

Please delete " 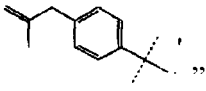 "

and insert -- 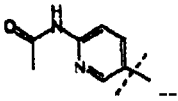 --

Column 164, Claim 18, Lines 25-30:

Please delete " 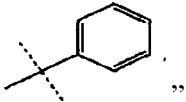 "

and insert -- 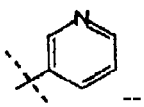 --

Signed and Sealed this
First Day of July, 2014

Michelle K. Lee
*Deputy Director of the United States Patent and Trademark Office*